US006447266B2

(12) United States Patent
Antaki et al.

(10) Patent No.: US 6,447,266 B2
(45) Date of Patent: Sep. 10, 2002

(54) BLOOD PUMP HAVING A MAGNETICALLY SUSPENDED ROTOR

(75) Inventors: James F. Antaki, Allison Park, PA (US); Bradley Paden, Santa Barbara, CA (US); Gregory Burgreen, Pittsburgh, PA (US); Nelson J. Groom, White Marsh, VA (US)

(73) Assignees: University of Pittsburgh, Pittsburgh, PA (US); The United States of America as represented by the United States National Aeronautics and Space Administration, Washington, DC (US)

( * ) Notice: Subject to any disclaimer, the term of this patent is extended or adjusted under 35 U.S.C. 154(b) by 0 days.

(21) Appl. No.: 09/841,223

(22) Filed: Apr. 24, 2001

Related U.S. Application Data

(63) Continuation of application No. 09/356,662, filed on Jul. 19, 1999, now Pat. No. 6,244,835, which is a continuation-in-part of application No. 08/673,627, filed on Jun. 26, 1996, now Pat. No. 6,015,272.
(60) Provisional application No. 60/142,354, filed on Jul. 1, 1999.

(51) Int. Cl.[7] .............................................. F04B 17/00

(52) U.S. Cl. ....................................... 417/356; 604/131

(58) Field of Search ............................... 417/45, 423.3, 417/423.12, 356; 439/78; 29/888.025; 600/16; 604/151, 131; 623/3

(56) References Cited

U.S. PATENT DOCUMENTS

| | | |
|---|---|---|
| 3,143,972 A | 8/1964 | Smith et al. .................. 415/91 |
| 3,155,437 A | 11/1964 | Kinsey et al. |
| 3,647,324 A | 3/1972 | Rafferty et al. |
| 3,823,990 A | 7/1974 | Gillinson, Jr. |
| 3,860,300 A | 1/1975 | Lyman ........................ 308/10 |

(List continued on next page.)

FOREIGN PATENT DOCUMENTS

DE     33 43 186 A1    6/1985

OTHER PUBLICATIONS

Antaki, J.F., "The Streamliner," *Pitt Medicine*, Spring 1995, 12–15.
Hamilton, J., "Can We End Heart Disease," *Business Week*, Sep. 1997, 106–108, 110–111.
Paula, G., "The Mechanics of Anatomy," *Mechanical Engineering*, May 1998, 81–83.
Backers, F.T., "A Magnetic Journal Bearing," *Phillips Technical Review*, 1960–61, 22(7), 323–328.

(List continued on next page.)

*Primary Examiner*—Teresa Walberg
*Assistant Examiner*—Leonid Fastovsky
(74) *Attorney, Agent, or Firm*—Woodcock Washburn LLP

(57) ABSTRACT

A blood pump preferably has a magnetically suspended rotor that rotates within a housing. The rotor may rotate about a stator disposed within the housing. Radial magnetic bearings may be defined within the stator and the rotor in order to suspend the rotor. The radial magnetic bearings may be passive magnetic bearings that include permanent magnets disposed within the stator and the rotor or active magnetic bearings. The pump may further include an axial magnetic bearing that may be either a passive or an active magnetic bearing. A motor that drives the rotor may be disposed within the housing in order to more easily dissipate heat generated by the motor. A primary flow path is defined between the rotor and the stator, and a secondary flow path is defined between the stator and the rotor. Preferably, a substantial majority of blood passes through the primary flow path. The secondary flow path is large enough so that it provides adequate flushing of the secondary flow path while being small enough to permit efficient operation of the radial magnet bearings across the secondary flow path.

25 Claims, 31 Drawing Sheets-

U.S. PATENT DOCUMENTS

| | | | |
|---|---|---|---|
| 3,877,761 | A | 4/1975 | Boden et al. |
| 4,088,018 | A | 5/1978 | Anderson et al. |
| 4,156,548 | A | 5/1979 | Anderson et al. |
| 4,382,199 | A | 5/1983 | Isaacson |
| 4,625,712 | A | 12/1986 | Wampler |
| 4,683,391 | A | 7/1987 | Higuchi |
| 4,688,998 | A | 8/1987 | Olson et al. |
| 4,704,121 | A | 11/1987 | Moise |
| 4,763,032 | A | 8/1988 | Bramm et al. |
| 4,779,614 | A | 10/1988 | Moise |
| 4,817,586 | A | 4/1989 | Wampler |
| 4,846,152 | A * | 7/1989 | Wampler et al. ............. 600/16 |
| 4,895,557 | A * | 1/1990 | Moise et al. ................. 600/16 |
| 4,908,012 | A | 3/1990 | Moise et al. |
| 4,944,722 | A * | 7/1990 | Carriker et al. ............. 600/16 |
| 4,944,748 | A * | 7/1990 | Bramm et al. ................... 62/3 |
| 4,957,504 | A * | 9/1990 | Chardack ...................... 623/3 |
| 4,994,017 | A | 2/1991 | Yozu |
| 4,994,078 | A | 2/1991 | Jarvik |
| 4,995,857 | A | 2/1991 | Arnold |
| 5,003,211 | A | 3/1991 | Groom |
| 5,003,235 | A | 3/1991 | Groom |
| 5,049,134 | A * | 9/1991 | Golding et al. ............ 604/151 |
| 5,055,005 | A | 10/1991 | Kletschka |
| 5,055,055 | A * | 10/1991 | Bakker ......................... 439/78 |
| 5,078,741 | A * | 1/1992 | Bramm et al. ................. 623/3 |
| 5,092,879 | A | 3/1992 | Jarvik |
| 5,098,256 | A | 3/1992 | Smith |
| 5,111,102 | A | 5/1992 | Meeks |
| 5,112,200 | A | 5/1992 | Isaacson et al. |
| 5,112,202 | A | 5/1992 | Oshima et al. |
| 5,112,292 | A | 5/1992 | Hwang et al. |
| 5,112,349 | A | 5/1992 | Summers et al. |
| 5,118,264 | A | 6/1992 | Smith |
| 5,145,333 | A | 9/1992 | Smith |
| 5,195,877 | A | 3/1993 | Kletschka |
| 5,209,650 | A | 5/1993 | Lemieux |
| 5,211,546 | A | 5/1993 | Isaacson et al. ............ 417/356 |
| 5,267,940 | A | 12/1993 | Moulder |
| 5,275,580 | A | 1/1994 | Yamazaki |
| 5,282,849 | A | 2/1994 | Kolff et al. |
| 5,290,227 | A | 3/1994 | Pasque |
| 5,300,841 | A | 4/1994 | Preston et al. |
| 5,326,344 | A | 7/1994 | Bramm et al. |
| 5,344,443 | A | 9/1994 | Palma et al. |
| 5,376,114 | A | 12/1994 | Jarvik |
| 5,385,581 | A | 1/1995 | Bramm et al. |
| 5,441,535 | A | 8/1995 | Takahashi et al. |
| 5,443,503 | A | 8/1995 | Yamane |
| 5,470,208 | A | 11/1995 | Kletschka |
| 5,507,629 | A * | 4/1996 | Jarvik ..................... 417/423.3 |
| 5,527,159 | A * | 6/1996 | Bozeman, Jr. et al. ........ 417/45 |
| 5,678,306 | A * | 10/1997 | Bozeman, Jr. et al. .. 29/888.025 |
| 5,692,882 | A * | 12/1997 | Bozeman, Jr. et al. ........ 417/45 |
| 5,695,471 | A * | 12/1997 | Wampler ..................... 604/131 |
| 5,840,070 | A * | 11/1998 | Wampler ..................... 604/131 |
| 5,957,672 | A * | 9/1999 | Aber ..................... 417/423.12 |
| 6,015,272 | A | 1/2000 | Antaki et al. ............... 417/356 |
| 6,080,133 | A * | 6/2000 | Wampler ..................... 604/131 |
| 6,244,835 | B1 * | 6/2001 | Antaki et al. ............... 417/356 |

OTHER PUBLICATIONS

Ball Brothers Research Corporation, *Annular Momentum Control Device* (AMCD), Laboratory Model Development, NASA CR–144917, 1976, vol. 1, 4–6–4–9.

Burgreen, G.W. et al., "CFD–Based Design Optimization of a Three Dimensional Rotary Blood Pump," AIAA Paper No. 96–4185, 1996, 1773–1778.

Gurumoorthy, R. et al., "Implementation of Sensorless Control of Radial Magnetic Bearing," *Proceedings of MAG '95*, Alexandria, Aug. 1994, 239–248.

Henrikson, C.H. et al., "Magnetically Suspended Mementum Wheels for Spacecraft Stabilization," presented at the AIAA 12th Aerospace Sciences Meeting, Washington, D.C., Jan. 30–Feb. 1, 1974, Paper No. 74–128, pp. 4–5.

Okado, Y. et al., "Sensorless Magnetic Levitation Control by Measuring the PWM Carrier Frequency Content," *Proceedings of the Third International Symposium on Magnetic Bearings* Alexandria, Jul. 1992, 176–183.

Vischer, D. et al., "A New Approach to Sensorless and Voltage Controlled AMBs Based on Network Theory Concept," *2nd International Conference on Magnetic Bearings*, Tokyo, Jul. 1990, 301–306.

Dieter Vischer, et al., "A new approach to sensorless and voltage controlled AMBs based on network theory concepts," $2^{nd}$ *International Symposium on Magnetic Bearing*, 1990, 301–306.

Yonnet, J.P. et al., "Stacked Structures of Passive Magnet Bearings," *J. Appl. Physics*, 1991, 70(10), 6633–6635.

U.S. application Ser. No. 60/142,354, Antaki et al., filed Jul. 1, 1999.

* cited by examiner

FIG.3
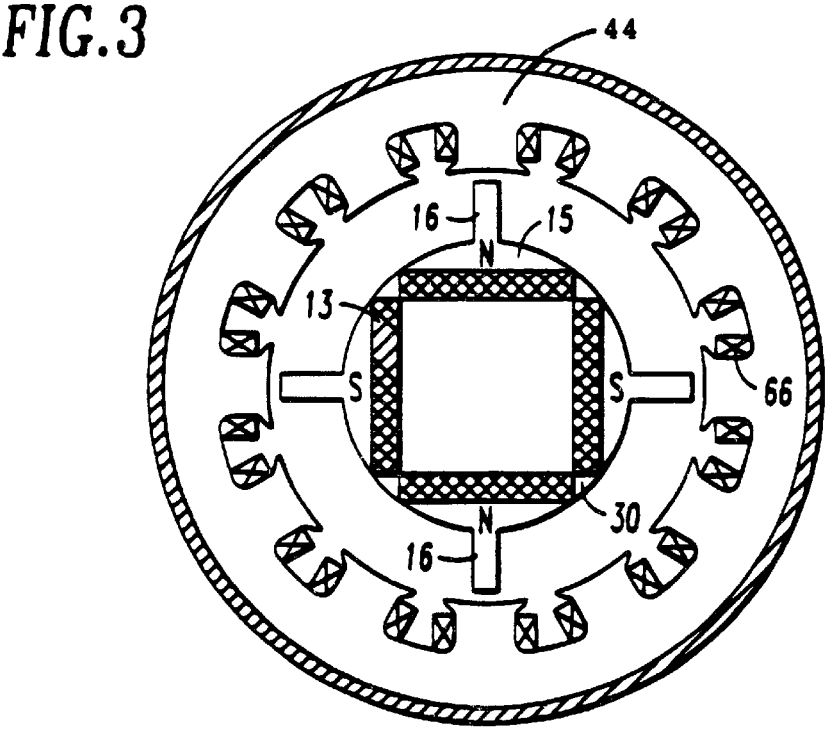
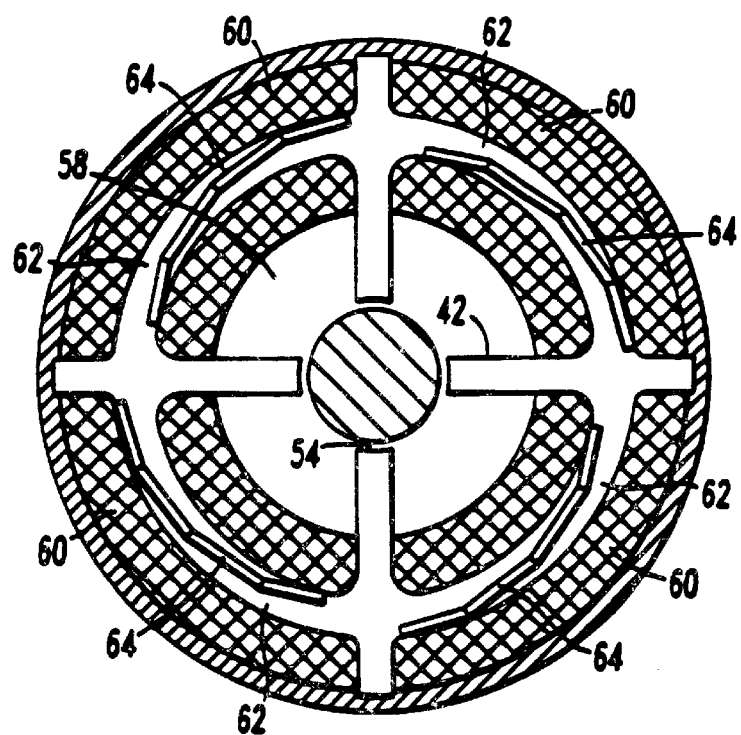
FIG.4

FIG.24
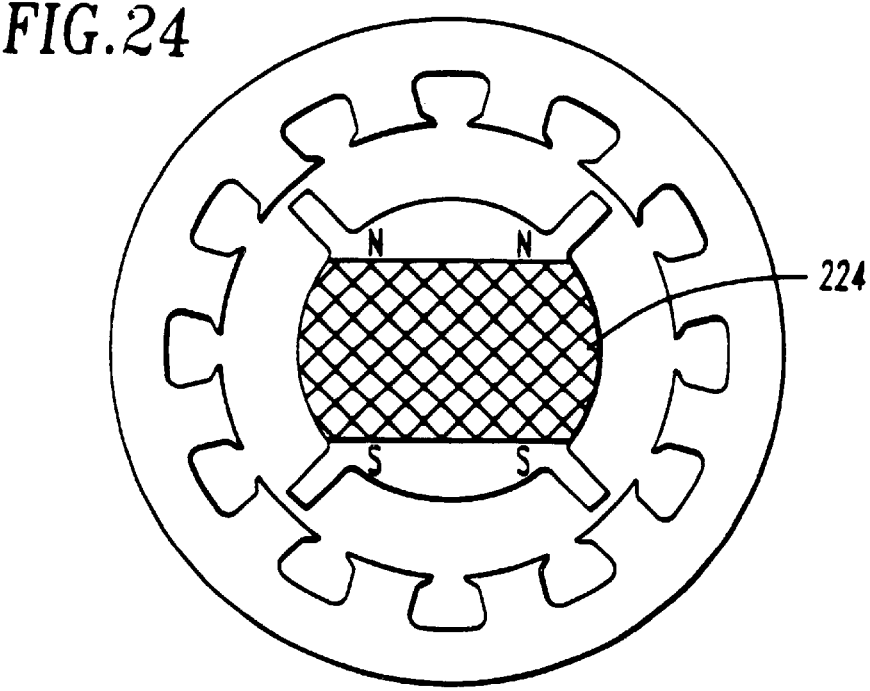
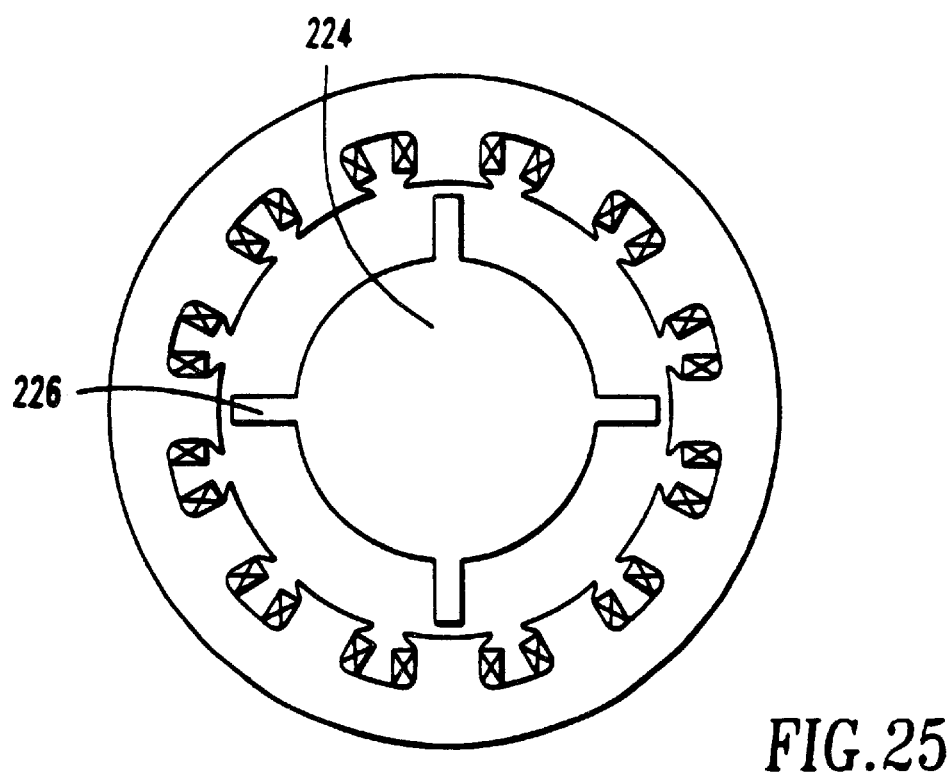
FIG.25

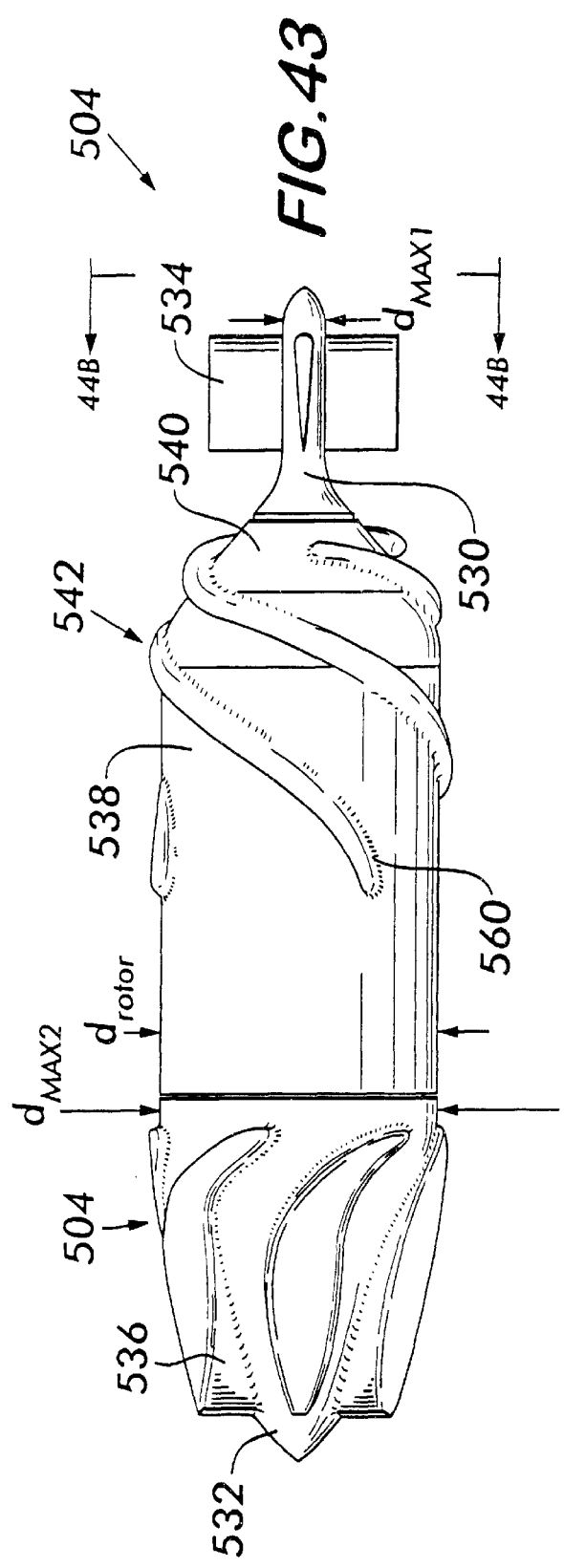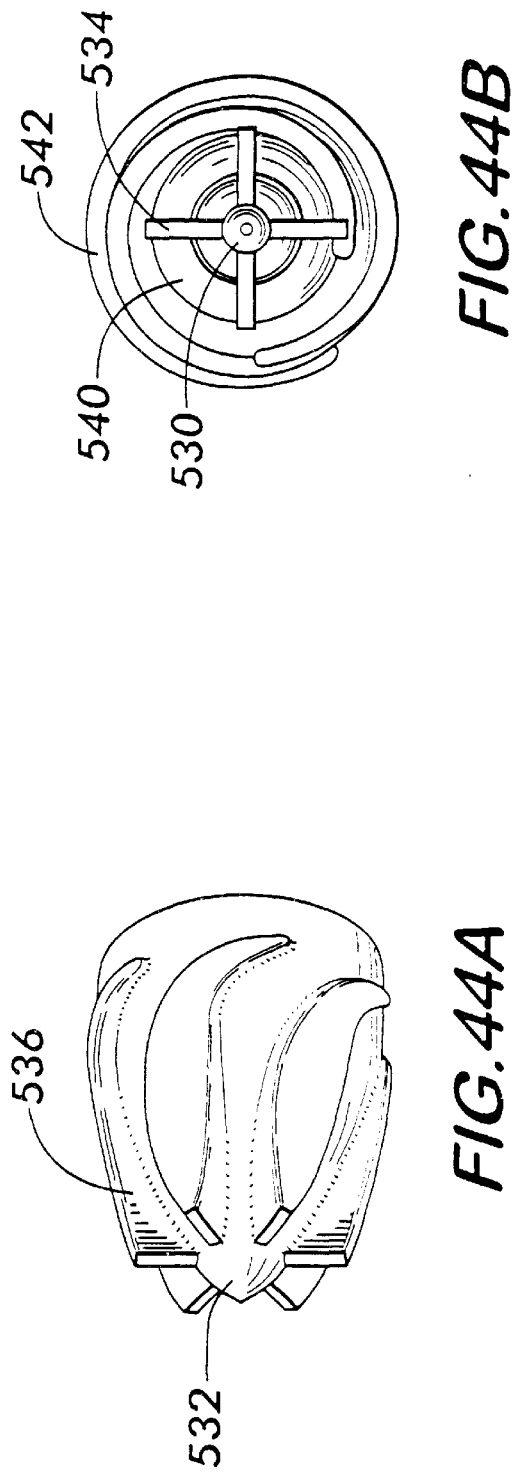

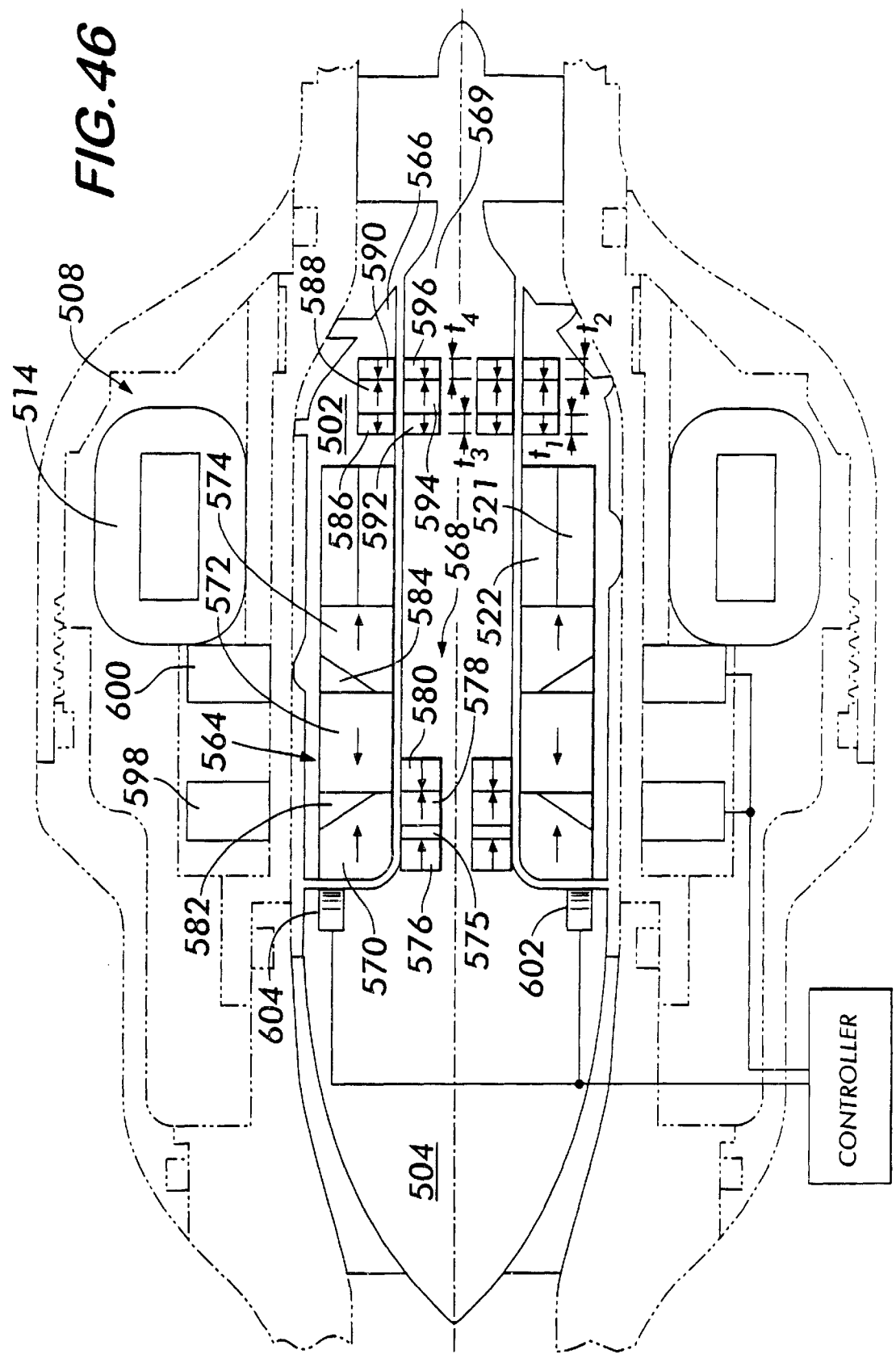

BLOOD PUMP HAVING A MAGNETICALLY SUSPENDED ROTOR

CROSS REFERENCE TO RELATED APPLICATIONS

This Application is a continuation of U.S. Application Ser. No. 09/356,662 filed on Jul. 19, 1999, now U.S. Pat. No. 6,244,835 entitled "Blood Pump Having A Magnetically Suspended Rotor", which is a continuation-in-part application of U.S. patent application Ser. No. 08/673,627 filed on Jun. 26, 1996, now U.S. Pat. No. 6,015,272 entitled "Magnetically Suspended Miniature Fluid Pump And Method of Making The Same," and claims priority under 35 U.S.C. §119(e) to provisional patent application Ser. No. 60/142,354, filed on Jul. 1, 1999, entitled "An Improved Blood Pump Having A Magnetically Suspended Rotor," and hereby claims the benefit of the filing dates of these applications and incorporates by reference theses applications in their entireties.

STATEMENT OF GOVERNMENT RIGHTS

The invention described herein was jointly made by employees of the United States Government and by employees of University of Pittsburgh, and it may be manufactured and used by or for the United States Government for United States Government purposes without payment of royalties thereon or therefore.

FIELD OF THE INVENTIONS

This invention relates to blood pumps that have a magnetically suspended rotor and methods of making the same. This invention also includes blood pumps that have a housing, a rotor, a stator member attached to the housing, a means for levitating the rotor such that the rotor is substantially centered within the housing, and means for rotating the rotor. This invention further includes blood pumps that have a geometric configuration that minimizes shear stresses on the blood, enhances biocompatibility and prevents activation of blood platelets, and thereby prevents thrombosis.

BACKGROUND OF THE INVENTION

The use of rotary pump ventricular assist devices for aiding a patient's heart in pumping blood is well known. Such rotary pump ventricular assist devices may be connected to a patient's heart in a left-ventricular assist configuration, in a right-ventricular assist configuration or in a bi-ventricular assist configuration. For instance, if the left-ventricular assist configuration is adopted, the rotary pump is connected between the left ventricle of the patient's heart and the aorta. Generally, a rotary pump includes a housing having an inlet and an outlet, an impeller positioned within the housing and impeller blades extending from the impeller. The blood enters the inlet of the housing and is pumped by the rotating impeller through the housing to the outlet and into the patient's circulatory system.

Blood pumps are a unique class of devices. This is so, inter alia, because artificially pumping blood presents many issues that are not present when pumping fluids in pumps that need not be biocompatible. When pumping blood, it is imperative to prevent damage to the blood cells because this can lead to the activation of platelets, coagulation and potentially fatal thrombosis. For instance, because coagulation can result from increased temperatures, the temperature of the blood must be carefully controlled. Moreover, blood cells may coagulate or albumin of the blood denature if the blood temperature reaches forty-two degrees centigrade (42° C.). Even at lower temperatures, some adverse effects may occur. If a blood pump is relatively inefficient, the pump can impart excessive energy to the blood, which usually takes the form of heat. Therefore, it is imperative that blood pumps be efficient to avoid transferring heat to the blood. Per force, effective heat management is very important. Further, sudden flow retardations may cause excessive shear stresses.

Moreover, numerous studies have proven that exposing blood to high stresses, such as shear stresses, results in immediate or delayed destruction of blood cells. As a result of the rotation of an impeller, regions of turbulence, jet formation, cavitation and rapid acceleration may be created in blood pumping operations, causing the blood cells flowing through the pump to break down and rupture. Further, edges or protruding surfaces within a blood pump can cause shear stresses and the breakdown of blood cells. Also, the geometric configuration of a pump may cause localized regions of retarded flow or stagnation. Flow stagnation can cause blood elements to deposit on the pump structure, coagulate and possibly result in thrombosis.

Many attempts have been made to meet the design constraints for using blood pumps as ventricular assist devices. One type of conventional rotary pump utilizes mechanical bearings that necessitate a lubricant flush or purge with an external lubricant reservoir for lubricating the bearing and minimizing heat generation. Examples of this type of rotary pump are illustrated in U.S. Pat. Nos. 4,944,722 and 4,846,152 issued to Carriker et al. and Wampler et al., respectively. There are many disadvantages of this type of rotary pump. The percutaneous supply of the lubricant purge fluid degrades the patient's quality of life and provides the potential for adverse reaction and infection. Seals for the external lubricant are notoriously susceptible to wear and to fluid attack, which may result in leakage. This may cause the pump to seize. Also, an additional pump is needed for delivery of the lubricant to the bearing. Yet another disadvantage of this type of rotary pump is that the bearings need to be replaced over time because of wear due to the bearings directly contacting other pump structures.

In order to eliminate the need for an external purge of lubricant, rotary pumps having a magnetically suspended impeller have been created. By utilizing a magnetically suspended impeller, direct contact between the bearing and other pump structures, as well as external lubricant purges are eliminated. Examples of this type of rotary pump are disclosed in U.S. Pat. Nos. 5,326,344 and 4,688,998 issued to Bramm et al. and Olsen et al. respectively. These types of rotary pumps generally include an impeller positioned within a housing, wherein the impeller is supported and stabilized within the housing by a combination of permanent magnets positioned in the impeller and the housing and electromagnets positioned within the housing. The impeller is rotated by a ferromagnetic stator ring mounted within the housing and electromagnet coils wound around two diametrically opposed projections. The ferromagnetic impeller and the electromagnetic coils are symmetrically positioned with respect to the axis of the rotary pump and thus, impose an axially symmetric force on the fluid passing through a single annular gap formed between the housing and the impeller.

A disadvantage of these types of rotary pumps is that there is only one annular gap for the blood to pass through, which serves competing purposes with respect to fluid flow and the magnetic suspension and rotation of the impeller. Regarding fluid flow, the gap is desired to be large for efficient pumping whereas, for efficient suspension and rotation of the impeller, the gap is desired to be small. In this type of rotary pump, the fluid gap must be relatively small, so as to provide the proper magnetic suspension. This does not allow for efficient pumping of blood because the gap must be made relatively small.

Blood pumps have been designed with hydrodynamic bearings, as opposed to magnetic bearings. Due to the differential pressure across these types of bearings any flushing of these types of bearings is generally minimal. Thus, these types of pumps generally have a relatively stagnant region of blood within the bearing. Therefore, a drawback of these types of pumps is that the blood is relatively stagnant in the regions around the bearings, which can lead to the deposition of blood elements, coagulation and potentially thrombosis.

Another concern with ensuring the biocompatibility of blood pumps is to minimize the size of the blood pumps. By minimizing the size of blood pumps, the amount of foreign surface area that the blood must contact decreases. This decreases the likelihood that the blood will become contaminated or the blood cells will be damaged. There is a competing concern with minimizing the size of blood pumps. As the size of blood pumps decreases, the flow paths become narrower, the required rotational speed becomes higher and the likelihood of increased shear stresses increases. Therefore, it is important in designing relatively small blood pumps to prevent excessive shear stresses.

The blood pumps of the present invention provide for improvements in pumping blood. These features are related, inter alia, to the magnetic suspension of the rotor and enhancing the biocompatibility and reliability of the pumps through certain geometric features of the pumps while simultaneously minimizing the size of the pumps.

SUMMARY OF THE INVENTION

The blood pumps of this invention have a housing, a stator or stationary member and a rotor magnetically suspended between the stator and the housing. A primary flow path may be defined between the housing and the rotor and a secondary flow path may be defined between the stator and the rotor. The primary flow path provides the flow path for the substantial majority of blood flowing through the pump. Defined within the pump may be a radial magnetic bearing that suspends the rotor radially within the pump. Preferably, the radial magnetic bearing includes a stack of magnets disposed in the rotor and a stack of magnets disposed within the stator and aligned with those in the rotor. These two stacks of magnets interface across the secondary flow path to suspend the rotor radially from the stator. By providing a secondary flow path across which the radial bearing operates, the primary flow path can be large enough to provide an adequate flow rate or volume of blood pumped.

The pumps may also have a thrust bearing for controlling the axial position of the rotor. In a preferred embodiment, the thrust bearing includes the radial bearing, thrust coils disposed within the housing, pole pieces, disposed within the rotor, a sensor and a controller. The radial bearing also produces a force in the axial direction. The thrust coils which are preferably disposed in the housing, cooperate with the pole pieces, which are preferably disposed in the rotor, to produce a counteracting force in the axial direction. The blood flowing through the pump also imparts an axial force on the rotor. In order to maintain the rotor's axial position, the pumps preferably have the controller and the sensor referred to above. The sensor preferably includes a sensing coil disposed within the stator that communicates with the rotor to determine the axial position of the rotor. The controller is in electrical communication with the sensor and the thrust coils. Based on the position sensed by the sensing coils, the controller adjusts the electrical current through the thrust coils. This adjusts the axial force exerted on the rotor, so that the rotor can be positioned to its preferred axial location within the pump. In a preferred embodiment the controller is a Virtually Zero Power controller.

The motor stator for driving the rotor is preferably disposed within the housing and communicates with a rotor magnet across the primary flow path to rotate the rotor. By placing the motor stator within the housing, as opposed to the stator or stationary member around which the rotor rotates, the heat generated by the motor can be more easily dissipated away from the blood. This enhances the biocompatibility of the pumps. Further, by placing the motor stator within the housing, larger wire can be used due to the increased volume in the housing relative to the motor stator. This is significant because using larger wire reduces the ohmic heating of the motor stator.

As alluded to above, the rotor is magnetically suspended by the interaction of magnets across the secondary flow path. The secondary flow path is of a size that balances two competing considerations. The secondary flow path must be large enough to provide adequate flushing throughout the secondary flow and thereby prevent stagnation and the collection of blood cells along localized regions of the secondary flow path. Stagnation and the collection of blood cells can lead to thrombosis and eventually embolization. The secondary flow path must also be small enough, so that the radial magnetic bearing operates effectively in order to minimize the size of the pump and the foreign surface area in contact with the blood. Thus, the secondary flow path is optimally sized so as to balance these competing considerations.

In a preferred embodiment, the flow through the secondary flow path can be retrograde, opposing the direction of flow through the primary flow path. Increased flushing of the secondary flow path can be achieved with retrograde flow. It has been found that if flow is in the same direction as the primary flow path, the flow rate is insufficient to provide the desired amount of flushing without further increasing the size of the secondary flow path and the pump.

Preferably, the stator, the rotor and the housing are all shaped so as to create streamlined or relatively smooth flow paths for the blood and to prevent relatively sharp surfaces or edges from contacting the blood. As described above, such surfaces are undesirable because they increase shear stresses on the blood and increase the likelihood that blood cells will collect at such a surface and coagulate.

Other features of the invention are provided below.

BRIEF DESCRIPTION OF THE DRAWINGS

The accompanying drawings show the present preferred embodiments of the Inventions in which:

FIG. 3 is a cross-sectional view of the motor stator and motor rotor of the rotary fluid pump shown in FIG. 1 taken along line III—III.

FIG. 4 is a cross-sectional view of the stator member and impeller of the rotary fluid pump shown in FIG. 1 taken along line IV—IV.

FIG. 24 is a cross-sectional view of a two-pole motor having four impeller blades which is an alternative motor for the rotary pump shown in FIG. 1.

FIG. 25 is a cross-sectional view of a variable reluctance motor hybridized with impeller blades.

FIG. 43 is a side view of a preferred embodiment of the rotor and the stator of the preferred embodiment of FIG. 39.

FIG. 44A is an isometric view of a preferred embodiment of a second end of the stator of FIG. 43.

FIG. 44B is an end view along line 44B—44B of FIG. 43.

FIG. 46 is a diagrammatical view of a preferred embodiment of some of the bearings of the preferred embodiment of FIG. 39.

FIGS. 1 through 5 illustrate a present preferred embodiment of the invention substantially comprising an axial rotary pump having a housing 12, an impeller 14 with impeller blades 16, a stator member 18, means for levitating the impeller 14 within the housing 12 at a centered position and means for rotating the impeller 14. The housing is preferably cylindrical and has an internal surface 20, an external surface 22 concentrically spaced from the internal surface 20, an inlet 24 and an outlet 26. The internal surface 20 defines an internal region 28 in which the impeller 14 is positioned. The impeller 14 (FIG. 2) has a substantially axially symmetric elongated body 30, a conical-shaped nose 32 and a conical-shaped tail 34, as best shown in FIG. 2. Magnetic targets 36 and 38 are positioned over the impeller nose 32 and the impeller tail 34, respectively. The impeller blades 16 are substantially helical soft magnetic material and are attached to permanent magnets 13 on the body of the impeller 14, as best shown in FIG. 3.

The stator member 18 has an upstream set of stationary blades 40, a downstream set of stationary blades 42, a motor stator 44 and an angle sensor 46, as shown in FIG. 1. The upstream set of stationary blades 40 and the downstream set of stationary blades 42 are attached to the housing 12 and converge toward the longitudinal axis 48 of the housing 12, wherein the free ends of the upstream set of stationary blades 40 and the free ends of the downstream set of stationary blades 42 define an upstream passageway 50 and a downstream passageway 52, respectively. The impeller nose 32 and the impeller tail 34 extend within the upstream passageway 50 and downstream passageway 52 respectively, such that gaps 54 and 56 are formed between the free ends of the upstream and downstream sets of the stationary blades 40 and 42 and the impeller nose 32 and the impeller tail 34, respectively. As can be best seen in FIG. 4, the downstream set of stationary blades 42 further defines fluid flow regions within the internal region 28, as seen in FIG. 1, of the housing 12. Although not shown, similar fluid flow regions are defined by the upstream set of stationary blades 40. Although FIG. 4 is a cross-section taken through the downstream set of stationary blades 42, it will be appreciated that a similar cross-section taken through the upstream set of stationary blades 40 would be substantially identical. The upstream and the downstream sets of stationary blades 40 and 42 are preferably made from soft magnetic material; however, they can be made from permanent magnets located in series. Although each set of the upstream and downstream sets of stationary blades 40 and 42, are shown as comprising four stationary blades, other combination of blades can be used.

Figure 1:
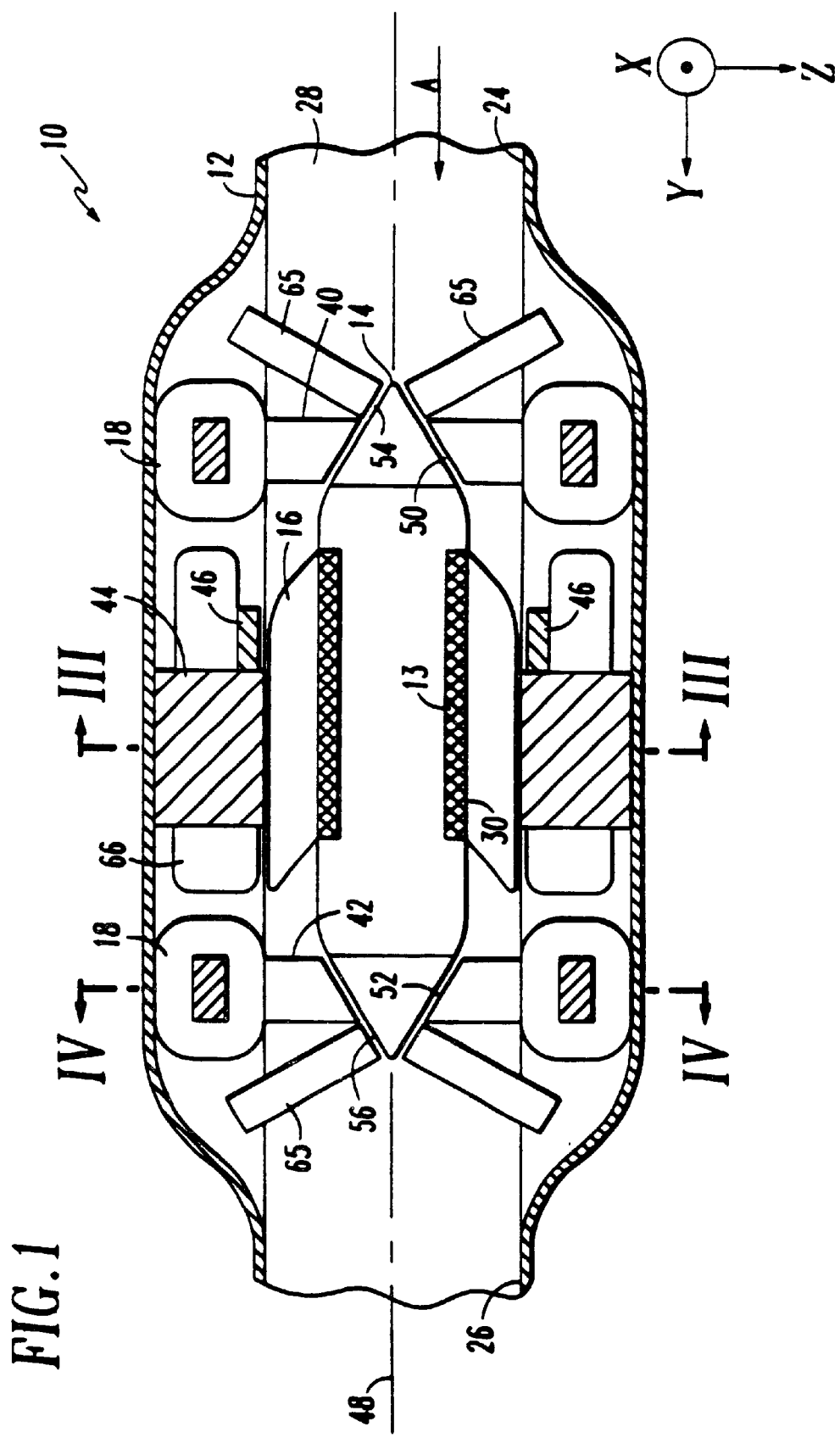
FIG. 1 is a cross-sectional view of a present preferred embodiment of a rotary fluid pump having a magnetically suspended impeller.
Figure 2:
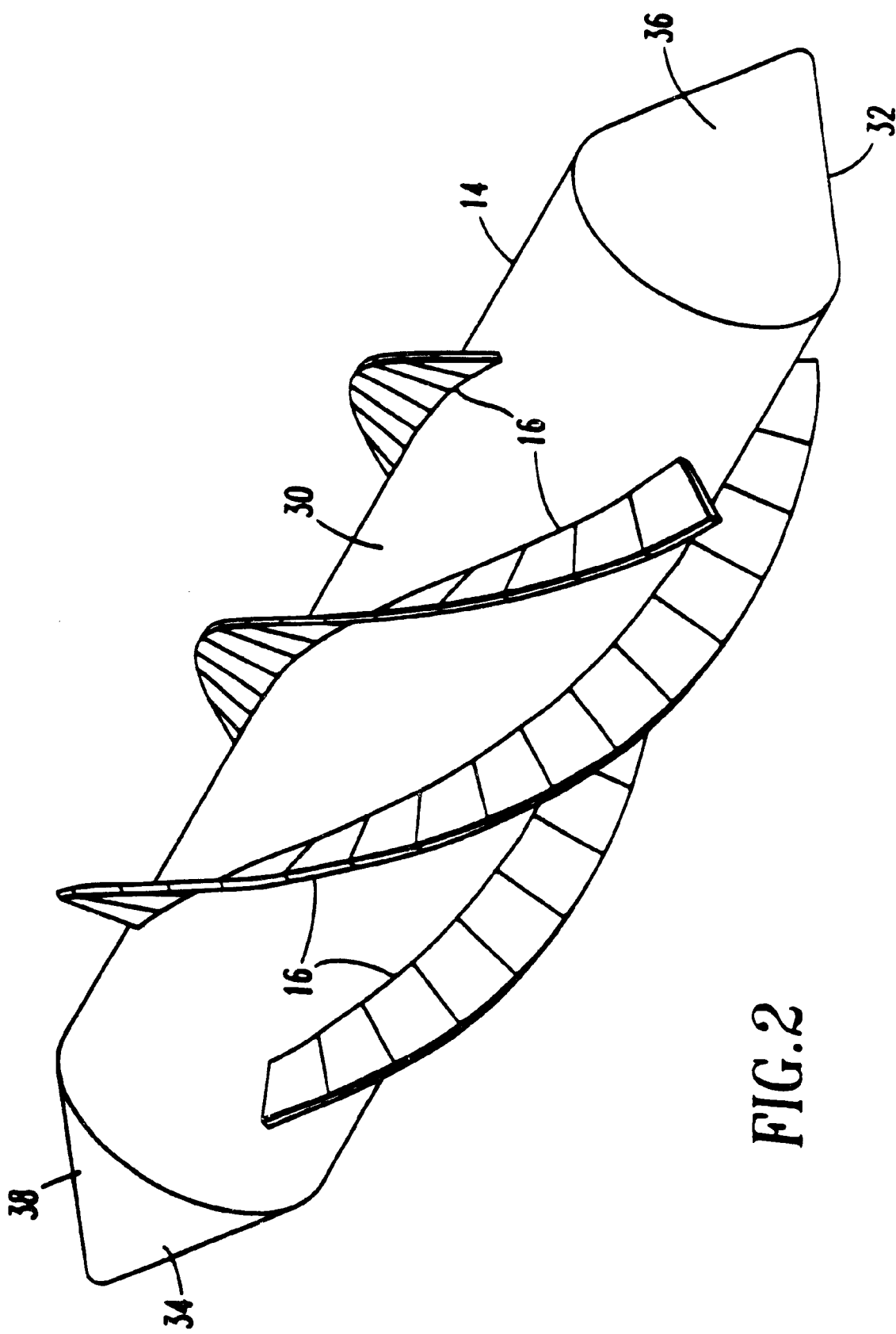
FIG. 2 is a perspective view of the impeller of the rotary fluid pump shown in FIG. 1.

The means for rotating the impeller is a brushless DC motor having a motor stator 44, an angle sensor 46, an impeller elongated body 30 having permanent magnets 13, flux focusing structures 15 made from a soft magnetic material, and impeller blades 16 which serve as the motor poles and are made from a soft magnetic material coated with a bio-compatible material. The motor stator 44 and the angle sensor 46 are positioned within the housing 12 between the internal surface 20 and the external surface 22. Motor stator coils 66, as shown in FIG. 3, are wound on the motor stator 44. The current through the motor stator coil can be controlled to affect the desired speed of the impeller with a conventional means. Although this is the preferred means for rotating the impeller, a variety of other rotational means can be used in the invention. Alternatively, the brushless D.C. motor can take the form of a two pole motor.

The means for levitating (FIG. 4) the impeller 14 are conical bearings which includes independently controlled coils 60 wound around the backiron segments 62, which are made from a soft magnetic material, segmented and radially magnetized permanent magnets 64, and four stationary blades 42, which act as pole pieces. The coils 60 are controlled to center the impeller 14 between the stationary blades 42. This design is particularly suited for use where fluid flow is required through the four fluid flow regions 58. The levitation means depicts an active radial bearing.

This conical bearing provides radial stiffness and axial stiffness when it is controlled with a feedback system and amplifier. Electromagnetic coils 60 wound around the backiron segments 62 direct the magnetic flux from the electromagnetic coils 60 such that the impeller tail 34 is suspended and substantially centered within the downstream passageway 52. Further, permanent magnets 64 are provided within the backiron segments 62 in order to provide a permanent bias thus, reducing the required steady state current. By winding electromagnetic coils 60 around the backiron segments rather than around the downstream set of stationary blades 42, the fluid flow regions 58 remain large enough for blood to pass therethrough without forming regions of stagnation or turbulent flow.

Position sensors 65 are attached to the inlet 24 and the outlet 24 of the housing 12 and adjacent to the impeller nose 32 and the impeller tail 34. Any position sensor can be used including a Hall-effect, eddy-current, or infrared optical sensors. The impeller 14 position can even be sensed from changes in inductances of the coils 60. Magnetic bearings controlled with such a sensing scheme are referred to as sensorless bearings when used in conjunction with bearings as described in "Analysis of Self-Sensing Active Magnetic Bearings Working On Inductance Measurement Principle," D. Vischer et al., Second International Conference on Magnetic Bearings, Tokyo, pp. 301–309, July 1990.

Figure 5:
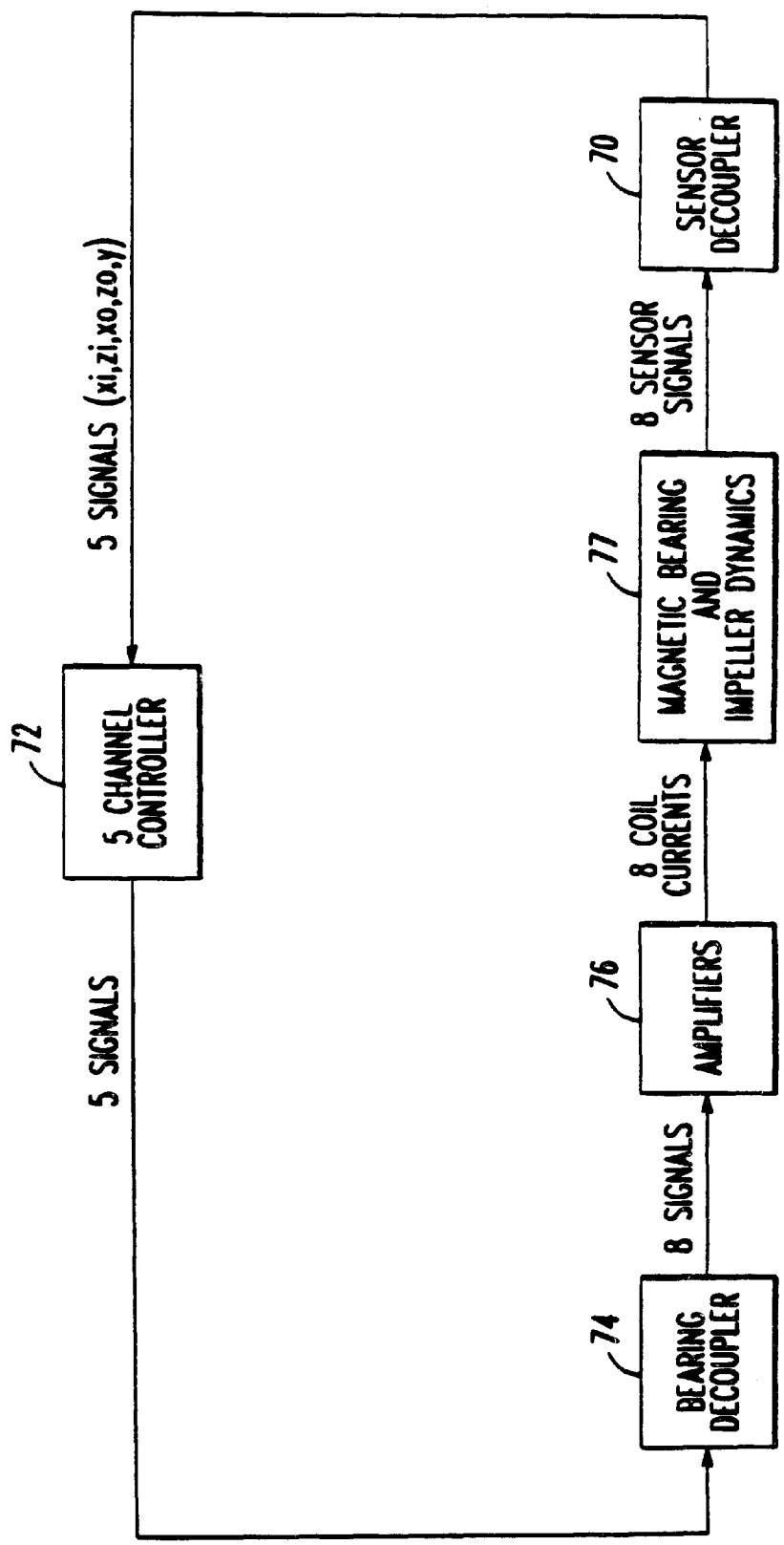
FIG. 5 is a schematic diagram of the magnetic bearing control used in the rotary fluid pump shown in FIG. 1.

In order to magnetically levitate the impeller 14 a feedback controller is used as diagramed in FIG. 5. Position errors are measured with 8 position sensors 65 and transformed into error signals $x_i$, $z_o$, $x_o$, $z_i$ and y, while $x_i$ and $z_i$ measurements correspond to the x and z impeller displacement of the impeller measured at the inlet 24, and $x_o$ and $z_o$ are measured at the outlet 26. The error transformation is accomplished with the sensor decoupler 70 shown in FIG. 5 which is simply a matrix multiplication accounting for the position and orientation of the sensors 65. The five principle displacement errors are filtered independently with the five channel controller 72, which outputs five desired restoring forces to be applied to the impeller 14. The bearing decoupler 74 transforms these commands via a matrix multiplication into an appropriate coil current pattern to be applied to the coils 60. The current commands are input to an amplifier 76 which drives the coils 60. The principle of decoupling is well-known, as are various kinds of controls used in the five channel controller. Some examples of control algorithms are proportional-integral-derivative and zero-power control algorithms. The magnetic bearing sensors and impeller dynamics 77 model how the bearing fluxes react to the coil currents and how the impeller responds to the magnetic forces created by the bearing fluxes.

During operation of the rotary pump 10, the blood enters the inlet 24 of the housing 12 in the direction of arrow A. The blood passes over the impeller nose 32 through the gap 54 and the fluid regions 58 shown in FIG. 4. The upstream set of stationary blades 40 serve to straighten the incoming blood flow. The impeller 14 is rotated by the rotating means and the impeller blades 16 accelerate and impart energy to the blood such that the blood moves through the housing 12 toward the outlet 26. The downstream set of stationary blades 42 function to recover velocity energy in the form of pressure energy from the blood flow exiting the impeller blades 16. Before exiting the housing 12, the blood passes through the gap 56 and the fluid flow regions 58 formed by the downstream set of stationary blades 42. The gaps 54 and 56 are sized and proportioned such that they are large enough to prevent regions of stagnation and excessive shear from forming while being small enough to provide efficient magnetic suspension of the impeller 14. Furthermore, the axially symmetric configuration of the impeller elongated body 30 provides for blood to flow through the housing 12 without creating regions of stagnation or excessive shear.

As noted above, the impeller nose 32 and the impeller tail 34 are magnetically suspended and centered within the housing 12 by the magnetic flux created by the electromagnetic coils 60 and directed through the upstream and downstream sets of stationary blades 40 and 42. The gaps 54 and 56 are small enough to allow for the magnetic flux to be directed across the gaps without a substantial increase in the magnetic circuit reluctance. If during pumping of the blood, the impeller 14 moves from its centered position within the housing 12, position sensors 65 will detect this movement and the means for levitating the impeller 14 will apply a net force and moment to the impeller 14 to reposition the impeller 14 to its centered position within the housing 12. For example, a net force in the y direction is accomplished by increasing the flux in the outlet gap 56 and decreasing the flux in the inlet gaps 54 with appropriate corresponding coil currents. The calculation of the currents is accomplished with the sensor decoupler of the five channel controller 72, and the bearing decoupler 74 working in combination. Alternatively, the sensing of the movement of the impeller 14 can be accomplished by estimating the coil inductances from the coil voltages and current and then calculating the gap from the coil inductances.

The variation of magnetic components which include both electric motors and magnetic bearings is extensive and well-documented. Below are described some typical magnetic components and how some of these magnetic components can be used in embodiments of the present preferred invention.

Figure 6:
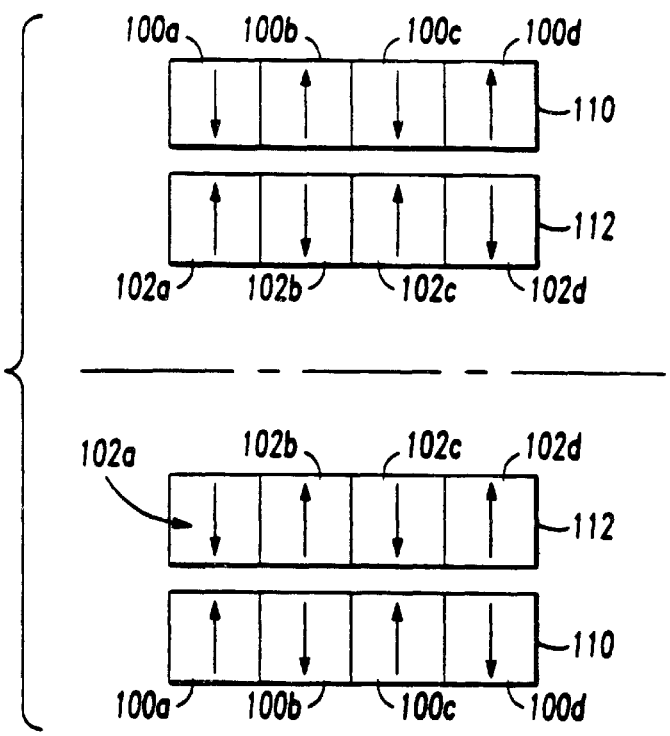
FIG. 6 is a schematic view of a passive radial bearing which is a permanent magnet bearing stator member.

Passive Radial Bearing (PRB): FIG. 6 shows a common design of a passive radial bearing (PRB) which is a permanent magnet bearing. It consists of alternatively magnetized annular permanent magnets 100a, 100b, 100c, 100d, 102a, 102b, 102c and 102d comprising two annular magnet rings 110 and 112, respectively, of the passive radial bearing. Either annular ring 112 or 110 can serve as either the impeller or the stator of a rotary pump. The number of permanent magnets in the embodiment of the rings 110, 112 shown is the same, but not necessarily four. Other numbers of magnets may be employed.

Figure 7:
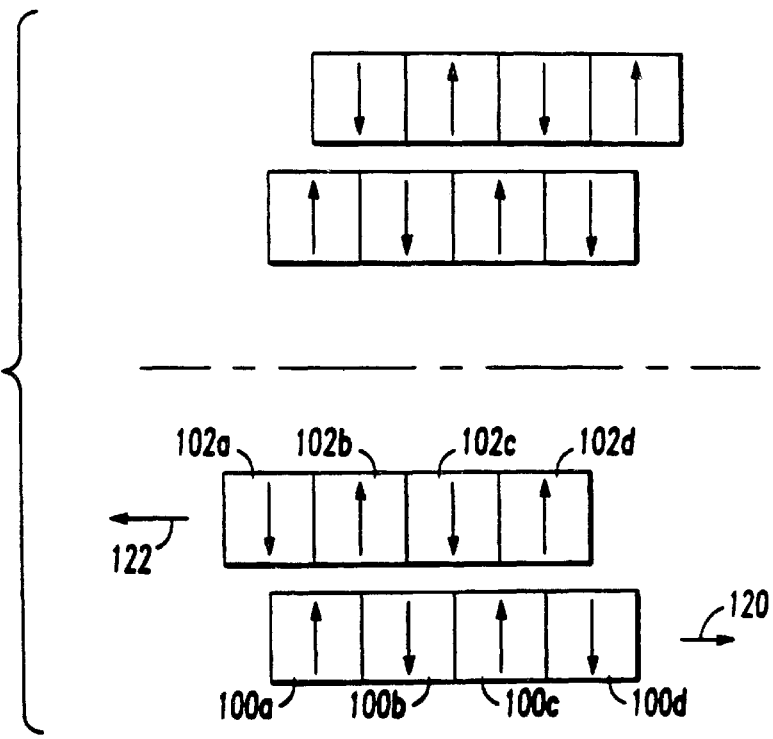
FIG. 7 is a schematic view of the passive radial bearing of FIG. 6 having an axial offset.

The annular magnet rings 110 and 112 are magnetized to provide radial stiffness. However, it is a property of this type of bearing that the axial stiffness is negative with a magnitude equal to twice the radial stiffness. Although this negative stiffness cannot be used alone for axial positioning, it can be used to provide axial bias forces as shown in FIG. 7. By axially shifting the annular magnet rings 110 and 112 relative to each other net steady state forces 120 and 122 can be applied in the axial direction as shown by the arrows. This is due to the fact that magnet 102a is applying a force on magnet 100a in the direction 120 and magnet 102b is applying a force on magnet 100a in the direction 120. Similar interaction occur amongst the other magnets. Passive radial bearings are further described in "Stacked Structures of Passive Magnetic Bearings", J. P. Yonnet et al., Journal of Applied Physics, vol, 70, no-10, pp. 6633–6635, which is hereby incorporated by reference.

Figure 8:
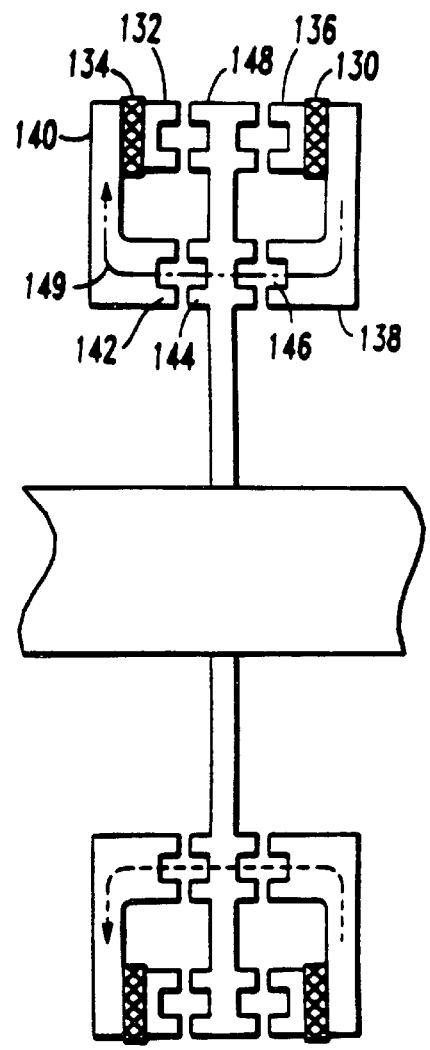
FIG. 8 is a cross-sectional view of a passive radial bearing where the pole pieces are notched to provide pole saliency.

Another kind of PRB is shown in FIG. 8. This bearing has a stator 130a which includes stator magnets 130 and 134 and soft magnetic stator pole pieces 132, 136, 138, 140. The bearing impeller 148 is a soft magnetic material with teeth 144. Permanent magnets 130 and 134 are magnetized axially, so that a magnetic flux passes through pole pieces 132, 136, 138, and 140 and through the bearing impeller 148 in a closed loop as shown by arrow 149. The impeller teeth 144 and the stator teeth 142 tend to align to minimize the reluctance of the magnetic circuit which results in the radial position of this bearing. This passive radial bearing is unstable in the axial direction as is the bearing of FIG. 6. The recesses 146 defined by teeth 142 may be filled with nonmagnetic material to eliminate blood stagnation zones. Although in FIG. 8, the structure designated by reference number 148 rotates and serves as the impeller, and the structure designated by reference number 130a serves as the stator, it will be appreciated that the structure designated by reference number 148 could be fixed, so that it serves as the stator. Likewise, the structure designated by reference number 130a could be free to rotate and have the impeller blades, so that it serves as the impeller.

Figure 9:
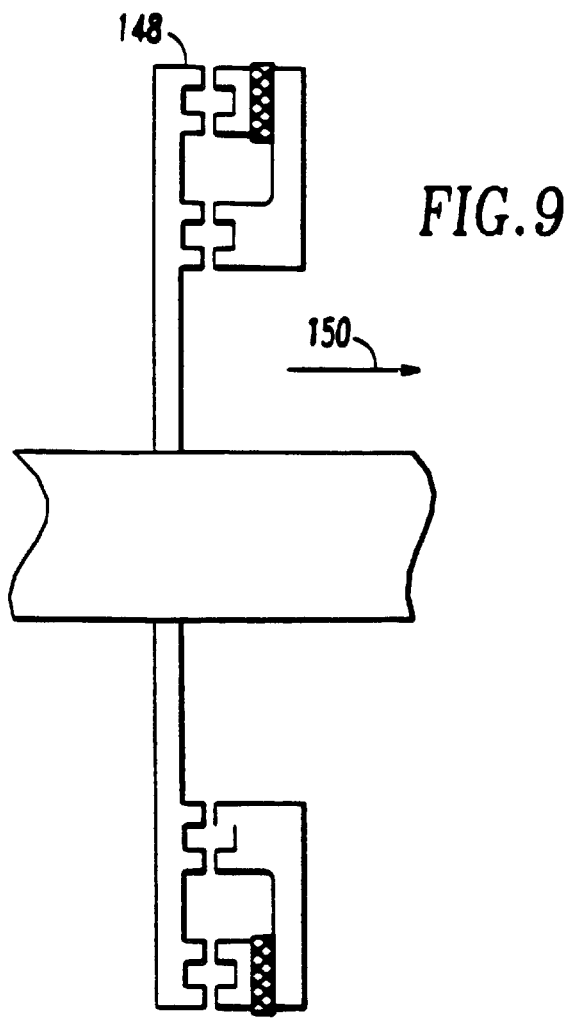
FIG. 9 is a cross-sectional view of another salient type passive radial bearing having a thrust bias which is equivalent to a passive radial bearing with axial offset.

FIG. 9 illustrates a passive radial half bearing (PRB2). This bearing is similar to that of FIG. 8 in that it provides radial position to the impeller 148, but unlike the PRB of FIG. 8 it provides a bias force on the impeller 148 in the direction 150.

Figure 10A:
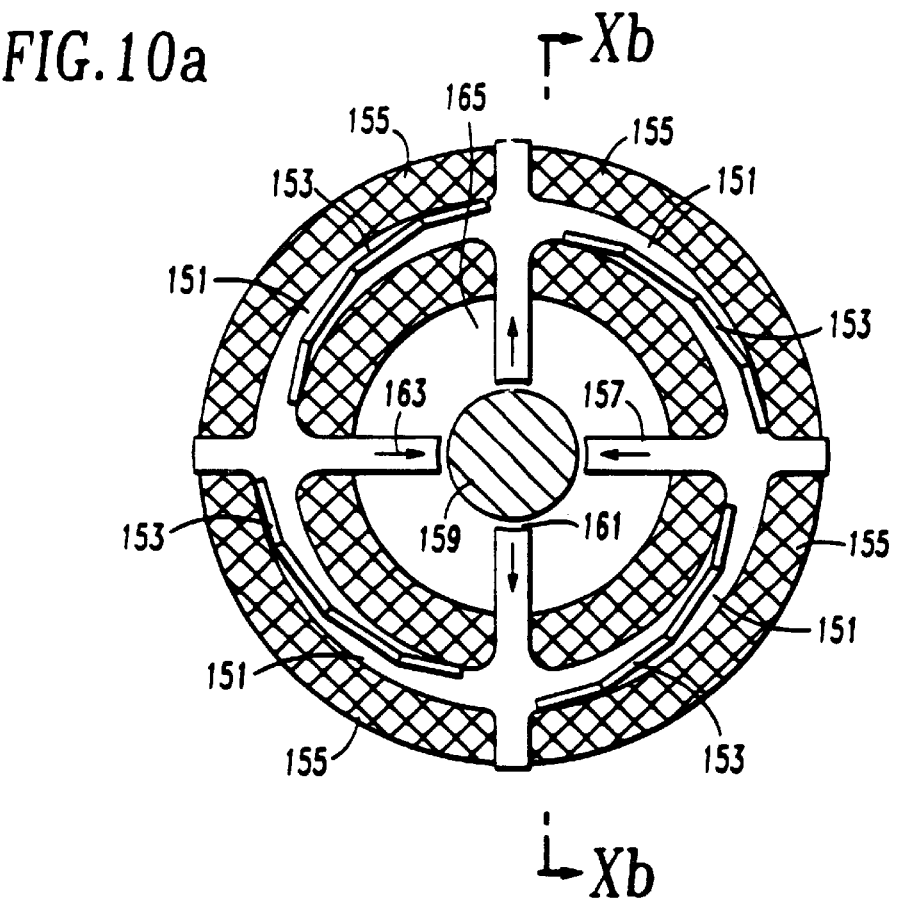
FIG. 10a is a cross-sectional view of an active radial bearing with large fluid flow regions.
Figure 10B:
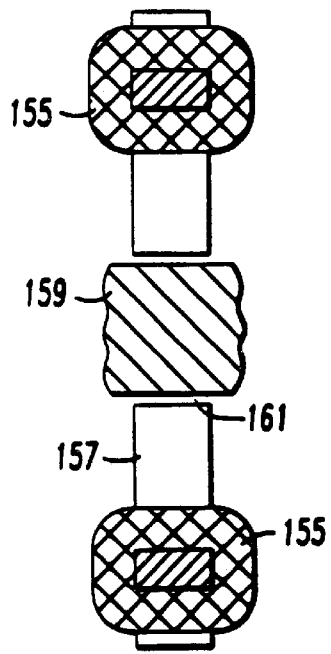
FIG. 10b is a cross-sectional view of the active radial bearing of FIG. 10a taken along line X—X.

Active Radial Bearing (ARB): FIGS. 10a and 10b depict an active radial bearing (ARB). The bearing stator consists of soft magnetic material backiron segments 151. segmented and radially magnetized permanent magnets 153, independently controlled coils 155 and four pole pieces 157. The rotor 159 is a soft magnetic material. The permanent magnets have magnetizations such that they provide a bias flux in the four gaps 161 between the rotor and the stator. The direction of this bias is shown with the four arrows 163. The stator coils are controlled to center the rotor around the stator. This design is particularly suited for use where fluid flow is required through the four bearing passages 165.

This bearing provides radial stiffness and essentially little axial stiffness when it is controlled with a feedback system and amplifier.

Figure 11:
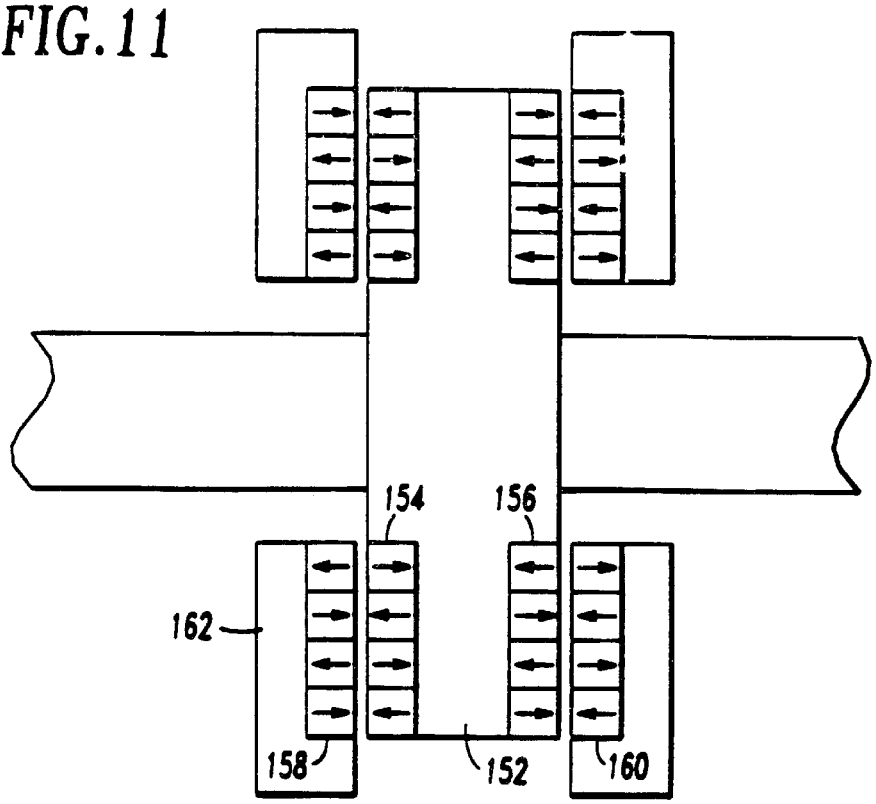
FIG. 11 is another view of a passive thrust bearing.

Passive Thrust Bearing (PTB) and Passive Thrust Half Bearing (PTB2): FIG. 11 illustrates a passive thrust bearing. The bearing rotor 152 supports two magnet stacks 154 and 156 which repel magnetstacks 158 and 160 on the stator 162. The net effect of the magnetic interaction is that the bearing has a positive axial stiffness and negative radial stiffness.

Figure 12:
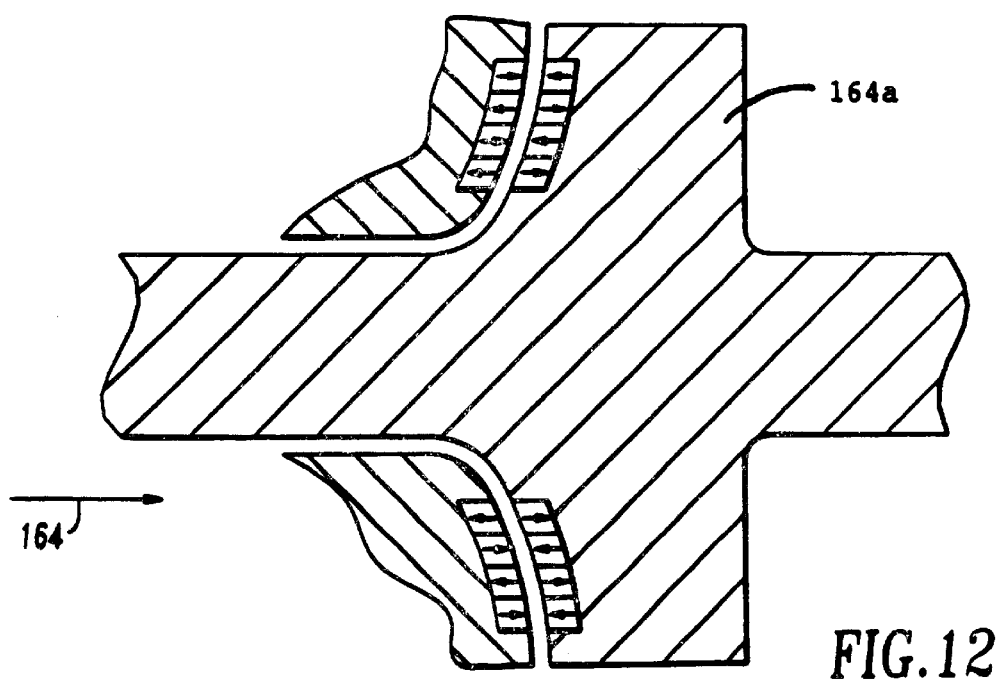
FIG. 12 is a cross-sectional view of a passive thrust half bearing wherein the two components are contoured to one another.

A similar bearing is shown in FIG. 12 which only applies thrust to the rotor 164a in the direction 164. Such a bearing is called a passive thrust half bearing (PTB2). All bearing gaps can be contoured to provide for blood flow without stagnant and separated flow.

Figure 13:
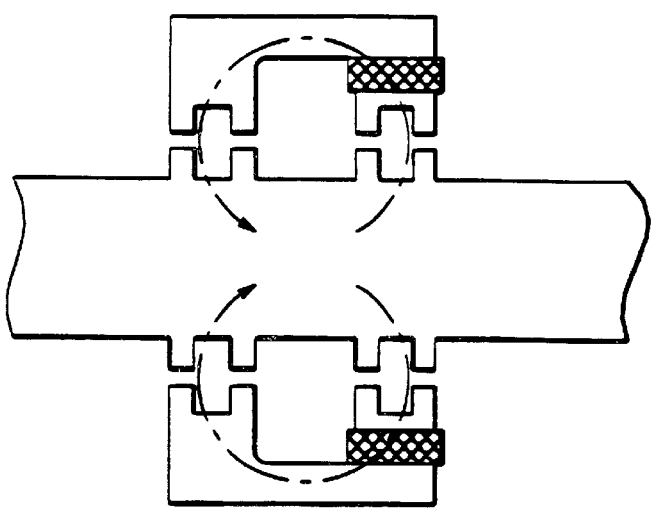
FIG. 13 is another passive thrust bearing where pole pieces are notched provide pole saliency.

FIG. 13 shows a thrust bearing which uses the same principles as the radial bearing of FIG. 8 but is distinguished from FIG. 8 in that the axial gaps of FIG. 8 are reoriented as radial gaps in FIG. 13.

Figure 14:
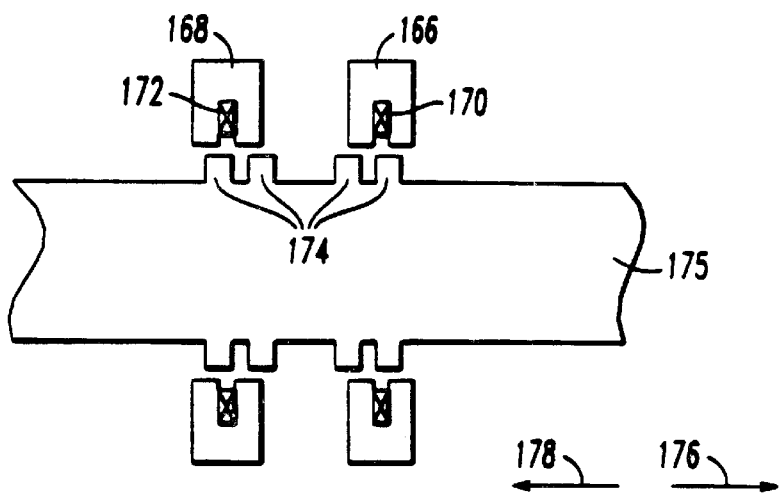
FIG. 14 is another active thrust bearing.
Figure 15:
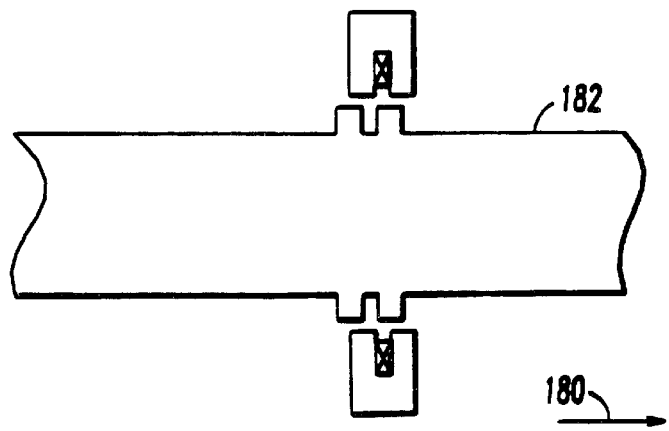
FIG. 15 is an active thrust half bearing.

Active Thrust Bearing (ATB) and Active Thrust Half Bearing (ATB2): FIG. 14 depicts an active thrust bearing. The stator consists of pole pieces 166 and 168 and coils 170 and 172 which are driven independently. Applying a current to coil 170 causes the stator pole piece 166 to line up with impeller teeth 174 by applying a force on the impeller 175 in the direction 176. Similarly, energizing coil 172 applies a force in the impeller 175 in the direction 178. By sensing that the axial position of the impeller 175. feedback controls can position the impeller 175 axially. These bearings exhibit moderate negative radial stiffness, and therefore require active control. FIG. 15 shows active thrust half bearing (ATB2) which only applies force in the direction 180 to the impeller 182.

Figures 16, 17:
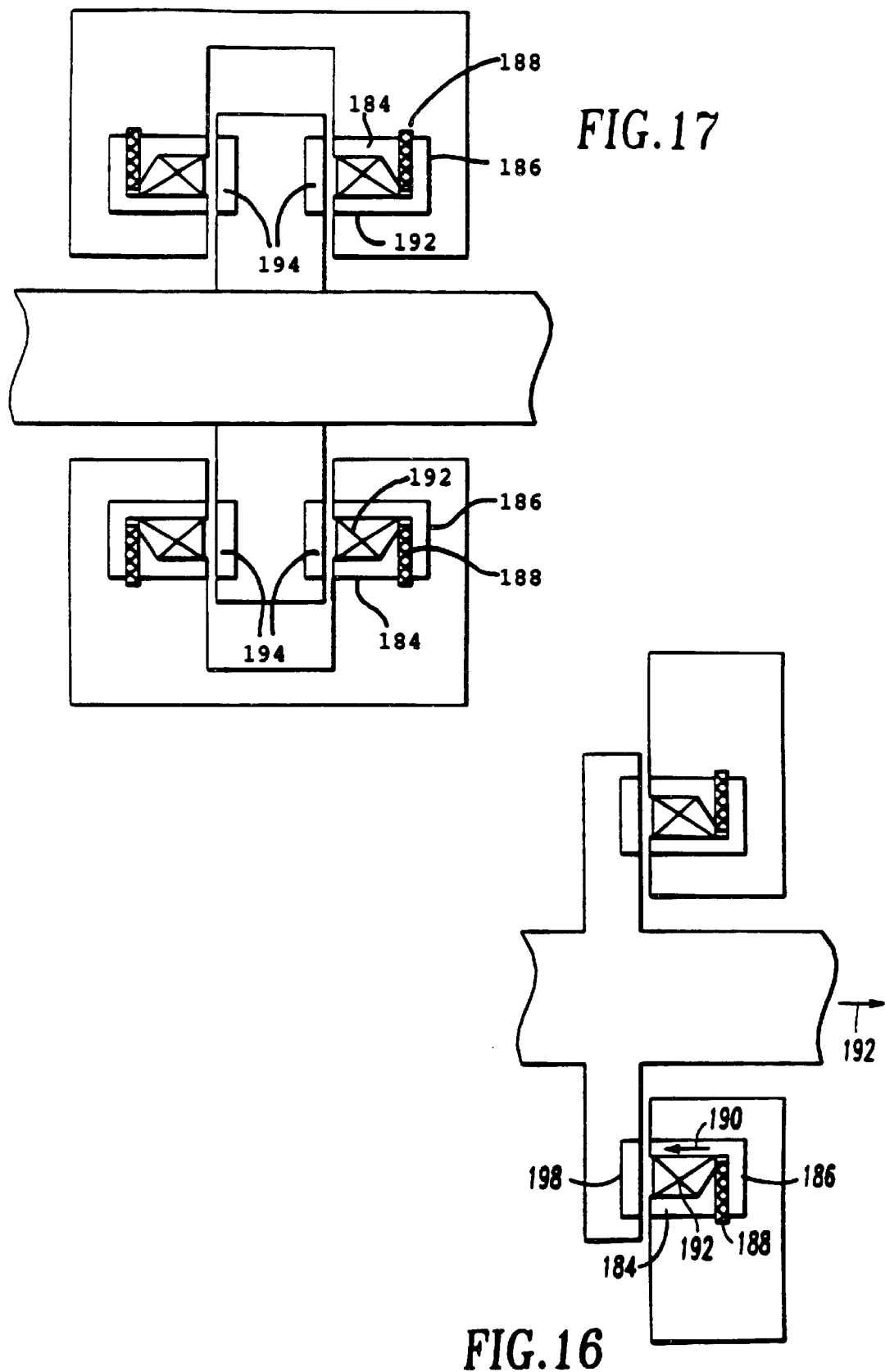
FIG. 16 is another active thrust half bearing.
FIG. 17 is a first embodiment of an active thrust bearing.

FIG. 16 illustrates an alternate active thrust half bearing. The stator consists of soft iron or ferromagnetic pieces 184 and 186 driven by a permanent biasing magnet 188 in the direction 190. The bias flux is modulated by the control coil 192, so that the force applied to the soft magnetic target 194 is controlled. This is an ATB2 because force is applied to the impeller only in the direction 198. FIG. 17 shows an ATB comprised of two ATB2's which are based on the same principles as FIG. 16.

Figure 17A:
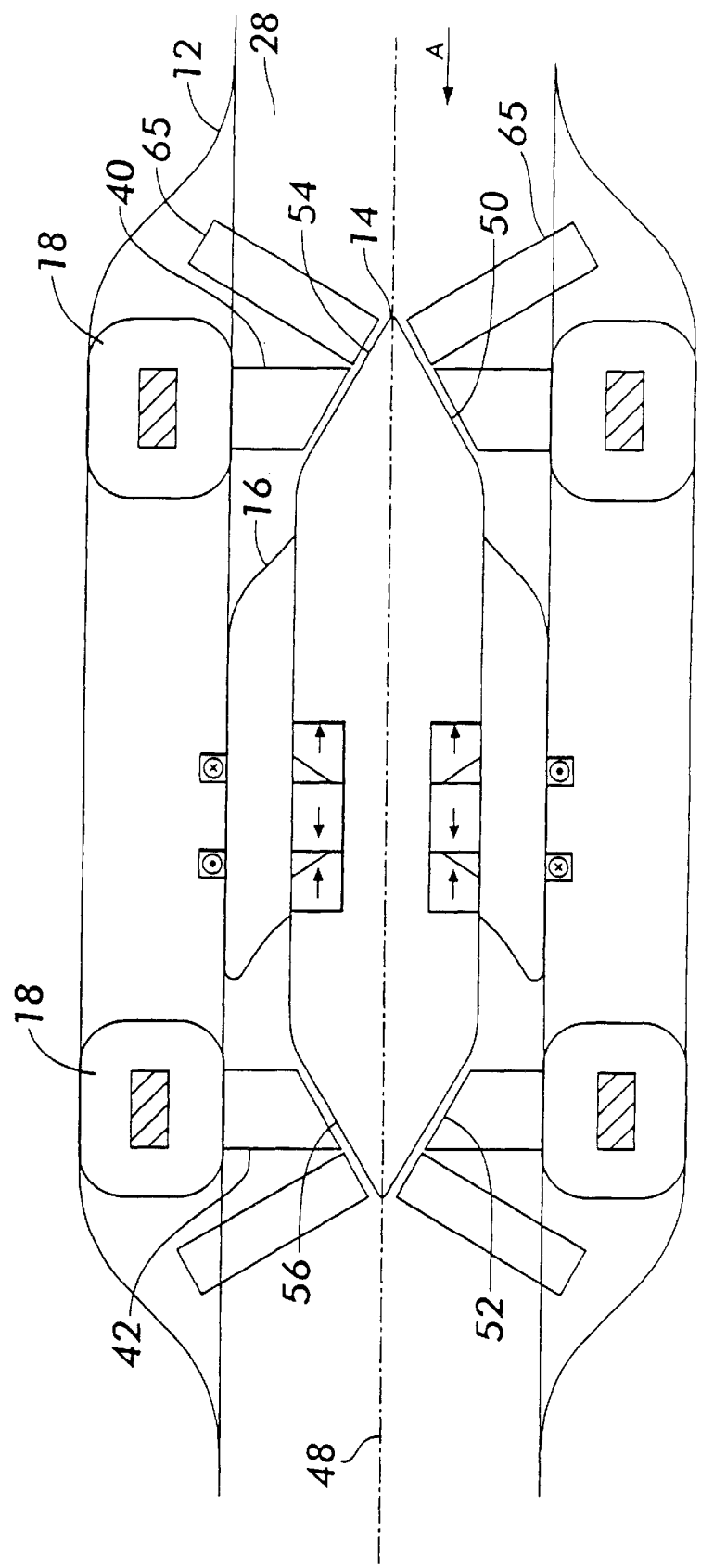
FIG. 17A is a second embodiment of an active thrust bearing.
Figure 17B:
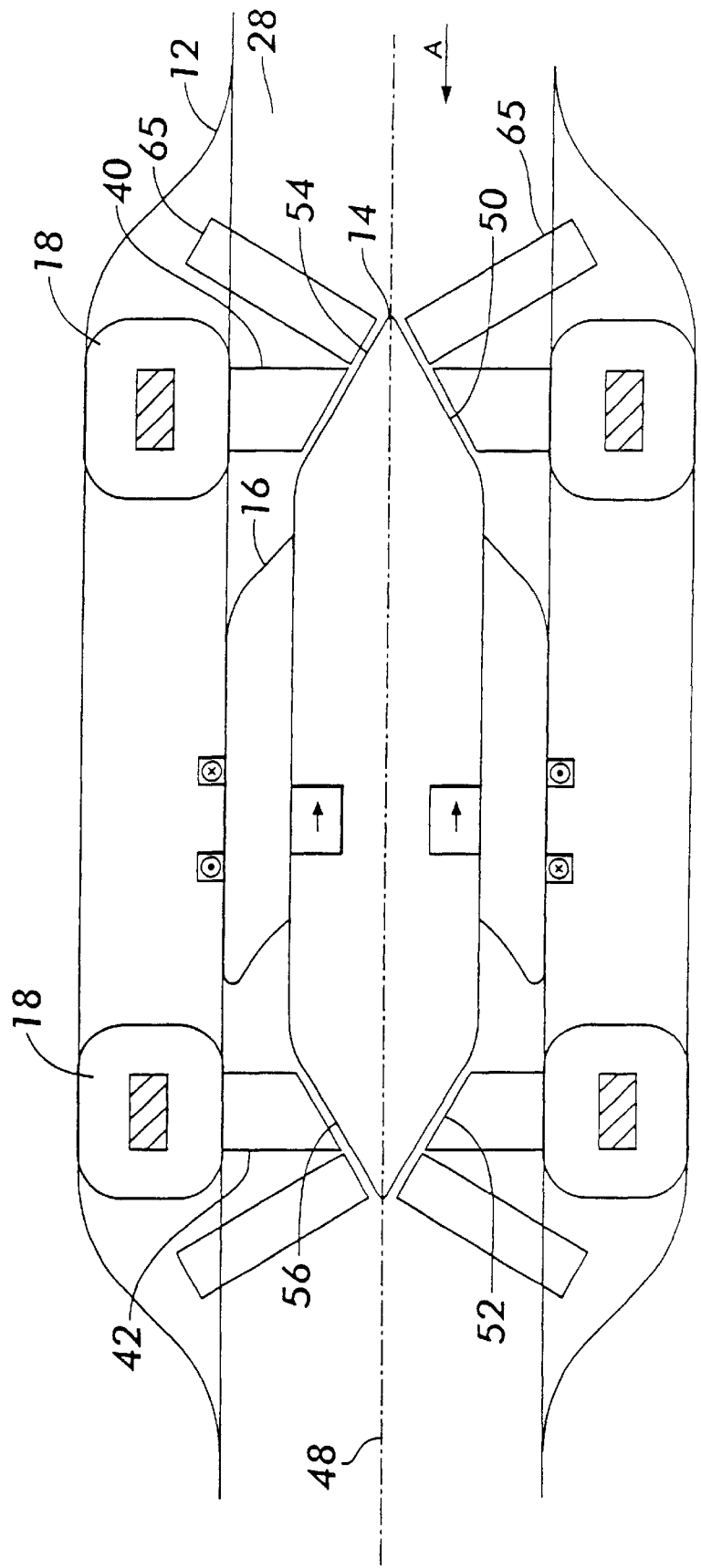
FIG. 17B is a third embodiment of an active thrust bearing.
Figure 17C:
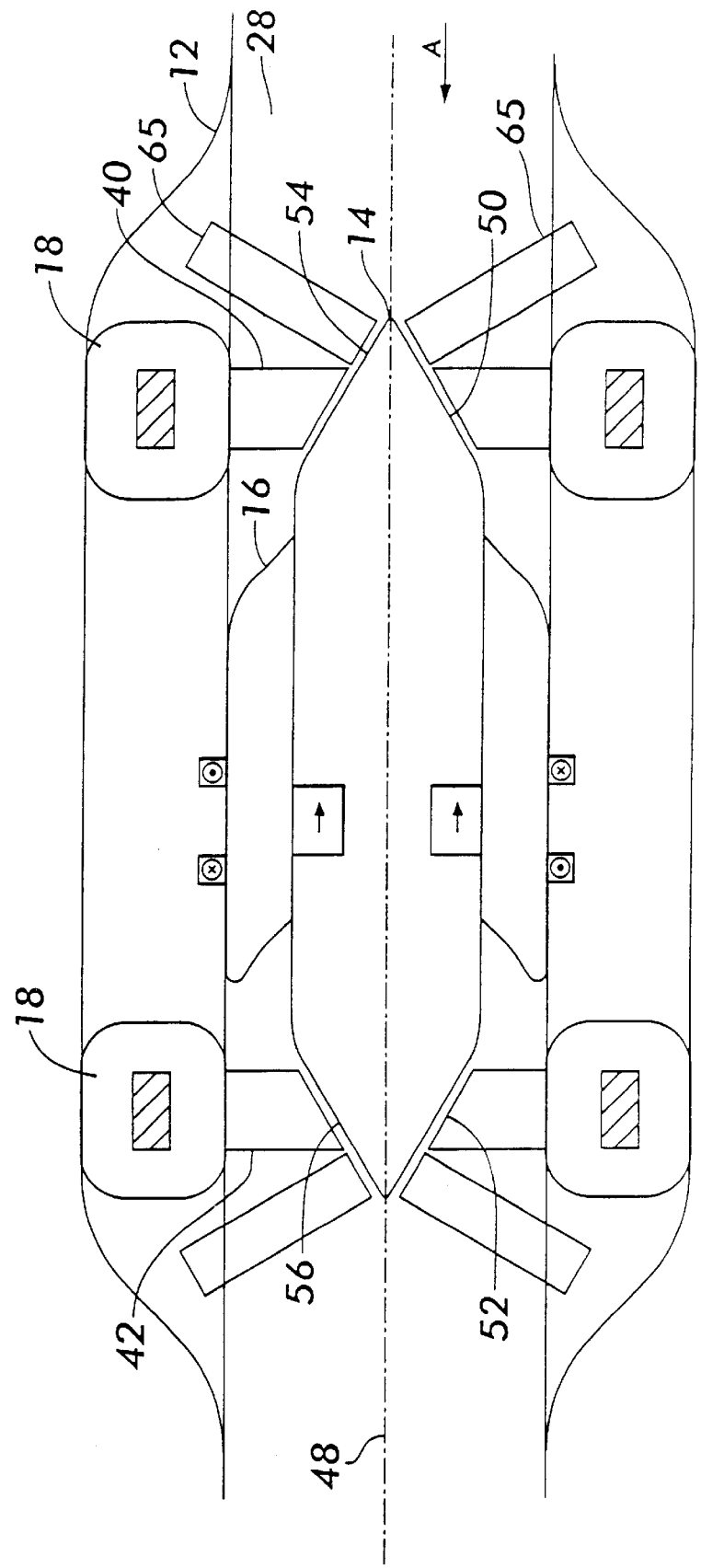
FIG. 17C is a fourth embodiment of an active thrust bearing.

FIGS. 17A–17C illustrate alternative types of active thrust bearings that may be used with the pump of this invention. Illustrated in these Figures are active thrust bearings that include Lorentz force actuators. As shown in FIG. 17A, a Lorentz force actuator includes coils 199a, preferably made of copper through which an electrical current flows. The magnetic field generated by these coils interacts with magnets 199d and pole pieces 199c disposed in the rotor to position the rotor axially. The currents in the two coils 199a are preferably equal and of opposite directions.

FIG. 17B illustrates another type of Lorentz force actuator in which the copper coils 199a interact with a single magnet 199b to control the axial position of the rotor. FIG. 17C depicts a third type of Lorentz force actuator that includes an outer iron member 199d, copper coils 199a and a single magnet 199b.

Figure 18:
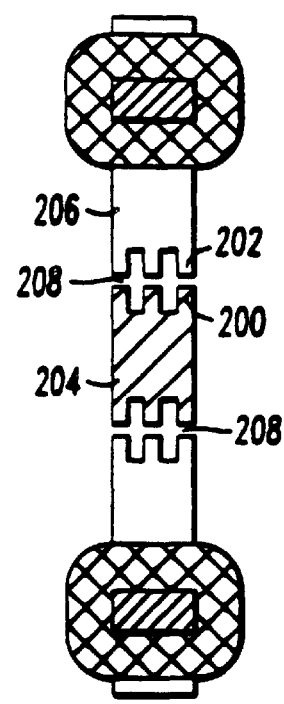
FIG. 18 is a hybrid of an active radial bearing and a passive thrust bearing.

Hybrid Components: It is often possible to physically integrate the function of two magnetic components. For example, FIG. 18 shows the ARB of FIGS. 10a and 10b with teeth 200 and 202 added to the rotor 204 and stator 206, respectively. The magnetic field across the gap 208 of the bearing cause the teeth 200 and 202 to align passively without feedback control hence this is a hybrid of a PTB and an ARB which is denoted as "PTB=ARB."

Figure 19:
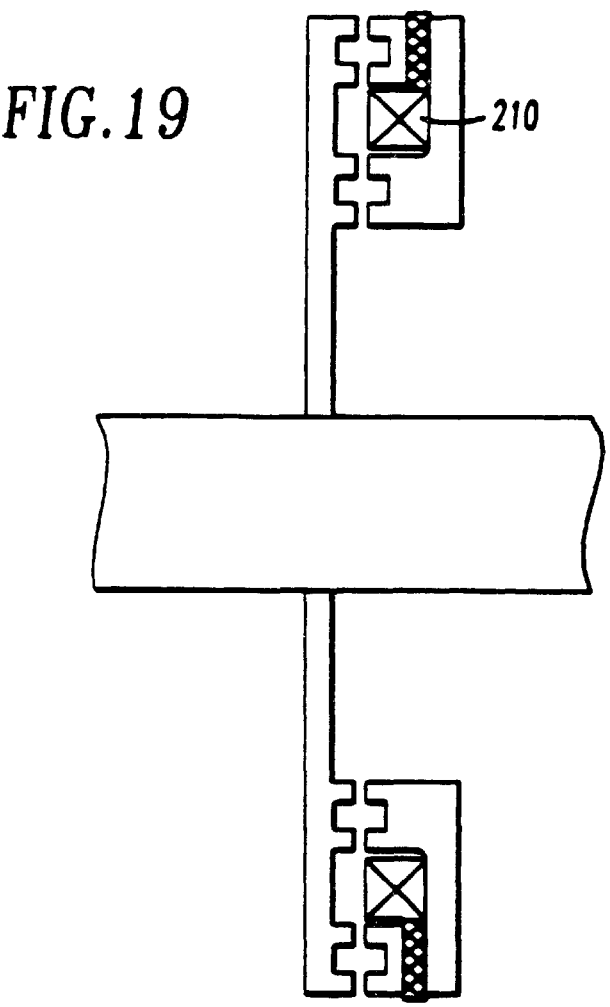
FIG. 19 is a hybrid of an active thrust half bearing and a passive radial bearing.

A similar hybrid is shown in FIG. 19. Coil 210 is added to a PPB which is half the PRB of FIG. 9. This coil actively controls thrust in one direction along the rotor axis. Because the function of an ATB2 is added to a PRB, the resulting hybrid is denoted as "ATB2=PRB."

The inlet-conical bearing in FIG. 1 is a hybrid of an active radial bearing and a thrust half-bearing because the pole face angles are intermediate between a thrust bearing and a radial bearing. The poles of the conical bearing also serve as pump stator blades.

Hybridization of fluid and magnetic components is also possible. Pump blades, both impeller and stator blades, can be used as magnetic flux paths. The stator blades in FIG. 1 act as magnetic poles for the conical magnetic bearings. Furthermore, the impeller blades are flux paths for the brushless DC motor in FIG. 1. It is also possible for stator blades to serve as supports for passive magnetic bearing stators, and for impeller blades to support magnetic structures.

Figure 20:
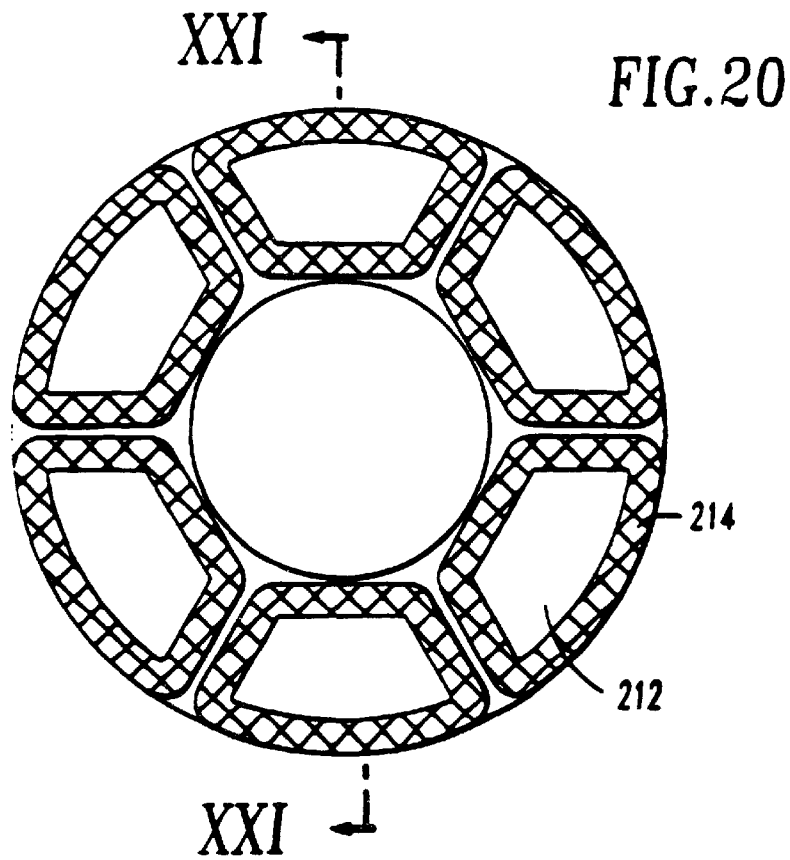
FIG. 20 is a hybrid of a stator of an induction motor and an active thrust half bearing.
Figure 21:
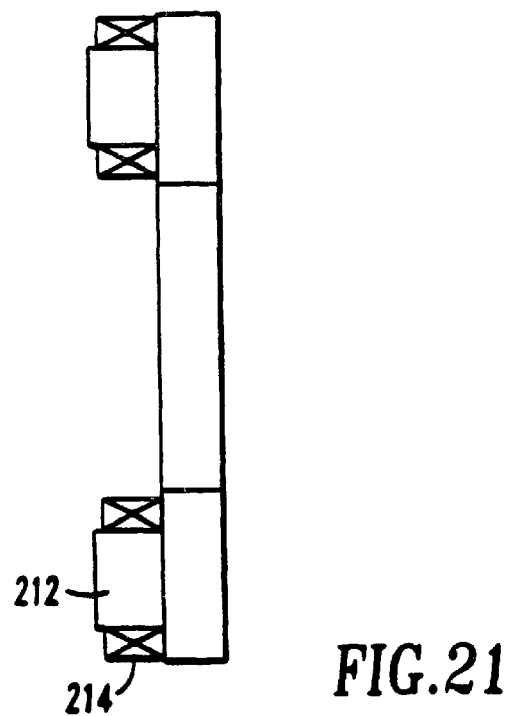
FIG. 21 is a cross-section of the stator shown in FIG. 20 taken along the line XXI—XXI.
Figure 22:
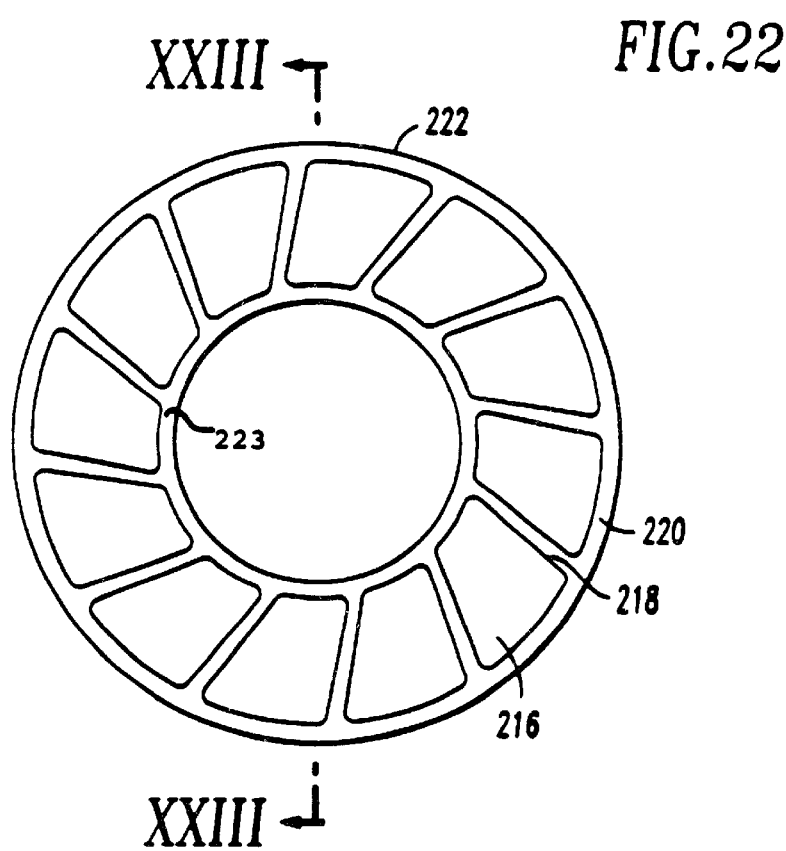
FIG. 22 is an armature of a hybrid of an induction motor and an active half thrust bearing.
Figure 23:
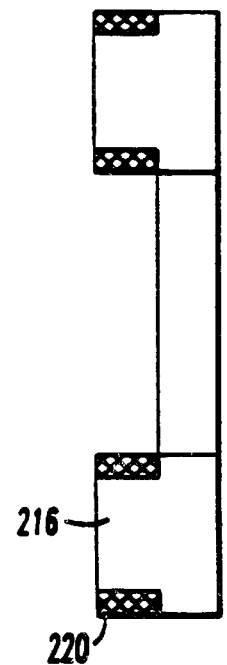
FIG. 23 is a cross-section of the armature shown in FIG. 22 taken along line XXIII—XXIII.

FIGS. 20 through 23 illustrate a pancake induction motor which can be controlled for thrust as well. FIGS. 20 and 21 show a stator with stator poles 212 and stator coils 214 for a pancake induction motor. FIGS. 22 and 23 show an armature 222 with magnetic iron members 216 and slot conductors 218. Annular regions 220 and 223 are also conductors. By controlling the six stator coil currents it is possible to simultaneously vary the motor torque and thrust forces across the pancake motor. This can be done by varying the rotational frequency of the stator field and the amplitude of the stator field independently. Similar hybridization of a variable reluctance type motor is described in U.S. Pat. No. 4,683,391.

An alternative embodiment of the motor to be used as rotation means is the two pole type brushless DC motor 224a shown in FIG. 24. The rotor 224b is shown along with the stator. The stator coils are not shown in FIG. 24, but are similar to those of FIG. 3.

Alternative Means of Rotation: An alternative motor configuration for FIG. 1 is shown in FIG. 25. This is a variable reluctance type motor where the rotor poles and the impeller blades are hybridized. The rotor 224 is made from a soft magnetic material as are the blades 226. The commutation for this motor is different from that for the DC brushless motor, but well known to those skilled in the art of motor control.

Figure 26:
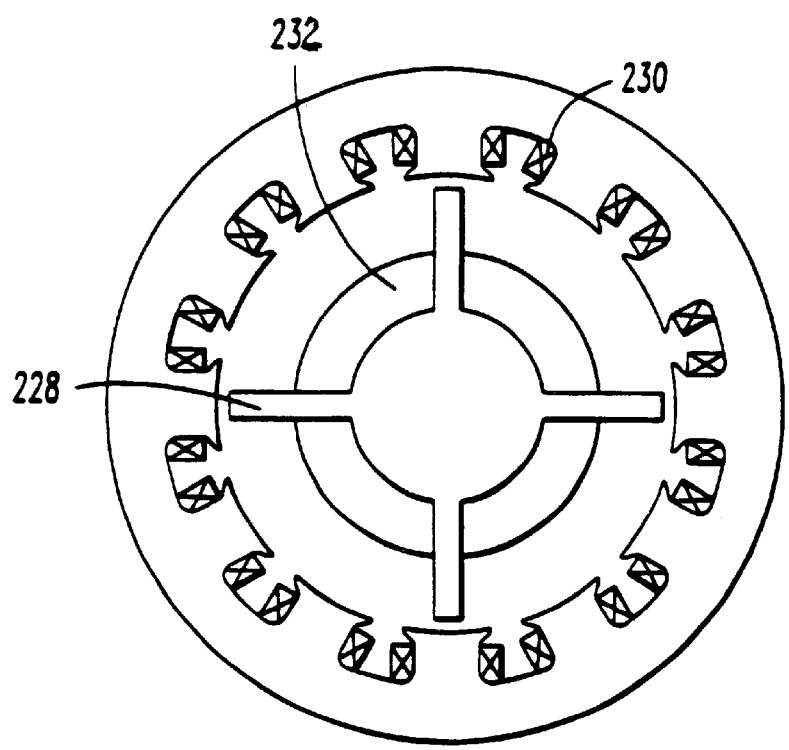
FIG. 26 is a cross-sectional view of an induction motor hybridized with impeller blades.

FIG. 26 is yet another possible motor configuration to be used in the rotary pump shown in FIG. 1. It is an induction motor whose impeller slot structure is hybridized with the impeller blades 228. By applying a rotating magnetic field to the impeller via the stator coils 230, currents are induced in the slot conductors 232 which have current return paths connecting adjacent slots conductors, that are not shown, but exist on the axial end caps of the impeller.

Figure 27:
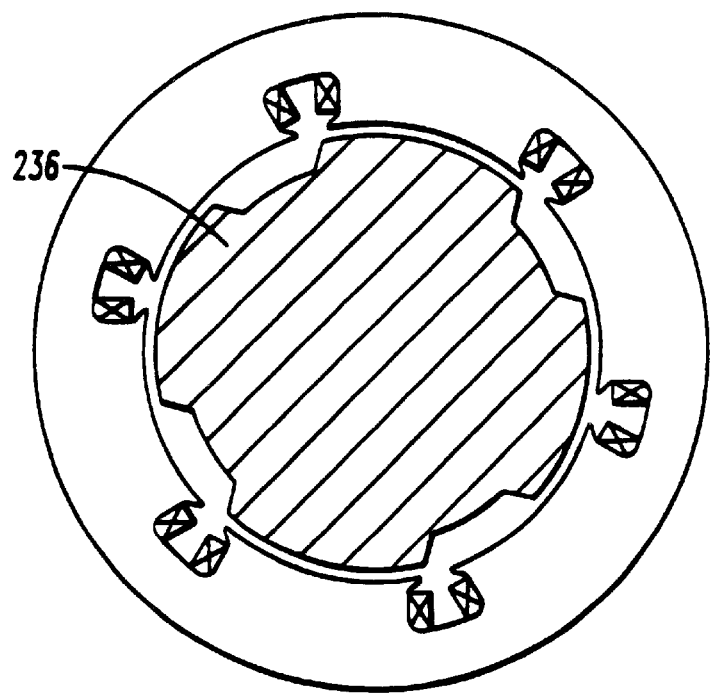
FIG. 27 is a cross-sectional view of another variable reluctance motor.

FIG. 27 depicts a variable reluctance motor cross section to be used in the rotary pump of the present preferred invention. The impeller of this motor 236 is made from soft magnetic material (e.g. approximately 3% silicon-iron).

Figure 28:
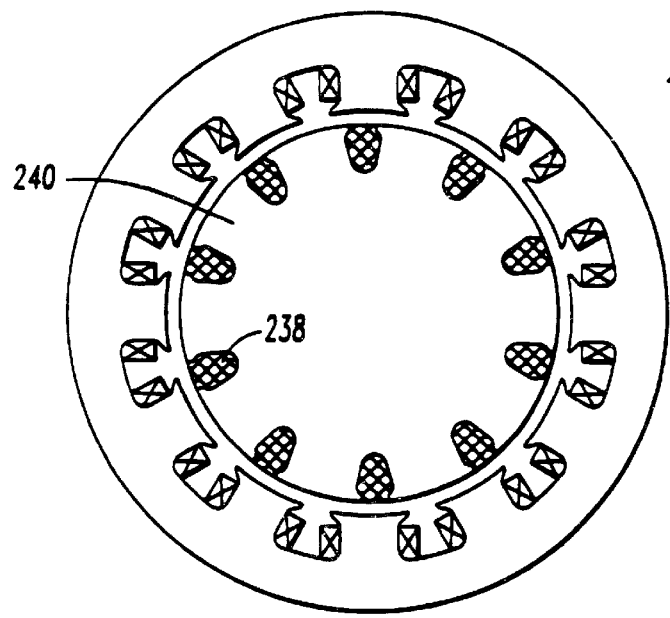
FIG. 28 is a cross-sectional view of another induction motor.

FIG. 28 is an induction motor. The cross-section of the motor depicts slot conductors 238 and a soft magnetic material impeller 240. Slot conductor end-turn current paths are not shown.

The following acronyms can be utilized to describe various configurations for the rotation means and the levitation means of the present preferred invention.

Pump Type Descriptors
FH fixed hub
RH rotating hub
AO axial outlet
RO Radial outlet
Sp fixed-hub support
sb stator blade
ib impeller blade
Magnetic Components
ARB active radial bearing
ATB active thrust bearing
ATB2 active thrust half-bearing
PRB passive radial bearing
PRB2 passive thrust half bearing
VRM variable reluctance motor
DCBM direct current brushless motor
IM induction motor
Other Notations
x is used to indicate a magnetic component X, where the magnetic gap is positioned adjacent the housing
x̲ is used to indicate a magnetic component X, where the magnetic gap is adjacent the hub.
— a line segment indicates that two components are consecutive along the blood flow path.
= an equal sign indicates that two components are functionally integrated or "hybridized."

is used to indicate that the component X is hybridized with impeller blades.

is used to indicate that the component X is hybridized with stator blades.

indicates components X and Y are aligned for structural support.
(RH, AO) parenthetical acronyms denote the design type. In this case "rotating hub with axial outlet."
With these notations we can represent the pump in FIG. 1 by the following formula.

$$\text{(RH, AO)} \quad \underset{\text{sb-}}{\text{ATB2}} = \underset{\text{ib-}}{\text{ARB-DCBM-}\underline{\text{ARB}}} = \underset{\text{sb}}{\text{ATB2}} \quad (1)$$

Each formula consists of a "header" defining the hub type (RH or FH) and the outlet type (AO or RO), followed by an "upper sentence" describing the order and kinds of magnetic components, gap locations either at the housing or hub and whether or not they are hybridized. Positions of hub supports are also noted in the upper sentence. There is also a "lower sentence" describing the order of fluid components vertical alignment between the upper sentence and the lower sentence does not imply any physical alignment unless a """ is used to indicate alignment or a "||" is used to indicate that components in the two sentences are hybridized.

Formula (1) describes a design which is a rotary hub type (RH) with axial outlet (AO). The components from inlet to outlet along the blood flow path are a stator blade hybridized with an active radial half bearing which forms a conical bearing and the hybridized bearing has its magnetic gap toward the inside diameter of the primary fluid flow path. Reading formula 1 further, a brushless DC motor is hybridized with the impeller blades and has its magnetic gap toward the outside diameter of the fluid flow path. Reading formula 1 further, an active radial bearing is hybridized with an active thrust half bearing which is further hybridized with a set of stator blades.

Using this language many of the embodiments of the rotary pump of the present preferred invention are enumerated. By applying physical constraints, designs are eliminated which are not practical.

A formula header is any one of (FH, AO), (FH, RO), (RH, AO), or (RH, RO). A formula upper sentence is any sequence of magnetic components acronyms and/or support acronyms separated by "—" or "=". The magnetic component acronyms are either underlined or not. The lower sentence is any sequence of impeller blade acronyms or stator blade acronyms. Each acronym in the lower sentence may be aligned with one acronym in upper sentence provided that order is preserved; that is, if an acronym identifying a magnetic component (A) and an acronym denoting a fluid component (B) are aligned with a "|" or hybridized with "||", and an acronym denoting a magnetic component (C) and an acronym denoting a fluid component (D) are aligned, and if C follows A in the upper sentence we must have D following B in the lower sentence we call this the "order preserving" property.

Certain formulas can be eliminated because they violate the following simple structural requirements. All formulas with the header (RH, RO) are eliminated due to the existence of a stagnation zone in this configuration. If the bearing is RH type then Sp may not appear in the upper sentence because supports are only needed for the fixed hub (FH) type pump. No two magnetic components may be separated by a fixed hub support (Sp). If this were to happen the impeller would be divided into two separate pieces. The lower sentence must include at least one impeller blade (ib). if the header contains a fixed hub (FH), then the upper sentence must contain at least one support (Sp). The upper sentence must include one motor; however, we may have additional motors to add reliability. The magnetic components must satisfy force/moment balance for x, y, z, pitch ($\Theta$) and yaw ($\phi$) motions of the impeller. That is, any bias force associated with PRB offsets or ATB2's must balance.

Collectively the magnetic bearing components, both active and passive must provide positive stiffness (i.e., positive restoring forces to levitation) in the x, y, z, pitch and yaw directions because the motor controls the roll direction. This is characterized mathematically with a positive definite symmetric stiffness matrix, K, relating the five displacements, x, y, z, pitch and yaw to the corresponding restoring forces and moments. Consider a coordinate frame at the center of mass of the rotor with its axes aligned as shown in FIG. 1. Pitch is rotation about the x-axis; yaw is rotation about the z axis; and roll is rotation about the y-axis and is controlled by the motor. Let $(\Delta x, \Delta y, \Delta z, \Delta \theta, \Delta \phi)^T$ be the vector of x, y, z, pitch and yaw displacements of the impeller relative to the desired levitated position, where superscript "T" denotes transpose. Further, let the vector of corresponding forces and moments measured in the given frame be $(f_x, f_y, f_z, m_\theta, m_\phi)^T$ and let K be the "support stiffness matrix" of the rotor satisfying $(f_x, f_y, f_z, m_\theta, m_\phi)^T = -K(\Delta x, \Delta y, \Delta z, \Delta \theta, \Delta \phi)^T$. By using appropriate feedback control of active magnetic bearings, the axial position of the rotor can be maintained. This can be achieved by using a particular candidate magnetic bearing configuration that has a positive definite symmetric support stiffness matrix. (positive definite means that for all vectors a variable $v \neq 0$, $v^T Kv > 0$). With feedback control this stiffness property can be achieved only over a certain frequency band.

If such a support stiffness matrix is achievable for a particular set and placement of magnetic bearings, we say that the magnetic bearings are "compatible." This definition of compatibility allows us to enumerate a large number of good designs via computer verification of the positive definiteness of the support stiffness matrix.

Using the enumeration methodology outlined above we can derive additional embodiments of the present preferred invention. Alternative embodiments are:

$$\text{(FH,AO)} \quad \underset{\text{sb}}{\text{Sp-}\underline{\text{PRB}}\text{-ATB2-}\underline{\text{PRB}}\text{-}\underset{\text{ib-}}{\text{DCBM-Sp}}}\underset{\text{sb}}{} \quad (2)$$

$$\text{(FH,AO)} \quad \underset{\text{sb-}}{\text{Sp-}\underline{\text{PRB}}\text{-DCBM-}}\underset{\text{ib-}}{\text{ATB2}}\text{=}\underset{\text{sb}}{\underline{\text{ARB}}\text{-Sp}} \quad (3)$$

$$\text{(FH,RO)} \quad \underline{\text{PRB}}\text{-DCBM-}\underline{\text{PRB}}\text{-ATB2-Sp} \quad (4)$$
$$\text{ib}$$

Additional good embodiments have the following formulas.

Having isolated thrust bearing:

$$\text{(FH,AO)} \quad \underset{\text{sb-}}{\text{Sp-}\underline{\text{PRB}}\text{-DCBM-}}\underset{\text{ib-}}{\underline{\text{PRB}}\text{-ATB2-Sp}}\underset{\text{sb}}{} \quad (5)$$

$$\text{(FH,AO)} \quad \underset{\text{sb-}}{\text{Sp-}\underline{\text{PRB}}\text{-DCBM-}}\underset{\text{ib-}}{\underline{\text{ARB}}\text{-ATB2-Sp}}\underset{\text{sb}}{} \quad (6)$$

$$\text{(FH,AO)} \quad \underset{\text{sb-}}{\text{Sp-}\underline{\text{ARB}}\text{-DCBM-}}\underset{\text{ib-}}{\underline{\text{PRB}}\text{-ATB2-Sp}}\underset{\text{sb}}{} \quad (7)$$

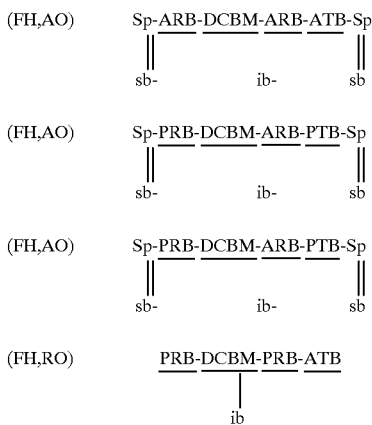

Having outboard motor:

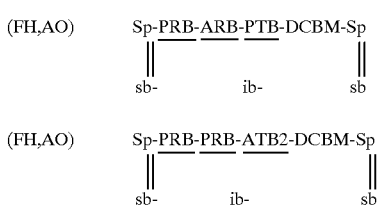

The geometric configurations of the impeller and stator member are crucial to the hydrodynamic performance and the biocompatibility of the rotary pump. Specifically, the flow path must be designed to avoid regions of high fluid stress which may damage cells or activate the clotting process. Further, regions of blood stagnation that may result in depositions of blood elements on the blood pump structure should also be avoided because they may cause embolism and possibly stroke. A computational fluid dynamics method is employed to design the geometric configurations of the impeller, stator member, and the housing which takes into consideration the specific characteristics of blood flow such as the tendency of blood to clot when regions of stagnation develop, and the propensity of blood cells to rupture when excessive stress is placed thereon.

Figure 29:
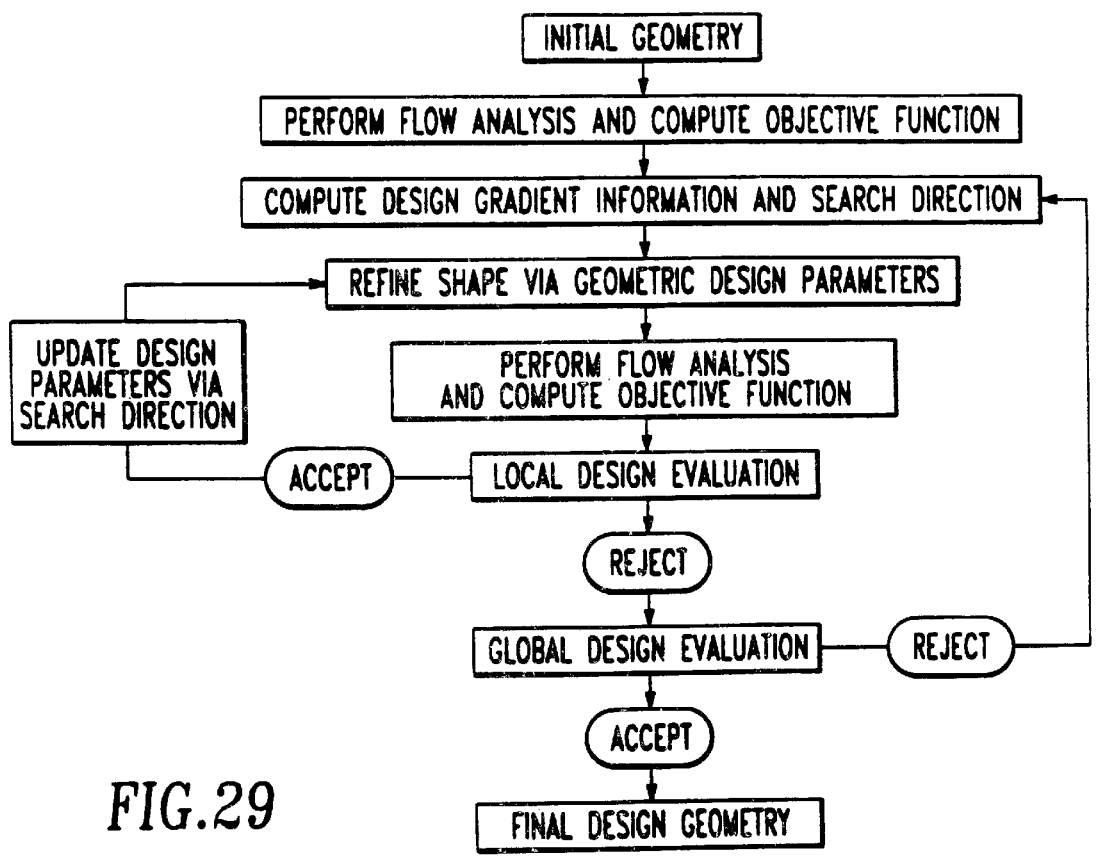
FIG. 29 is a flow chart illustrating a computational fluid dynamics method used to design the geometric configuration of the embodiments of the present preferred invention.

In FIG. 29 illustrates a flow chart describing the computational fluid dynamics-based method used to design the geometric configurations of the present preferred invention. This method for designing a rotary fluid pump substantially comprises the steps of: (a) selecting an initial geometric configuration of a part of a rotary fluid pump; (b) converting the geometric configuration into parametric form; (c) selecting a fluid dynamic model for blood flow; (d) choosing an objective function to be minimized; (e) determining the flow solution and value of the objective function for the initial geometric configuration; (f) determining the design search direction for the initial geometric configuration which is based on gradients of the objective function with respect to design variables; (g) selecting a second geometric configuration of the part of the fluid pump being designed by changing the geometric design parameters using the search direction information; (h) determining the flow solution and value of objective function for the second geometric configuration; (i) comparing the objective function for the first geometric configuration with the objective function for the second geometric configuration; (j) if the objective function for the second geometric configuration is less than the objective function for the first geometric configuration, the second geometric configuration becomes the initial geometric configuration and steps (g) through (j) should be performed until the objective function for the second geometric configuration is greater than the objective function for the initial geometric configuration, and the global design criterial should then be evaluated; (k) if the global design criteria indicates that further design improvement may be possible, the second geometric configuration becomes the initial geometric configuration and steps (f) through (k) should be performed until no further design improvement is deemed possible; alternatively, the initial design configuration is taken to represent the final design configuration. The final geometric configuration defines the shape of the part of the rotary pump that minimizes stagnant and traumatic flow through the pump. This method can be used to define one or all of the various parts of a rotary pump such as, the impeller blades, the impeller hub, the stator blades, the stator hub and the housing interior surface. Other aspects of this method are described in Gregory W. Burgreen, et a., *CFD-Based Design Optimization of a Three Dimensional Rotary Blood Pump*, AIAA Paper No. 96-4185, 1773–1779 (1996), presented at the 6th ALAA/NASA/ISSMO "Symposium on Multidisciplinary Analysis And Optimization" in Bellevue, Wash. which is hereby incorporated by reference.

The model for the blood flow is preferably the incompressible Navier-Stokes and conservation of mass equations. Use of the former equations assumes that blood can be treated as a single phase homogenous linear viscous fluid. In order to solve this equation, a Galerkin finite-element program was written for this purpose. This program uses quadratic velocity-linear pressure elements within a mixed formulation of the steady equations. These element types are known to be stable and produce approximations of optimal order. The resulting, non-linear algebraic system is solved by a Newton continuation method. Analytical gradients of the objective functions are computed using a direct differentiation method.

The objective function used in the above-method represents the desired design criterion to be minimized. For example, the objective functions relating to trauma and platelet activation include, but are not limited to: shear stress with respect to resident time, viscous energy dissipation rates, particle acceleration, negative pressure causing outgassing or cavitation, and measurements of turbulence intensities. The objective functions defining stagnation and deposition include but are not limited to: vorticity, reverse flow (i.e., boundary layer shear locally becoming zero), adverse pressure gradient, the standard deviation of consecutive blade-to-blade axial velocity, and boundary layer transport. This list is illustrative but is not exhaustive to the objective functions that can be utilized in the present preferred method of designing geometric configurations for the rotary pump of the present preferred invention.

Figure 30:
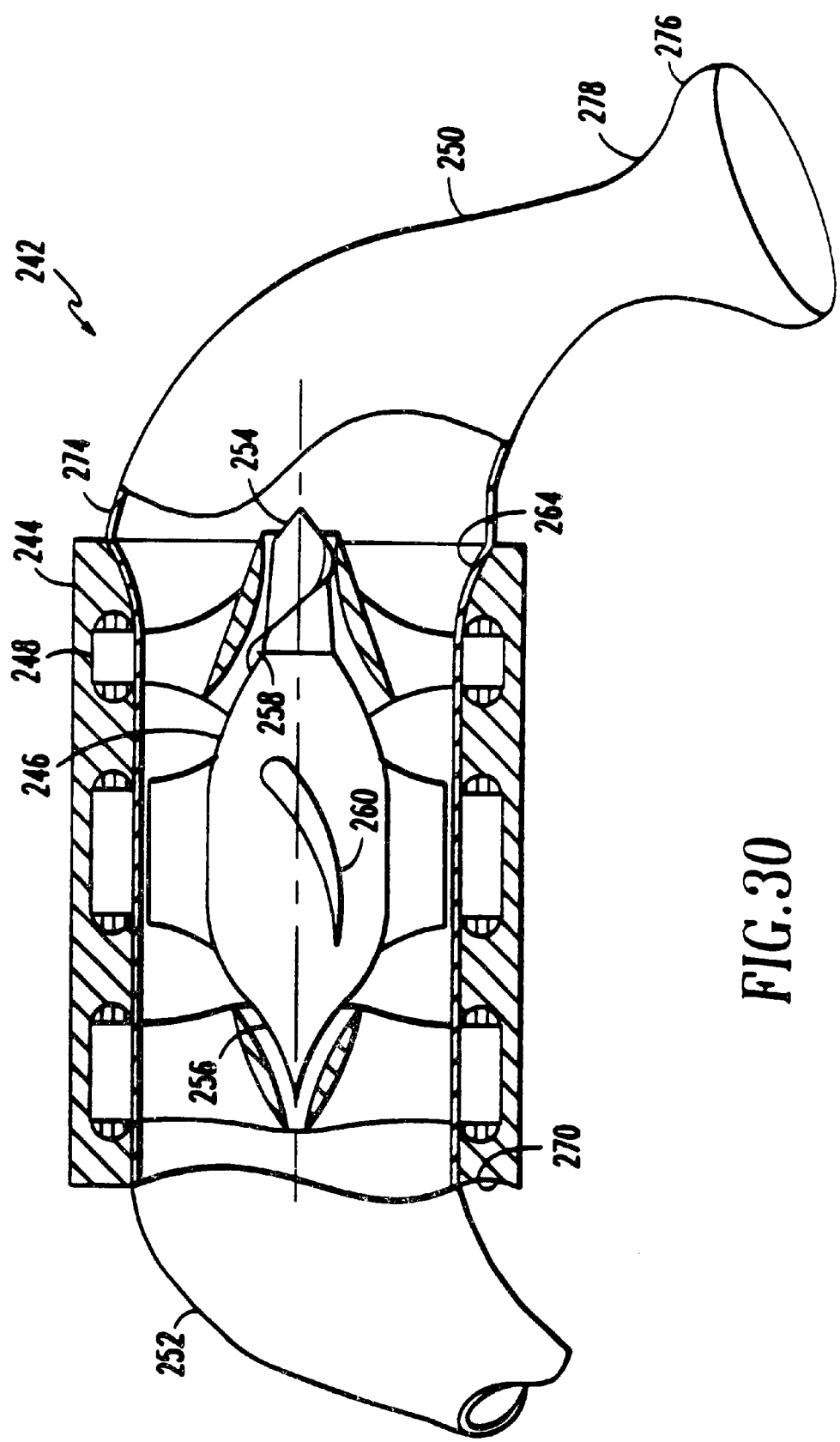
FIG. 30 is a partial cutaway cross-sectional view an alternate embodiment of the rotary fluid pump of the present prefigured invention having an inducer blade positioned on the impeller and an inflow cannula and an outflow cannula positioned at the inlet and outlet of the housing, respectively.

FIG. 30 illustrates another embodiment of the present preferred invention which is similar to the rotary pump 10 shown in FIGS. 1 through 5 and can be represented by Formula (1) described above. For purposes of brevity, only the differences between the two rotary pumps will be described. The rotary pump 242 substantially comprises a housing 244, an impeller 246 positioned within the housing 244, a stator member 248; an inflow cannula 250, and an outflow cannula 252, means for levitating the impeller 246 within the housing 244, and means for rotating the impeller 246. The impeller 246 has a nose 254, a tail 256, and an inducer blade 258 positioned on the nose 254 of the impeller 246. The inducer blade 258 extends around the surface of the impeller nose 254. The inducer blade 258, as well as the impeller blades 260 preferably are substantially helical in shape. The inducer blade 258 functions to augment the blood flow through the housing 244 while decreasing cavitation susceptibility. The inflow cannula 250 is attached to the inlet 264 of the housing 244 and the outflow cannula 252 is attached to the outlet 270 of the housing 244. The inflow cannula 250 is a conduit with a first end 274 and a second end 276. The first end 274 is attached to the housing inlet 264 and the second end 276 is capable of being attached to the left ventricle of a heart. The second end 276 has a trumpet mouth inlet nozzle 278 with an hourglass exterior configuration. Preferably, the inner diameter of the nozzle 278 tapers from twenty millimeters (20 mm) to a final conduit diameter of twelve millimeters (12 mm). Although both the inflow cannula 250 and the outflow cannula 252 are shown to be integrated into the housing 244 of the rotary pump 242, it is also possible to have cannula employing quick-connecting mechanisms (not shown) in such that the rotary pump can be quickly detached from the patient.

The stator member 248, the means for rotating the impeller 246 and the means for levitating the impeller function substantially the same as those described in FIGS. 1 through 5. It should also be noted that the rotary pump 242 does not utilize any position sensors as compared to the rotary pump 10, shown in FIGS. 1 through 5, which includes position sensors 65. A sensorless approach, based on back EMF or coil inductance variation is used in this embodiment to measure magnetic bearing gaps and impeller angle. Because there are coils in the motor stator and the magnetic bearing stators, voltages induced by impeller motions and self-induced by coil currents can be used to calculate the impeller angle and the magnetic bearing gaps. Examples of methods of sensorless magnetic bearings and sensorless motor control are described in: "A New Approach To Sensorless and Voltage Controlled AMBs Based on Network Theory Concepts," D. Vischer et al., 2nd International Conference on Magnetic Bearings, Tokyo, pp. 301–309, July, 1990; "Sensorless Magnetic Levitation Control by Measuring the PWM Carrier Frequency Content," Y. Okado, et al., Proceedings of the Third International Symposium on Magnetic Bearings, Alexandria, pp. 176–186, July 1992; "Implementation of Sensorless Control of Radial Magnetic Bearings," R. Gurumoorthy, et al., Proceedings of MAG '95, Alexandria, pp. 239–248, August 1994; and U.S. Pat. No. 5,300,841 issued to M. A. S. Preston et al., for sensorless DC motor control, see the data sheet from Micro Linear Corporation's ML4425 integrated circuit.

Figure 31:
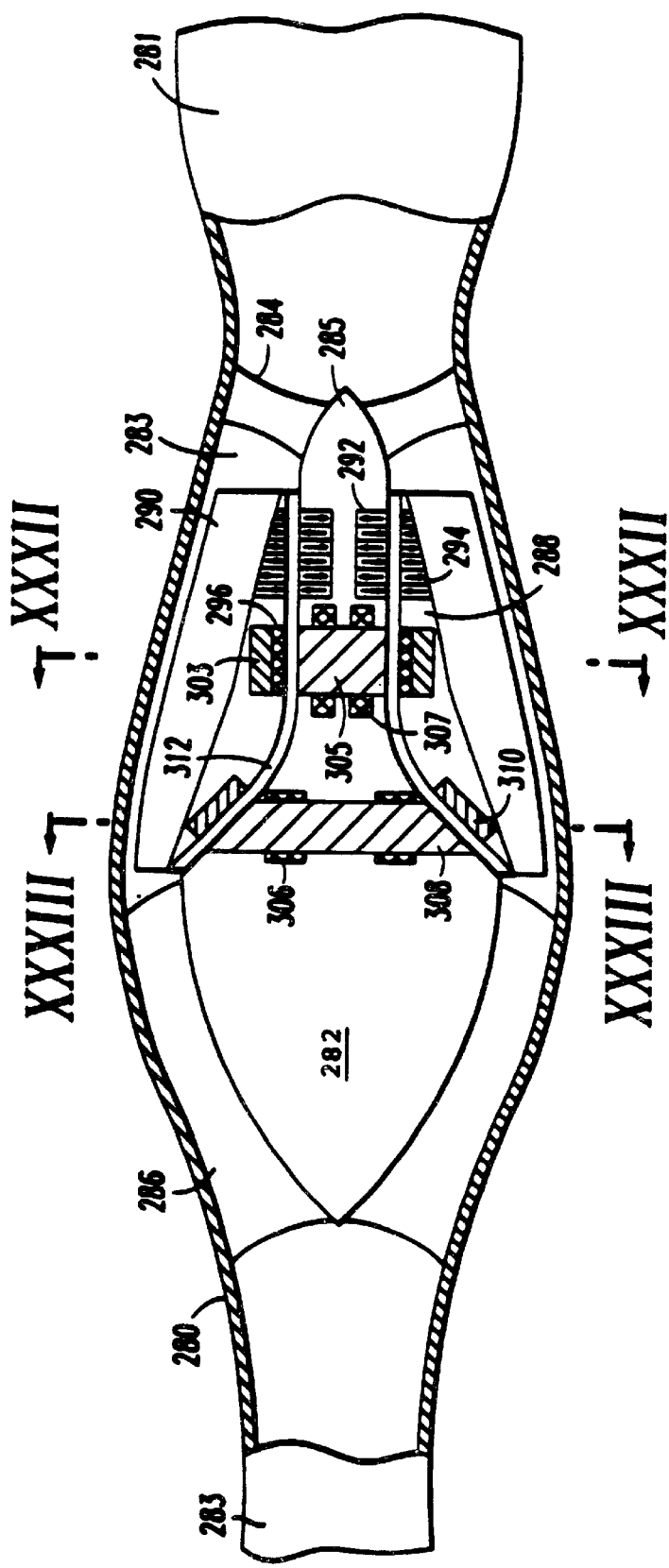
FIG. 31 is a cross-sectional view of an alternate embodiment of the rotary pump of the present preferred invention.
Figure 32:
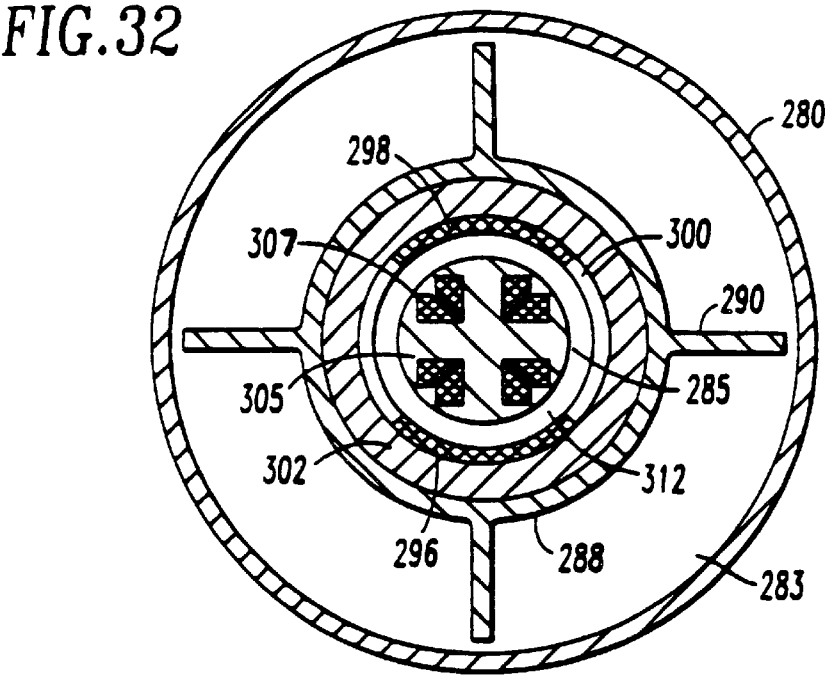
FIG. 32 is a cross-sectional view of the brushless DC motor of the rotary fluid pump shown in FIG. 31 taken along line XXXII—XXXII.
Figure 33:
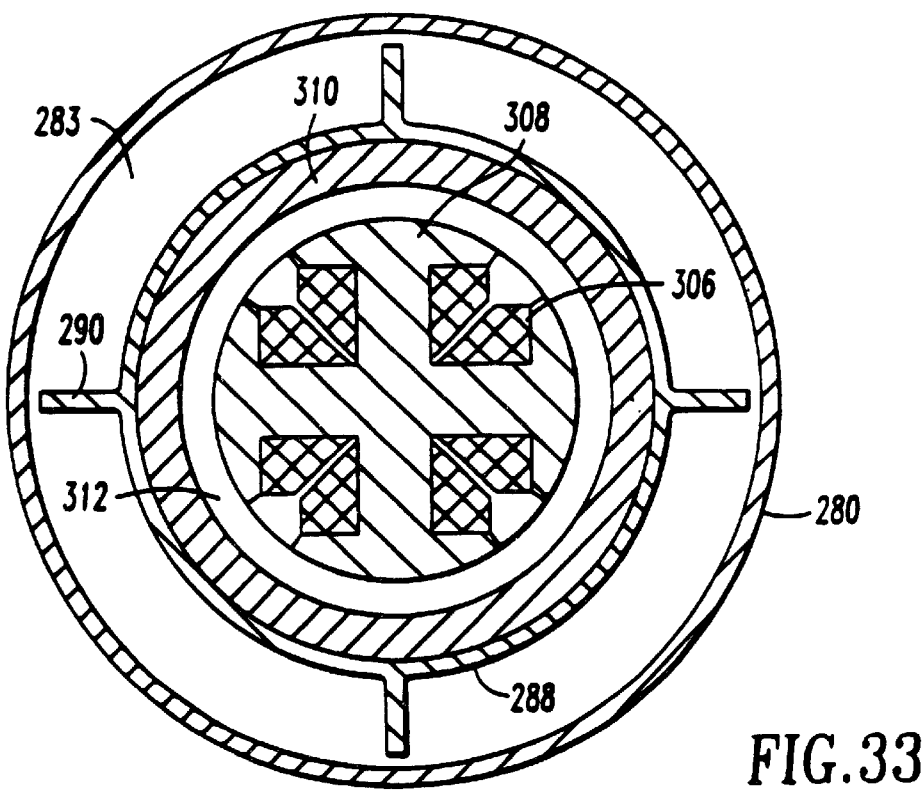
FIG. 33 is a cross-sectional view of the axial conical magnetic bearing of the rotary fluid pump shown in FIG. 31 taken along line XXXIII—XXXIII.

FIGS. 31 through 33 illustrate another embodiment of the present preferred invention which can be described by Formula 3 noted above. The rotary pump of FIGS. 31 through 33 comprises a housing 280 having an inlet 281 and an outlet 283, a stator 282 with an upstream set of stationary blades 284 and a downstream set of stationary blades 286, a substantially cylindrical impeller 288 defining a cavity extending therethrough and having impeller blades 290. The stator 282 is a substantially bell-shaped hub 285. The blood flows primarily through region 283. The conical bearing simultaneously centers the outlet end of the impeller 288 and supplies a thrust force on the impeller 288 in the direction of the outlet. The cylindrical permanent magnet bearing 292 and 294 supplies radial centering forces for the inlet end of the impeller 288. An axial force on the impeller 288 in the direction of the inlet 281 is provided by the same magnetic bearings 292 and 294. This type of bearing is shown in FIG. 7. The axial forces of the permanent magnet bearing and the active conical bearing are balanced via the conical bearing control. The permanent magnet bearing of FIG. 7 is stable in the radial direction, but unstable in the axial. By providing a slight offset as shown in FIG. 7, axial forces can be generated in the direction of the offset.

The means of rotation take the form of a brushless DC motor shown in detail in FIG. 32. The motor has a motor rotor flux return ring 302, stator iron 305 and stator coils 307. Permanent magnets 296 and 298 are magnetized in the radial direction. One inward and one outward creating a two pole motor. Region 300 is non-magnetic material suitable for supporting the permanent magnets. Region 302 is a flux return ring 303 for the motor made from soft magnetic material such as 3% silicon-iron or 50% cobalt-iron. Currents in the stator coils 307 are commuted to affect rotation of the motor. The communication signal is derived from the motor impeller angle through the use of back EMF signals on the coils. This can be accomplished by utilizing an integrated circuit from Micro Linear Corporation.

FIG. 33 is a section through the conical magnetic bearing depicting the coils 306, the stator iron 308 made from soft magnetic material, and the bearing rotor 310 made from soft magnetic material. The surface of the rotor iron interfacing the secondary blood flow region 312 is coated with a biocompatible material. Additionally its surface may be textured with rifling or small impeller blades to enhance blood flow through the region 312.

Figure 34:
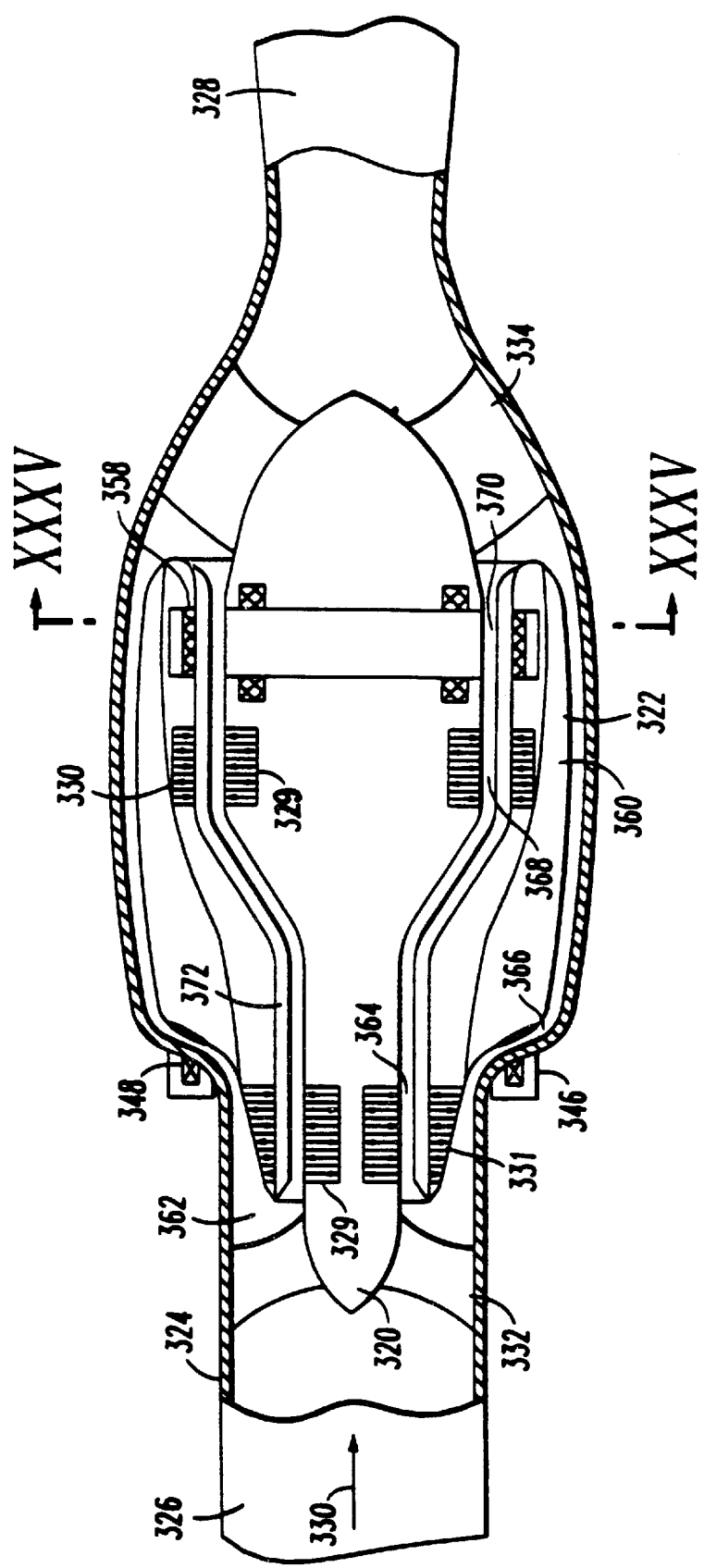
FIG. 34 is another alternate embodiment of the rotary fluid pump of the present preferred invention.
Figure 35:
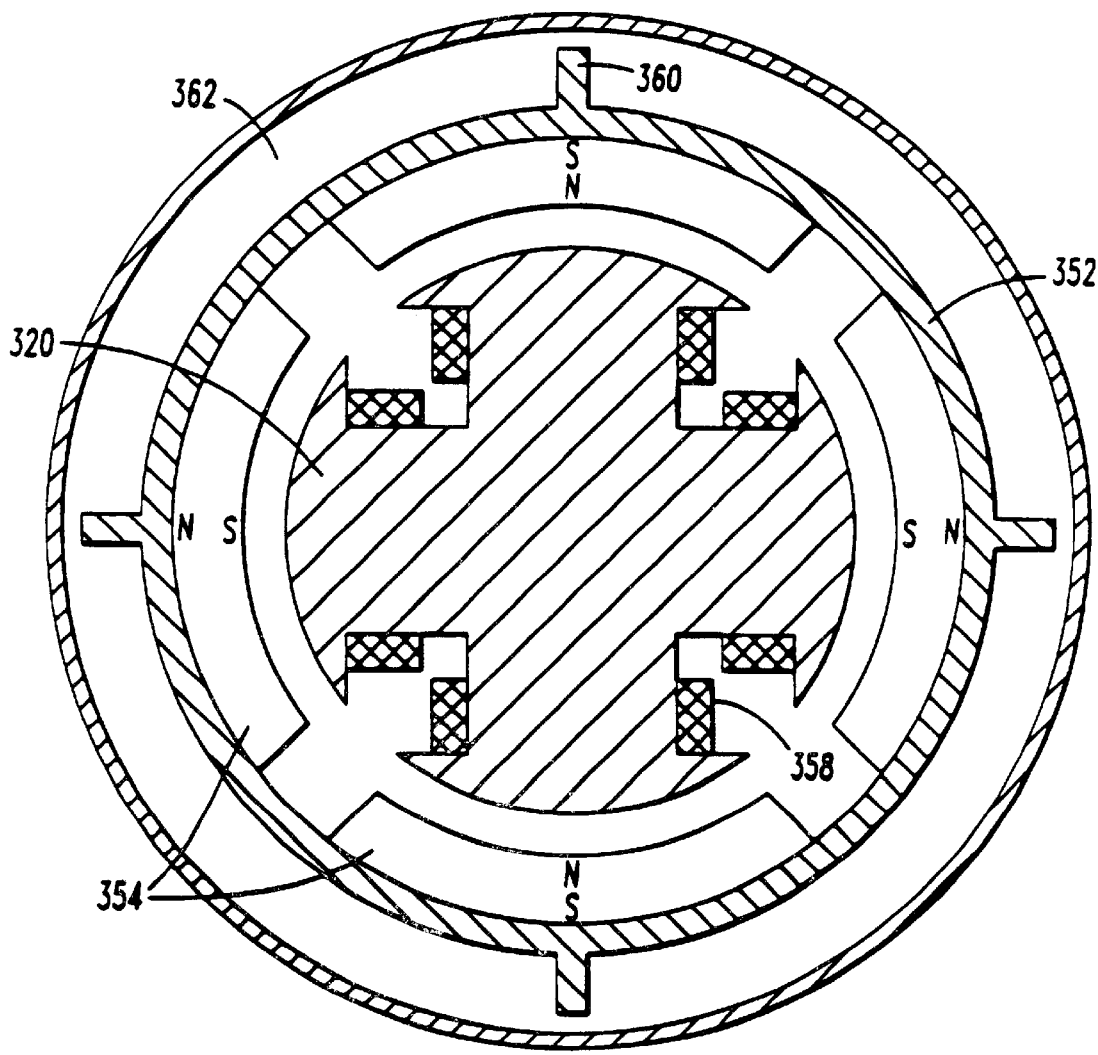
FIG. 35 is the cross-sectional view of the rotary fluid pump of FIG. 34 taken along line XXXV—XXXV.

FIGS. 34 and 35 show another embodiment of the present preferred invention. The advantages of this arrangement is that there is only one active magnetic bearing and brushless DC motor within an enlarged region of the fixed stator. FIG. 34 illustrates how an ATB2 can be located at the housing. Because the ATB is disposed in the housing, as opposed to the stator, there is more room in the stator and the motor can use larger wire and produce less heat. The rotor comprises a stator 320, and impeller 322 and a housing 324 with an inlet 326 and an outlet 328. The inlet 326 allows blood flow into the pump in the direction 330. The stator 320 is supported by stationary blades 332 at the inlet 326 and stationary blades 334 at the outlet 328. Permanent magnets 329 in the stator 320 and permanent magnets 331 in the impeller 322 support the impeller 322 on one end. Permanent magnet 329 in the stator 320 and permanent magnets 331 in the impeller 322 support the impeller 322 at the outlet 328. A thrust bearing stator 346, coil 348 and thrust target 348a provide support in the axial direction. Power to rotate the impeller is provided by a DC brushless motor consisting of an iron or other soft magnetic material, rotor ring 352, permanent magnets 354, and a stator coil 358. Blood pumped by the helical impeller blades 360 accelerates the blood through the outlet 328.

Blood flow is partitioned into a primary path 362 and secondary paths through component gaps 364, 366, 368 and 370, which define a continuous gap. The secondary blood flow paths serve the purpose of allowing for non-contact support of the impeller. In order to ensure that blood flows in the proper direction through the magnetic gaps, small blades or rifling may be added as shown at 372.

Figure 36:
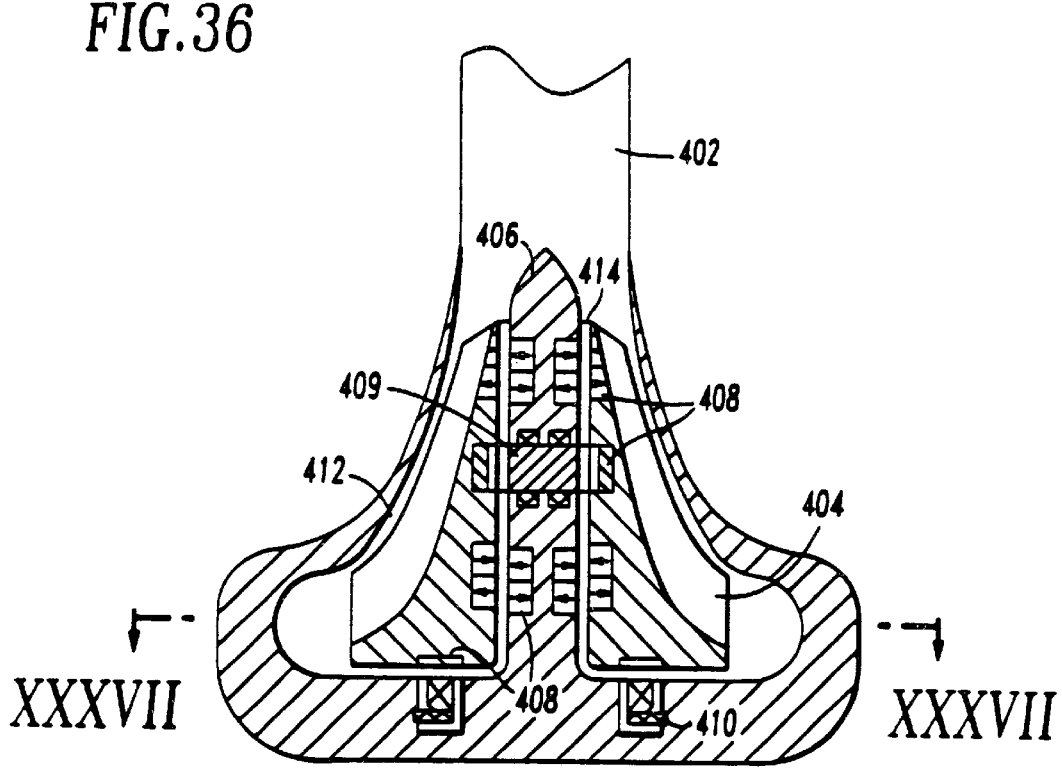
FIG. 36 is a cross-sectional view of another embodiment of the rotary pump of the present invention wherein the rotary pump takes the form of a centrifugal pump.
Figure 37:
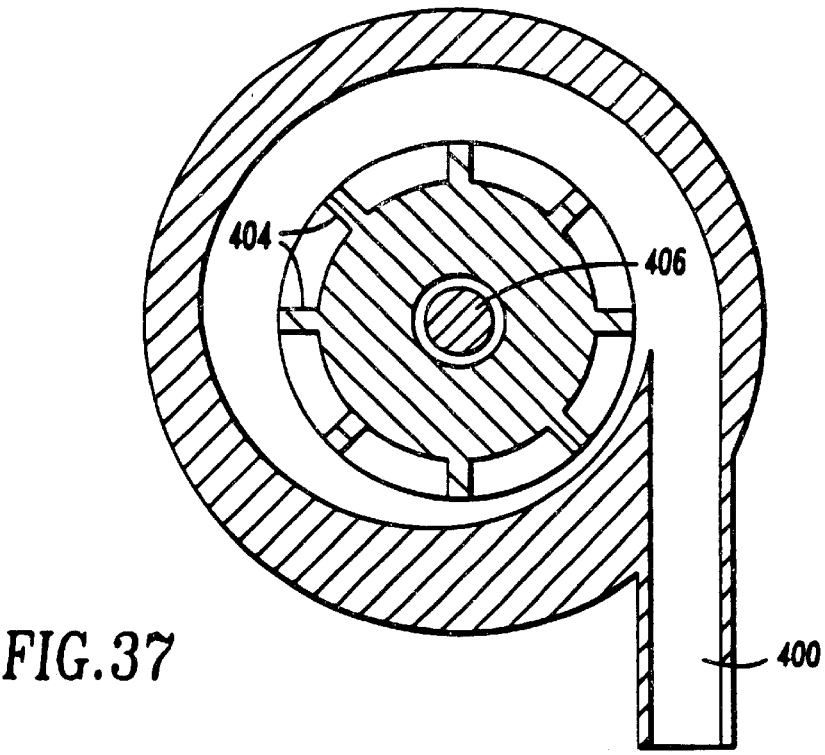
FIG. 37 is a cross-sectional view of the centrifugal pump of FIG. 36 taken along the line XXXVII—XXXVII.

FIGS. 36 and 37 illustrate a centrifugal pump which is a variation of the embodiment shown in FIG. 34 where the outlet 400 is radial instead of axial. The pump comprises housing 402, an impeller 404, a stator 406 means 408 for levitation and axially positioning the rotor and means for rotation 409. Also the thrust bearing is moved to lie downstream from all other magnetic components, and the thrust bearing has a permanent magnet bias magnet 410. Fluid flow gap 412 provides for the primary blood flow through the pump. A secondary fluid flow gap 414 also provides blood flow therethrough; however, gap 414 is small such that efficient levitation is provided. The anacronym for the embodiment shown in FIGS. 36 and 37 is represented by anacronym (11) above While the present preferred embodiments and method of making the same have been described herein, it is distinctly understood that the invention is not limited thereto, but may be otherwise variously embodied with the scope of the following claims and any equivalents thereof.

THE EMBODIMENT OF FIGS. 38–46

Figure 38:
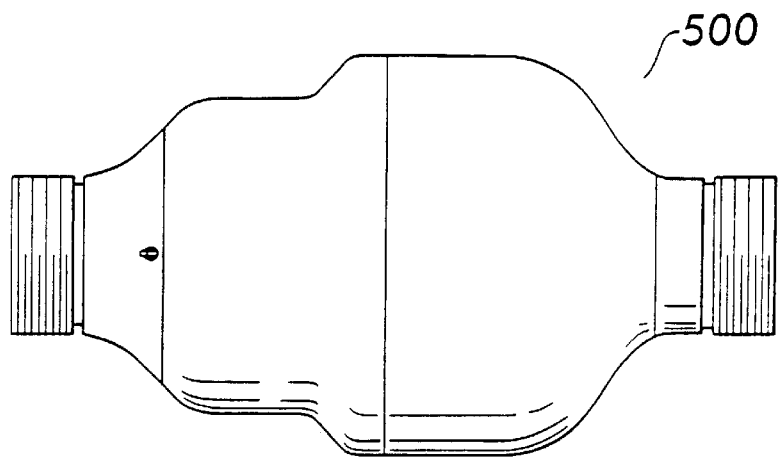
FIG. 38 is an alternative preferred embodiment of a blood pump of this invention.
Figure 39:
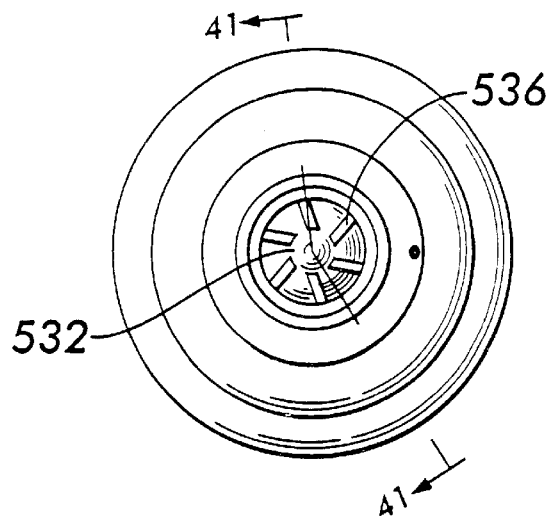
FIG. 39 is an end view of the outlet of the preferred embodiment of FIG. 38.
Figure 40:
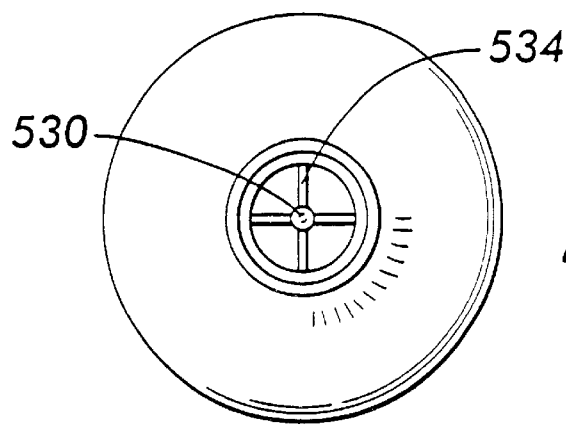
FIG. 40 is an end view of the inlet of the preferred embodiment of FIG. 39.
Figure 41:
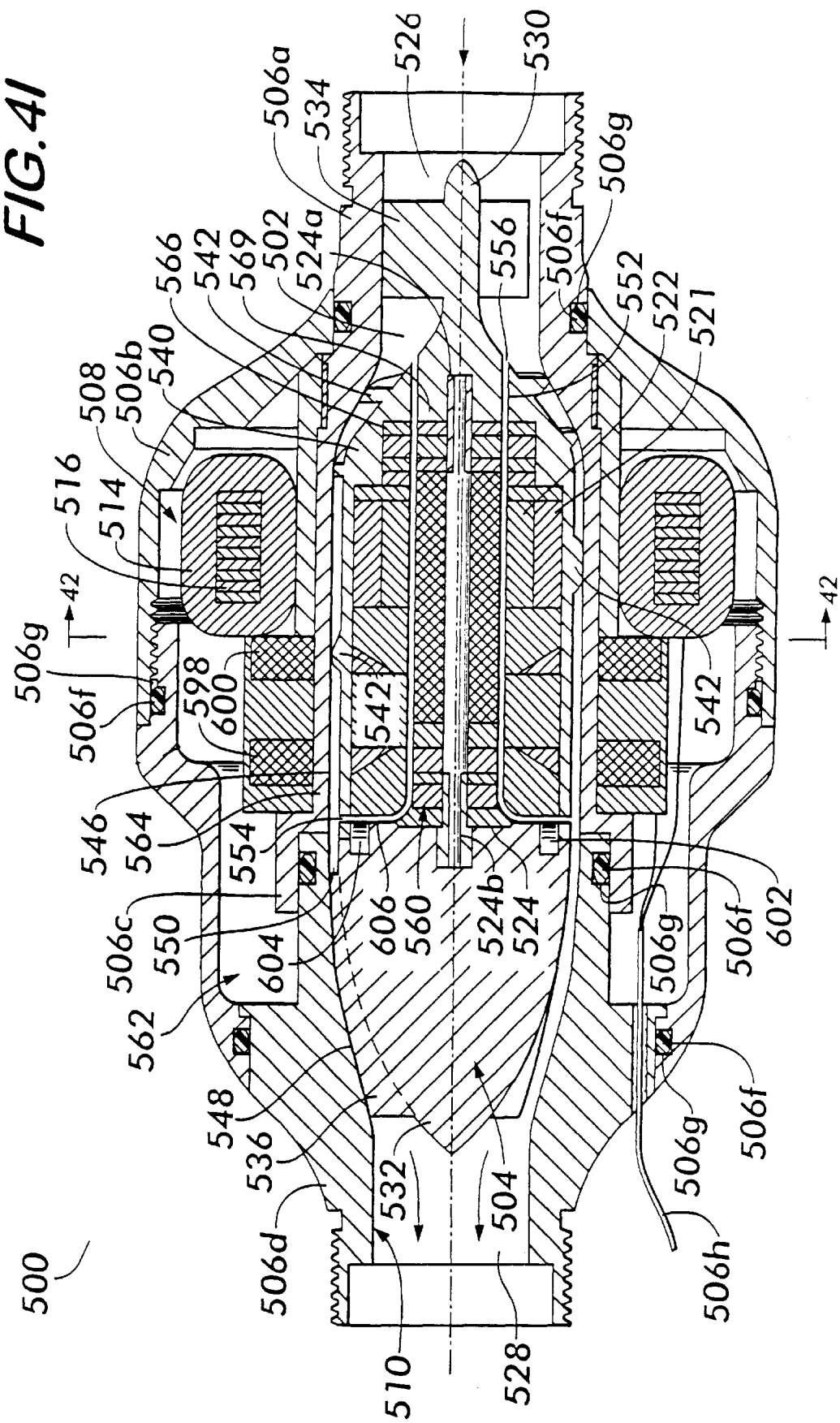
FIG. 41 is a cross-section taken along line 41—41 of FIG. 39.
Figure 45:
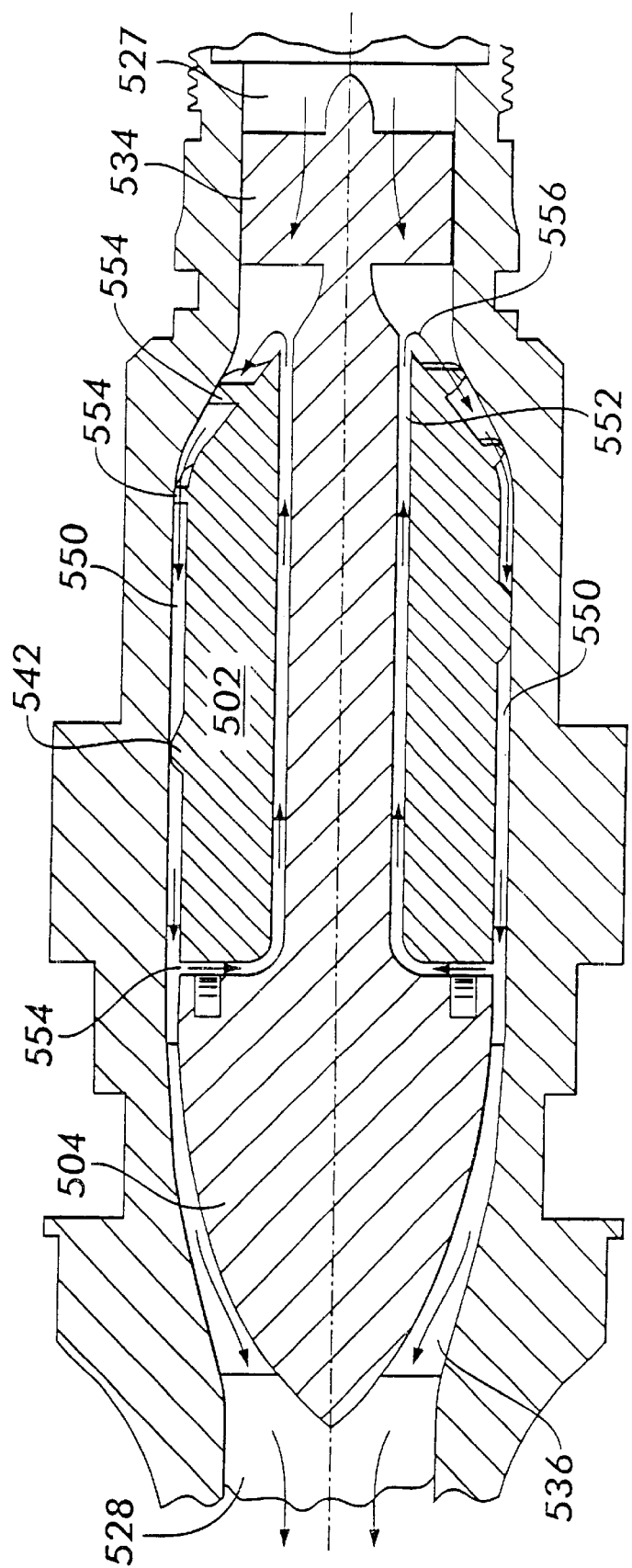
FIG. 45 is a diagrammatical view illustrating the preferred flow paths of the preferred embodiment of FIG. 38.

FIGS. 38–46 disclose another embodiment of a blood pump 500 of this invention. FIGS. 38–40 illustrate external views of the pump. This embodiment differs in several respects from the previous embodiments and is an improvement over the other embodiments described above. As shown in FIGS. 41 and 45, in this embodiment, the rotor 502 is magnetically suspended between a stator 504 or stationary fixed support member, that preferably has stator blades, and a housing 506 and rotates about the stator 504. Further, the motor stator 508 that drives the rotor 502 is preferably disposed within the housing 506, as shown in FIG. 41. By disposing the motor stator 508 within the housing 506 several advantages are achieved. First, the heat generated by the motor stator 508 is more easily transferred away from the blood, as compared to when the motor stator 508 is disposed within the stator 504. As described above, by removing the heat generated by the motor stator 508 away from the blood, it is easier to maintain the blood beneath a threshold temperature at which the blood tends to coagulate. This is significant in preventing thrombosis. Second, by placing the motor stator 508 within the housing 506, the stator 504, including the stator's external surface area, can be made smaller. By making the stator 504 smaller, the rotor 502 including is external surface area can be made smaller. In addition, the inner surface 510 of the housing 506 along which blood flows can be made smaller. By making the rotor 502, the stator 504 and the inner surface 510 of the housing 506 smaller, the surface area of the pump 500 that the blood contacts can be made smaller. This decreases the likelihood of the blood being contaminated by contact with foreign surfaces and hence increases the biocompatibility of the pump 500.

Some of the embodiments described above have similar features. For example, in the embodiment shown in FIGS. 1 and 30, the motor stator 508 was disposed within the housing 506, but these embodiments do not have a stator 504 about which the rotor 502 rotates. Further, the embodiments of FIGS. 31 and 34 have a stator 504 about which the rotor 502 rotates, but in these embodiments the motor stator 508 that drives the rotor 502 is disposed in the stator 504. Thus, while these other embodiments are improvements, these embodiments suffer from the disadvantages described above.

The embodiment of the pump 500 of FIGS. 38–46 also has several other inventive features including radial magnetic bearings, an electromagnetic thrust bearing that operates with a controller and a position sensor to control the axial position of the rotor and smooth conforming surfaces that form relatively smooth passageways for the blood to flow. Other inventive features of this embodiment are described below.

1. The Motor and the Housing

Figure 42:
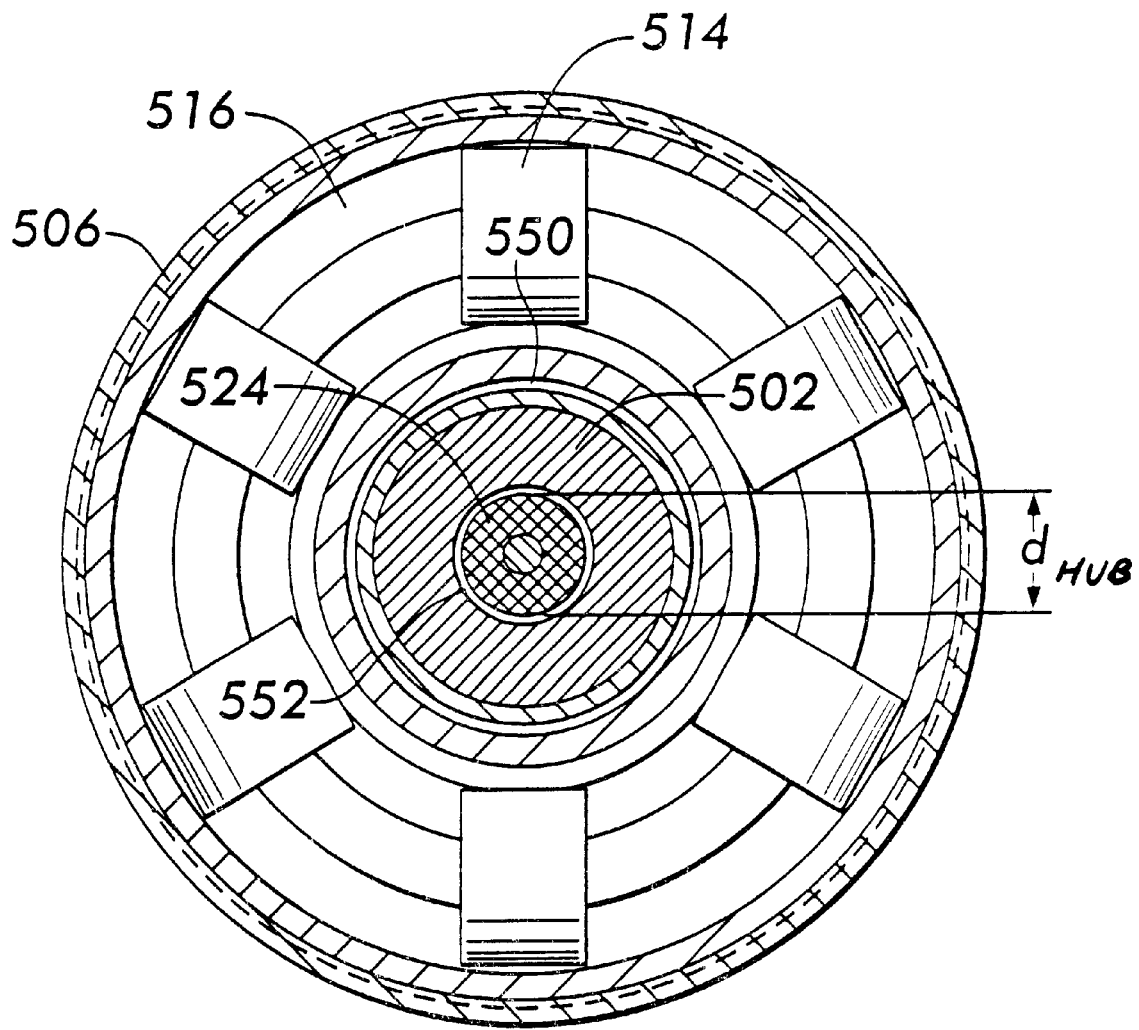
FIG. 42 is a cross section taken along line 42—42 of FIG. 41.

In a preferred embodiment, the motor shown in FIGS. 41 and 42 is a brushless 2-pole DC motor. The motor stator 508 is disposed within the housing 506 and preferably at the mid-section of the housing 506, so that the motor stator 508 is aligned with the rotor 502. The invention is not limited to this particular type of motor stator 508 and other types may be utilized, including, but not limited to slotted stator motors and motors with other numbers of poles. For example, a 4-pole motor may be employed and is beneficial because it produces a particular symmetric magnetic field in the motor gap in spite of interference from the thrust bearing magnets. In the preferred embodiment shown, the motor stator 508 has 6 motor stator coils 514 that are toroidally wound around stator laminations 516. The stator laminations 516 are preferably manufactured from relatively soft nickel alloy, but may be manufactured from other suitable materials, including, but not limited to silicon or cobalt alloys. The motor stator 508 can be attached to the housing with any conventional fastening technique. In one embodiment, the motor stator 508 is bonded to the housing with a suitable adhesive.

Preferably, the motor stator 508 is an unslotted stator, so that the magnetic attractive force between the motor stator 508 and the rotor 502 is decreased, relative to a slotted stator motor. The term motor stator 520 used herein with respect to the embodiments of FIGS. 38–46 refers to that portion of the motor around which the stator coils 514 are wound. The stator 504, as used herein with respect to the embodiment of FIGS. 38–46, refers to the stationary portion of the pump around which the rotor 502 rotates. Whether slotted or unslotted, the motor stator 508 produces a magnetic force that attracts the rotor 502 to the motor stator 508 and away from the preferred position in which the rotor 502 is suspended concentrically around the pump stator 504. In order to reduce the attractive force generated by the motor stator 508, the motor stator 508 is preferably unslotted. If the motor stator 508 was slotted, the motor stator 508 would have to be positioned further away from the rotor 502 in order to reduce the attractive force exerted on the rotor 502. This would increase the size of the pump 500 and thereby reduce the biocompatibility of the pump 500. Alternatively, the magnetic bearings that radially suspend the rotor 502 would have to be larger, again thereby increasing the size of the pump 500 and decreasing the biocompatibility of the pump 500.

In a preferred embodiment, the housing 506 is constructed from a material that has relatively low electromagnetic conductivity and permeability properties. Further, the housing material preferably has relatively high electromagnetic resistivity. For example, non-ferrous materials such as ceramics, titanium and non-magnetic stainless steel, such as 303 stainless steel, are preferred. By manufacturing the housing 506 from materials such as these, several benefits are obtained. First, because the housing 506 has relatively low electromagnetic conductivity, the eddy current losses within the housing are relatively small. Further, the low permeability of the housing increases the field induced on the motor rotor by the motor stator. This enables the motor stator 508 to be smaller, as compared to a similar pump that has a motor stator 508 disposed within a housing 506 manufactured from a material that does not have the properties described above. The use of a smaller motor stator 508 enables the pump housing 506 and the overall size of the pump to be made smaller. As described above, reducing the size of the pump has biocompatibility advantages because the surface area of the pump 500 in contact with the human body and the blood is thereby reduced.

The motor stator 508 interacts with a rotor motor magnet 521, shown in FIG. 41, to rotate the rotor and thereby pump blood. As is generally known, eddy current losses reduce the efficiency of an electromagnetic motor. These inefficiencies resulting from eddy current losses have the undesirable effect in blood pumps of having to increase the size of the motor stator 508 and thereby the pump 500. In order to minimize the eddy current losses, the rotor 502 may have an inner iron member 522, which is also shown in FIG. 41, that forms part of the interior portion of the rotor 502. This inner iron member 522 surrounds the fixed hub 524 of the stator 504 and thereby shields the fixed hub 524 from magnetic fields generated by the motor magnet 521 and the motor stator 508. This prevents or reduces the eddy current losses that would be formed from interaction of the magnetic field generated by the motor stator 508, the motor magnet 521, and the permanent magnets of the fixed hub 524. By preventing or reducing the eddy current losses, the motor stator 508 and the motor magnet 521 operate more efficiently and the size of the pump 500 can thereby be minimized.

The housing may be formed from any number of sections, but in the embodiment shown in FIG. 41, the housing includes four sections, 506a, 506b, 506c, and 506d. Sections 506a and 506d respectively define the inlet and outlet of the pump and may have threads disposed along at least a portion of their respective exteriors for installation purposes. Sections 506a, 506b and 506c form the mid-section of the pump. Section 506a is sealed to section 506b and section 506d with an o-ring 506f and a groove 506g, as are sections 506b and 506c, sections 506c and 506d. An electrical connector 506h for powering the motor may travel through a section of the housing and in the preferred embodiment shown in FIG. 41, the connector 506h travels through an aperture in section 506d.

2. The Rotor and Stator

The embodiment of FIGS. 38–46 also has several other advantages. For instance, a smooth fluid passage, as shown in FIGS. 41 and 46, is defined between the stator 504 and housing 506, the stator 504 and the rotor 502 and the rotor 502 and the housing 506. As described below, this smooth passage of fluid is defined by the geometric relationships between the housing 506, the rotor 502 and the stator 504 and the minimizing of an relatively sharp protrusions or edges.

The embodiment showing in FIGS. 38–46 is similar to that described above in that it includes a stator 504 that is coupled to the housing 506 at the inlet 526 and outlet 528 of the pump 500. As used herein with respect to the embodiment of FIGS. 38–46, the term stator 504 refers to that stationary portion of the pump about which the rotor 502 rotates. The term stator 504 is not intended to necessarily include the motor stator 508. Rather, the term stator 504 refers to a stationary member whether or not it has a motor stator. In this embodiment, the stator 504, as best understood with reference to FIGS. 41–43, preferably has a first end 530, a second end 532 and a fixed hub support 524 that connects the first end 530 to the second end 532. The first end 530, as shown in FIGS. 40, 41, 43 and 44B, is preferably disposed at the inlet 526 and has a plurality of stator blades 534 disposed about the periphery of the first end 530. In the embodiment shown, the first end 530 preferably has a substantially conically shaped nose, as shown in FIG. 43, so that blood can smoothly pass with minimal or no flow separation over the first end 530 as the blood enters the pump 500. The stator blades 534, shown in FIGS. 40, 41 and 44B, are disposed about the first end 530 and direct the blood flowing into the pump to the rotor 502, as is described in further detail below. Since a portion of the first end 530 has a substantially conically shaped nose, this portion of the first end 530 has a varying diameter. However, the maximum diameter of the first end 530 is preferably $d_{max1}$ as shown in FIG. 43 and is disposed at the upstream end of the first end 530 of the stator 504.

As shown in FIG. 42, the fixed hub 524 extends from the first end 530 to the second end 532. The rotor 502 is disposed about the fixed hub 524. The fixed hub 524 has a diameter $d_{hub}$ as shown in FIG. 45.

The second end 532 of the stator 504 is also preferably substantially conically shaped, as shown in FIGS. 41, 43 and 44A, and has a plurality of stator blades 536 disposed about its periphery. These stator blades 536 direct the blood flowing from the rotor 502 to the outlet 528 of the pump 500. The second end 532 of the stator 504 is also mechanically coupled to the housing 506. Because the second end 532 of the stator 504 is substantially conically shaped, the blood flowing over the second end 532 of the stator 504 can smoothly pass from the stator 504 to the outlet of the pump 500.

The second end 532 of the stator 504 is connected to the fixed hub 524, and because the second end 532 is substantially conically shaped it has a varying diameter. The maximum diameter of the second end 532 of the stator $d_{max2}$ is disposed proximate to the fixed hub 524, as best understood with reference to FIGS. 41 and 43. The fixed hub 524 may be connected to the first end 530 and the second end 532 by any of a variety of mechanical fastening techniques. In the preferred embodiment shown, the fixed hub 524 is connected to the first end and the second end with a pin 524a and a bushing guide 524b respectively. The pin 524a and the bushing guide 524b of the respective end of the fixed hub 524 connect the fixed hub 524 to the first end 530 through an interference fit and the fixed hub 524 to the second end 532 with an interference fit.

The rotor 502 is preferably disposed about the fixed hub 524, as shown in FIGS. 41 and 43, and has a substantially cylindrically shaped portion 538 and a substantially conically shaped portion 540. The rotor 502 preferably has an annular cross-section that is disk shaped. As described in more detail below, the rotor 502 is magnetically suspended about the fixed hub 524, and rotor blades 542 extend from the substantially conically shaped portion 540 to the substantially cylindrically shaped portion 538. When disposed about the fixed hub 524, the outer periphery of the substantially cylindrical portion 538 of the rotor 502 has a diameter $d_{rotor}$, as shown in FIG. 43. Preferably, the $d_{rotor}$ is approximately equal to the $d_{max2}$ of the second end 532 of the stator 504, so that a smooth passage of blood from the rotor 502 to the second end 532 of the stator 504 takes place as the blood passes through the pump.

By shaping and sizing the stator 504 and the rotor 502 as described above, relatively smooth surfaces are created that decrease the likelihood of the activation of platelets, coagulation and thrombosis. If the rotor 502 was not suspended so that the diameter of the rotor $d_{rotor}$ approximately equaled the diameter $d_{max2}$ of the second end of the stator 504, a rather abrupt transition would be created between the rotor 502 and the stator 504 that would increase the likelihood of damage to the blood cells.

The relatively smooth surfaces that prevent damage to the blood also include the substantially conically shaped first end 530 of the stator 504. The first end 530 of the stator 504 creates a relatively smooth surface that the blood contacts upon entering the pump so that shear stresses are minimized as the blood flow is redirected. This conically shaped relatively smooth surface of the first end 530 also directs the blood to flow to the substantially conically shaped section 540 of the rotor 502. Because the rotor 502 and part of the second end of the stator 504 have about the same diameter, a relatively smooth passage is created from which the blood can flow from the rotor 502 to the second end of the stator 504. After flowing to the second end of the stator 504, the substantially conically shaped second end 532 of the stator 504 provides a relatively smooth surface over which the blood flows, as the blood is redirected to the outlet of the pump 500 and from a larger diameter section to a smaller diameter section.

As alluded to above, the housing 506 encloses the rotor 502 and the stator 504. The housing 506 preferably has an inner surface 510, as shown in FIG. 41, that extends from the inlet 526 of the pump to the outlet 528 of the pump. As is described in further detail below, a primary flow path is defined between the housing 506 and the rotor 502 and the housing 506 and the stator 504. The inner surface 510 preferably has a shape that conforms to the shape of various parts of the rotor 502 and the stator 504, so that the primary flow path defined between the stator 504 and the rotor 502 is relatively smooth, and the blood flow experiences relatively minor changes in cross-sectional areas in the flow path. As described above, it is important in the design of blood pumps that relatively sharp protrusions and edges be avoided because they can cause shear stresses in the blood and create localized regions of stagnation in which the blood may coagulate.

One of the ways the pump 500 of this invention avoids having edges and relatively sharp protrusions is by having an inner surface 510 of the housing 506 that conforms to the shape of portions of the stator 504 and the rotor 502. For example, the inner surface 510 of the housing 506 has a first portion 542 that is curved along the substantially conically shaped portion 540 of the rotor 502 to create a relatively smooth passage of blood between the rotor 502 and the housing 506. This is particularly important in this region of the pump 500 because the rotor blades 542 on the substantially conically shaped portion 540 of the rotor 502 are imparting energy to the blood and the blood is being redirected from flowing in a substantially axial direction to an angular direction that is an angular relationship with the longitudinal axis of the pump. Redirecting the direction of flow of the blood and the pumping action of the impeller blades 542 has the potential to cause shear stresses on the blood. In order to reduce the likelihood of damage to the blood cells, the inner surface 510 of the housing 506 is curved to conform to the substantially conically shaped section of the rotor 502. This provides a relatively smooth redirection of the blood as the blood is pumped and flows between the substantially conically shaped section 540 of the rotor 502 and the inner surface 510 of the housing 506.

The inner surface 510 of the housing 506 also has a second portion 546 that is disposed proximate to the substantially cylindrical shaped section of the rotor 502. This second portion 546 of the housing 506 is preferably substantially cylindrically shaped, so as to conform to the shape of the substantially cylindrically shaped section 538 of the rotor 502. This creates a relatively smooth passage of flow between the substantially cylindrical portion 538 of the rotor and the inner surface 510 of the housing 506. As discussed above, the creation of a relatively smooth flow passage minimizes the shear stresses and the likelihood of damage to the blood cells.

A third portion 548 of the inner surface 510 of the housing 506 preferably extends from the second portion 546 of the inner surface 510 of the housing 506 and is disposed proximate to the substantially conically shaped second end 532 of the stator 504. Similar to the first portion 540 of the inner surface 510 of the housing 506, the third portion 548 of the inner surface 510 of the housing 506 conforms to the substantially conically shaped second end 532 of the stator 504 to create a relatively smooth flow passage between these two surfaces. While flowing between the substantially conically shaped second end 532 of the stator 504 and the third portion 538 of the inner surface 510 of the housing 506, the flow is being redirected from the axial direction to a direction that is an angular relationship with the axial direction. Additionally, the flow is being straightened by the stator blades 536. One of the primary concerns with blood flowing between the stator and the housing is preventing flow separation, flow reversal, stagnation and thrombosis that can result from these phenomena. In order to reduce the likelihood of flow stagnation, flow reversal and thrombosis, the conforming surfaces of the pump define a relatively smooth flow passage between the stator and the housing.

By configuring the pump as described above, the blood pump is a mixed flow pump. A mixed flow pump being one that combines the characteristics of both axial and centrifugal pumps. As is generally known, axial pumps have a fluid entering along an axis and the general direction of fluid flow is parallel to this axis through the pump. Centrifugal pumps generally have a fluid entering in the pump in a direction that is generally parallel to the axis of symmetry of the pump rotor and exiting the pump in a direction that is generally perpendicular to the direction at which the flow enters the pump. A mixed flow pump combines the characteristics of these pumps and has flow in a direction other than the general direction of flow as defined in these types of pumps. For example, as shown in FIG. 45, the flow enters the pump in generally the axial direction and then is diverted to an angular direction with the longitudinal axis of the pump, as the blood passes the substantially conically shaped section 540 of the rotor 502. After which, the flow returns to is generally axial direction as the blood passes along the substantially cylindrical portion 538 of the rotor 502. After flowing past the substantially cylindrical portion 538, the blood begins in an angular direction again along the substantially conically shaped second end 532 of the stator 504. Following this, the flow again is redirected to the axial direction as the blood exits the pump.

Blood pumps generally operate under what are regarded as intermediate flow and pressure conditions. At these conditions, a mixed flow pump is more efficient and therefore preferred over centrifugal and axial pumps. As is generally known, axial flow pumps are preferred in applications involving relatively low pressures and high flow rates, and centrifugal flow pumps are preferred in applications involving relatively high pressures and low flow rates. Thus, by providing a mixed flow pump, this invention provides a pump that operates most efficiently for its application. Further, the mixed flow design conveniently accommodates the required diameter increase necessary to house the rotor and stator.

As described above, increasing the efficiency of the pump permits the pump to be smaller and thereby enhances its biocompatability. For example, the pressure is generated predominately by the substantially conical shaped portion 540 as the rotor 502. By generating a significant portion of the pressure in this section of the pump, the substantially cylindrically shaped portion 538 of the rotor 502 can be made relatively smaller which permits the size of the primary flow path across which the motor operates to be smaller and thereby increases the efficiency of the pump. In contrast, if the pump was axial in design, the size of the rotor and the motor would have to be larger to obtain the same operating conditions. Although this preferred embodiment has been described in terms of a mixed flow pump, this is not intended to limit the application of other features of the pump to mixed flow pumps except where expressly stated. This invention includes pumps with a housing in which a motor is disposed and that has a rotor that rotates about an inner stator that are not mixed flow pumps. In a preferred embodiment, the pressure rise between the conical portion of the rotor and the housing is in the range of about 80–140 mm. Hg at a flow rate of about 3 to 10 liters/min.

The pump of FIGS. 38–46 can be described in terms of the acronyms described above. Using these terms, the pump is described as follows:

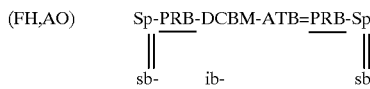

The ATB and PRB are hybridized in this embodiment because the aft bearing outer race shares magnets with the active thrust bearing. This hybridization need not be used and separate magnets may be used. However, by hybridizing, fewer parts are used which provides manufacturing and economic advantages.

3. The Flow Paths

Similar to some of the embodiments described above, the pump of FIGS. 38–46 has two flow paths, as are best shown in FIG. 45. There is a primary flow path 550 between the rotor 502 and the housing 506 and a secondary flow path 552 between the rotor 502 and the stator 504, as is best shown in FIG. 45. The primary flow path 550 is larger than the secondary flow path 552, and the majority of blood passing through the pump flows through the primary flow path 550. The secondary flow path 552 is necessitated by the use of magnetic bearings which permit the rotor 502 to levitate. The creation of a secondary flow path 552 across which the magnetic bearings communicate with the rotor to suspend the rotor 502 is significant because without a secondary flow path 552, the magnetic bearings must work across the primary or only flow path in the pump. Because magnetic bearings need to be relatively close together in order to be efficient, without a secondary flow path the rotor would have to be disposed relatively close to a housing and the size of the flow path would be limited and therefore, the flow rate would be limited. Thus, the creation of a secondary flow path permits the magnetic suspension of a rotor without limiting the size of the primary flow path and the flow rate. The size of the flow path could be increased by using larger bearings in lieu of a secondary flow path, but this would increase the size of the pump and cause the biocompatibility disadvantages alluded to above.

The dimensions of the secondary flow path 552 are important for both the operation and the hemo-compatibility of the pump 500. If the secondary flow path 552 is too small, the magnitude of the shear stresses on the blood from the relatively small flow path can become excessive and result in damage to the red blood cells, coagulation and thrombosis. Conversely, if the secondary flow path 552 is too large, the rotor 502 will be disposed farther away from the stator 504. This increased distance results in less efficient magnetic bearings and causes the magnetic bearings to be larger in order to generate the same magnetic force. This can result in an increase in pump size which has the biocompatibility disadvantages discussed above. Furthermore, if the secondary flow path is too large, it will provide excessive flushing or leakage losses which degrade the hydrodynamic efficiency of the pump and cause undesirable flow disturbances at the interfaces of the primary and secondary flow paths. In a preferred embodiment of this invention, the distance between the stator 504 and the rotor 502 is within the range of about 0.005 ins. to about 0.03 ins. Of course, the preferred size of the secondary flow path 552 will depend on the overall size of the pump 500. Further, the preferred distance from the exterior of the rotor to the housing that determines the primary flow path is about 0.0495 ins. What is important is that the secondary flow path 552 is large enough to prevent excessive shear stresses, yet small enough to prevent the efficiency of the bearings from being decreased and the overall size of the pump 500 from having to be thereby increased.

As referenced above, the flow in the secondary flow path 552 is preferably from the downstream end 554 of the secondary flow path 552 through the secondary flow path 552 and out the upstream end 556 of the secondary flow path 552. In other words, the flow through the secondary flow path is retrograde and opposes the flow in the primary flow path 550. This embodiment of the pump 500 was designed with retrograde flow between the rotor 502 and the stator 504 in order to increase the flushing of the secondary flow path 552. In order to design a magnetically suspended rotor 502 about a stator 504, it has been found that the secondary flow path 552 must be of a requisite size in order for the magnetic bearings to be efficient and in order to prevent excessive shear stresses. Another concern with a secondary flow path 552 is to ensure that the flow rate through the secondary flow path 552 is sufficient to provide adequate flushing and prevent regions of stagnation and the coagulation of platelets that can result from stagnation. Through design and experimentation, it has been found that it is difficult to prevent stagnation and provide adequate flushing when the flow in the secondary flow path 552 is in the same direction as the flow in the primary flow path 550. For example, the size of the secondary flow path 552 would have to be increased which has the disadvantages described above. Thus, in a preferred embodiment the pump 500 has been designed with retrograde flow through the secondary flow path 552 to provide adequate, but not excessive, flushing and thereby maintain the size of the secondary flow path 552 relatively small.

4. The Blades

Disposed on the rotor 502 are preferably a plurality of rotor blades 542, as best shown in FIG. 43. These rotor blades 542 extend from the substantially conically shaped portion 540 of the rotor 502 onto the substantially cylindrical portion 538 of the rotor 502. Preferably, the rotor blades 542 are curved or wrapped in a substantially helical pattern about the substantially cylindrical portion 538 of the rotor 502. Upon reaching the cylindrical portion 538 of the rotor 502, the curvature (wrap) of the rotor blades 542 decreases, as is best shown, in FIG. 43.

This curvature (wrap) is preferable for a variety of reasons. The function of the helical curved blades 542 on the conically shaped end 540 of the rotor 502 is primarily to impart pressure energy, rotational velocity and axial velocity to the blood. In contrast, the primary functions of the portion of the blades 542 on the substantially cylindrical portion 538 of the rotor 502 is to impart further rotational kinetic energy to the blood and serve as a guide to direct the flow of blood toward the leading edge of the stator blades disposed at the second end 532 of the stator 504.

Each rotor blade 542 has a tip 556 and a root 558, one of which is shown in FIG. 43. The tip 556 of each rotor blade 542 is preferably rounded. Similarly, each blade 556 has a fillet 560 disposed in either side of the root 558 of each blade 542 where the root 558 contacts the peripheral surface of the rotor 502. By rounding the tip 556 and providing fillets 560 at the root 558 of each blade 542, the relatively sharp edges associated with flat tips and roots that mate with a surface at right angles are generally eliminated. The elimination of these relatively sharp edges is advantageous because the sharp edges can cause shear stresses within the blood and non-filleted intersections can cause localized regions of relatively stagnant blood. This may result in coagulation or thrombosis. Therefore, the rounding of the tip 556 and the creation of fillets 560 at the root 558 of the blades 542 along the length of the respective blade 542 reduces the shear stresses and problems associated with the shear stresses. In a preferred embodiment, the blades are curved at a curvature that is approximately within the range of about 0.002 ins. to about half of the width of the blade.

The stator blades 536 disposed on the second end 532 of the stator 504 preferably have a reverse spiral curvature, as shown in FIGS. 43 and 44A. Because of this curvature (wrap), the stator blades 536 straighten the flow, as the blood exits the pump 500, and reduce the rotational kinetic energy of the blood in the circumferential direction and thereby recover pressure energy from the blood. The thickness of the blades are designed so as to minimize axial variations in the flow path's cross sectional area. This minimizes the potential for flow separation from the hub and the blades, which reduces the likelihood of blood damage.

In the embodiment shown in FIGS. 43 and 44A the stator blades 536 on the second end of the stator having a changing thickness in order to keep the net cross-sectional area of the flow path constant and thereby prevent flow separation. For instance, as the shape of the housing changes proximal to the stator blades 536, the stator blade thickness is adjusted to maintain the cross-sectional area relatively constant. As the shape of the housing tends to increase the size of the flow path, the thickness of the stator blades is increased to maintain the cross-sectional area of the flow path relatively constant.

5. The Magnetic Bearings

As alluded to above, the pump of FIGS. 38–46 also has magnetic bearings that magnetically suspend and position the rotor 502 radially and axially between the housing 506 and the stator 504. A preferred embodiment of a radial magnetic bearing 560 and a thrust bearing 562 is provided below, but other magnetic bearings may be utilized. In the embodiment provided below, the radial magnetic bearing 560 is a passive bearing, and the thrust bearing 562 is an active bearing that senses the position of the rotor 502 during the operation of the pump and provides an axial force to the rotor 502 to position the rotor 502 axially within the pump.

In the embodiment shown in FIGS. 38–46, two radial bearings 560 are provided. Both sets of radial bearings 560 include a stack of permanent magnets disposed within the stator 504 and a stack of permanent magnets disposed with the rotor 502, as shown diagrammatically in FIG. 46. These stacks of permanent magnets include the rotor aft stack 564, the rotor forward stack 566, the stator aft stack 568 and the stator forward stack 569. The arrows in the FIG. 46 indicate the direction of the magnetic field produced by a particular component. The arrow head indicates north and the tail indicates south.

The rotor aft stack 564 of permanent magnets includes, in a preferred embodiment, three magnets 570, 572, 574. The combination of these three magnets forms what is referred to as an aft outer race. They are referred to as an outer race because each of the permanent magnets 570, 572, 574 is shaped in the form of a ring. Preferably, the rotor magnets of the aft stack 564 or race are magnetized in alternating directions as shown in FIG. 46. Preferably, the aft rotor stack 564 of permanent magnets also includes two thrust poles 582, 584 which form part of the thrust bearing 562, as described in detail below. Aligned with the aft rotor stack 564 of permanent magnets may be the aft stator stack 568 of permanent magnets. Similar to the rotor aft stack 564, the stator aft stack 568 includes three permanent magnets 576, 578, 580. The aft stator stack 568 also includes a spacer 575 disposed between two of the three after stator stack magnets. The magnets that define the aft stator stack 568 are also preferably shaped in rings and together are referred to as the aft inner race.

Similarly, the forward rotor stack 566 of permanent magnets includes in a preferred embodiment three permanent magnets 586, 588, 590 that define the forward outer race. These magnets are preferably magnetized in alternating directions, as shown in FIG. 46, and in alternating directions from those magnets that define the aft outer race 564. The stator forward stack 569 also includes three magnets 592, 594, 596 of alternating polarity from each other and the magnets that define the aft stator magnets. The forward stack 569 of stator magnets defines the forward inner race.

Together the aft outer 564 and inner races 568 define an aft radial bearing and the forward outer 566 and inner races 569 define a forward radial bearing. Each of these bearings communicates magnetically across the secondary flow path 552 that separates the rotor 502 from the fixed hub 524 to magnetically suspend the rotor 502 from the stator 504, as shown in FIG. 41. The size of the secondary flow path 552 or gap across which the respective inner and outer races must communicate with each other is important for the proper operation of the pump. As described above, the gap must be small enough to provide for efficient transmission of magnetic force in the radial direction to levitate the pump, so that the bearings and pump size can be minimized, yet not so small as to cause excessive shear stresses on the blood. A preferred size of this gap is provided above.

The forward radial bearing defined by the forward outer race 566 and the forward inner race 569 is similar to other magnetic bearing construction such as that described in Backers, FT "A Magnetic Journal Bearing," Phillips Technical Review, Vol. 22, pp. 323–328 (1960–61) and Yonnet J. P., et al. "Stacked Structures of Passive Magnet Bearings," J. Appl. Physics 70(10):6633–6635 (1991). A preferred embodiment of a radial magnetic bearing that magnetically suspends the rotor 502 about the stator 504 has been provided above. However, other magnetic bearings configurations are possible. For example, a different number of magnets may be used and/or different polarity of magnets may be used. Further, active magnetic bearings may also be used.

Because of the position of the rotor motor magnet 521 relative to the forward radial magnetic bearing, the forward inner race 569 has the potential to interact magnetically with the rotor motor magnet 521. For example, the motor stator 508 can create a dipole moment that interacts with a dipole moment created by the inner race magnets. This interaction would produce an undesirable moment on the rotor 502 in the pitch and yaw directions that bends the rotor 502 away from its preferred suspended position between the stator 504 and the housing 506. In order to prevent this undesirable bending moment, the thicknesses of the outer magnets 586, 590 that define the forward inner race are adjusted until the moment generated by the forward inner race 569 is approximately zero. This nullifies and minimizes any interaction between the rotor motor magnet 521 and the forward inner race 569 and thereby prevents or minimizes the undesirable bending moment that results from the interaction. In a preferred embodiment the thicknesses $t_1$ and $t_2$ of the magnets that define the forward magnetic bearing about twice the distance between the inner and outer races or twice the size of the secondary flow path. The overall length of the stack of magnets is preferably shown so as to achieve sufficient stiffness to support the rotor while its rotating. Likewise the thicknesses $t_3$ $_{and}$ $t_4$ of two of the magnets that define the forward inner race 569 are adjusted to match the thicknesses $t_1$ and $t_2$ of the corresponding outer magnets.

In order to position the rotor 502 axially within the housing, the pump must also have a thrust bearing 562. Preferably, the thrust bearing 562 is an active magnetic bearing that adjusts the axial force on the rotor 502 to maintain the proper position of the rotor 502. In a preferred embodiment, the thrust bearing 562 includes the aft outer race 564, a pair of thrust poles 582, 584, a pair of thrust coils 598, 600. position sensors 602. 604 and a controller 620 that controls the force exerted on the rotor 502 in response to the position sensors 602.

As described above, the aft outer race 564 and the thrust poles 582, 584 are positioned within the rotor 502, and the aft inner race 568 is disposed within the stator 504. The thrust coils 598, 600 are electromagnetic coils that are disposed within the housing 506, as shown in FIG. 41. In a preferred embodiment, one of the thrust poles 582 is a north pole and the other is a south pole. Thrust coil 598 preferably interacts with thrust pole 582, and thrust coil 600 preferably interacts with thrust pole 584. The electrical currents through the thrust coils 598, 600 are preferably counter rotating, so that they each interact with the respective thrust poles 582, 584 to produce an axial force in the same direction. The magnetic field generated by the aft inner 564 and outer 568 races interacts with the magnetic field generated by the thrust coils 598, 600 and the thrust poles 582, 584 to provide an axial force that positions the rotor 502 axially within the housing 506.

Position sensing coils 602, 604 shown in FIG. 41, are preferably disposed within the second end of the stator 504 and at the stator face 606. The sensing coils 602, 604 may be of the eddy current type, but other suitable sensors may be used.

In order to properly position the rotor 502 axially, a controller that controls the current through the thrust coils is disposed. In a preferred embodiment, the controller is a conventional feedback controller, such as that described above, that is responsive to the sensing coils 602, 604 to position the rotor axially. The sensing coils send an electrical signal to the controller that is indicative of the axial position of the rotor. The controller adjusts the current in the thrust coils to reposition the rotor in the preferred axial position.

In an alternative preferred embodiment, a Virtually Zero Power (VZP) controller 620, shown schematically in FIG. 46, is used with the feedback controller. The VZP controller positions the rotor 12 at the zero velocity point along the axial axis of the pump. The zero velocity point is an unstable equilibrium point where static loads and unstable forces produced by the radial bearings are balanced and a net force of zero is produced. An advantage of employing a VZP controller is that the power required to maintain this position, assuming no external disturbances, is about equal to the quiescent power of the controller's electronics, and therefore is relatively small.

In operation the sensing coils 602, 604 measure the position of the rotor and conventional position feedback is used to suspend the rotor initially. After a stable suspension of the rotor is achieved, the VZP controller 620 maintains the position of the rotor.

The VZP controller can be of the type that uses velocity feedback to position the rotor at the zero velocity point and is described generally in Carl H. Henriksoti, Joseph Lyman, and Philip A. Studer,: *Magnetically Suspended Momentum Wheels For Spacecraft Stabilization*, presented at the AIAA 12th Aerospace Sciences Meeting, Washington D.C. Jan. 30–Feb. 1, 1974 and available as AIAA Paper No. 74–128, p. 4–5 (1974) and Joseph Lyman: *Virtually Zero Powered Magnetic Suspension, U.S. Letters Pat. No.* 3,860,300, Jan. 14, 1975, which are both hereby incorporated by reference. Alternatively, the VZP controller can be of the type that uses integral feedback of a signal that is a function of the current in the thrust coils 598, 600. This type of controller is described in Ball Brothers Research Corp.: *Annular Momentum Control Device (AMCD)*, Volume I: Laboratory Model Development, NASA CR-144917, pp. 4–6–4–9, (1976), which is hereby incorporated by reference. In either type, the preferred position is the zero velocity position.

Various inventive features of a blood pump of this invention have been described above. It will be appreciated that not all inventive features need be combined in a single pump. Rather, some inventive features may be included within other pumps without using other inventive features.

It is to be understood, however, that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meaning of the terms in which the appended claims are expressed.

What is claimed is:

1. A pump for pumping blood, comprising:

a housing;

a stator disposed within the housing and coupled to the housing;

a rotor disposed within the housing and suspended around the stator;

the rotor and stator defining a primary blood flow path between the rotor and the housing and a secondary blood flow path between the rotor and the stator;

at least two radial magnetic bearings for suspending the rotor between the stator and the housing, said radial magnetic bearings each comprising at least one stator suspension magnet disposed within the stator and at least one rotor suspension magnet disposed within the rotor, the stator and rotor suspension magnets communicating across the secondary flow path; and a motor for rotating the rotor with respect to the stator, said motor comprising at least one electromagnetic coil within the housing, said electromagnetic coil communicating with at least one rotor motor magnet in the rotor, said communication being across the primary flow path to rotate the rotor with respect to the stator and thereby pump blood through the pump.

2. The blood pump of claim 1, wherein the stator further comprises a first end disposed at an inlet of the pump, a second end disposed at an outlet of the pump and a fixed hub that connects the first end to the second end.

3. The blood pump of claim 2, wherein the stator further comprises a plurality of stator blades extending from the first end of the stator and a plurality of stator blades extending from the second end of the stator.

4. The blood pump of claim 1, wherein the motor comprises an unslotted motor stator, disposed in the housing.

5. The blood pump of claim 1, wherein the housing comprises a material of relatively low electro-thermal conductivity.

6. The blood pump of claim 1, wherein the housing comprises a ceramic material.

7. The blood pump of claim 1, wherein the housing comprises non-magnetic stainless steel.

8. The blood pump of claim 1, wherein the rotor motor magnet comprises a permanent magnet for interacting with the electromagnetic coil.

9. The blood pump of claim 1, wherein one of the stator suspension magnets has a thickness that reduces the magnetic interaction between the respective stator suspension magnet and the motor magnet to reduce a moment, created by the interaction of the motor magnet and the stator suspension magnet, that biases the rotor from a preferred suspended position.

10. The blood pump of claim 1, wherein the rotor magnet comprises a plurality of ring shaped magnets of alternating polarities and the stator magnet comprises a plurality of ring shaped magnets of alternating polarities.

11. The blood pump of claim 1, further comprising thrust coils, disposed within the housing and thrust poles, disposed within the rotor, one of the thrust coils interacting with one of the thrust poles and the other of the thrust coils interacting with the other of the thrust poles to position the rotor axially within the housing.

12. The blood pump of claim 11, further comprising at least one sensing coil, disposed within the stator, that senses the axial position of the rotor.

13. The blood pump of claim 12, further comprising a controller, that interacts with the thrust coils to control an electrical current through the thrust coils in response to the at least one sensing coil so that the thrust coils apply an axial force on the rotor to position the rotor axially within the housing.

14. A system for pumping blood, comprising:
   (i) a pump, comprising:
      a housing that has an inlet and an outlet;
      a stator disposed within the housing and having a first end, disposed at the inlet, about which a plurality of stator blades are disposed, a second end, disposed at the outlet, about which a plurality of stator blades are disposed and a stationary hub that connects the first end to the second end;
      a rotor, suspended between the stationary hub and the housing;
      a first radial magnet bearing defined by a first set of magnets of alternating polarity, disposed within the rotor, that define an outer race and a second set of magnets of alternating polarity, disposed within the stator stationary hub, that define an inner race, the inner race and the outer race communicating across a gap between the stationary hub and the rotor to suspend the rotor about the stationary hub;
      a thrust bearing defined by a pair of thrust coils, disposed within the housing, and a pair of magnetic poles, disposed within the rotor, each of the thrust coils interacting with one of the magnetic poles to produce an axial force on the rotor to position the rotor axially within the housing;
      a sensing coil, disposed within the stator, that senses the axial position of the rotor; and
   (ii) a controller, coupled to the sensing coil of the pump that controls an electrical current flowing through the thrust coils to produce a correcting force that positions the rotor axially in response to the position sensed by the sensing coil.

15. The system pump of claim 14, wherein the pump further comprises a second radial magnetic bearing that further comprises a third set of magnets of alternating polarity, disposed within the rotor, and a fourth set of magnets of alternative polarity, disposed within the stator, the third set of alternating magnets and the fourth set of alternating magnets interacting across the gap to define a second radial bearing.

16. The system of claim 14, wherein the pump further comprises a motor, disposed within the housing that communicates with a motor magnet, disposed within the rotor, to rotate the rotor.

17. The system of claim 16, wherein a thickness of the first set of alternating magnets is such that the magnetic interface between the motor magnet and the first set of alternating magnets does not produce an undesirable bending moment on the rotor.

18. The system of claim 14, wherein the controller comprises a virtual zero power controller.

19. A pump for pumping blood, comprising:
   a housing that has an inlet and an outlet;
   a stator, disposed within the housing, and having a first end, that is coupled to the housing proximate to the inlet and a second end, that is coupled to the housing proximate to the outlet;
   a rotor, magnetically suspended between the stator and the housing;
   a radial magnetic bearing that includes a rotor magnet, disposed within the rotor, and a stator magnet, disposed within the stator and aligned with the rotor magnet, the interaction of the rotor magnet and the stator magnet suspending the rotor radially between the housing and the stator;
   a primary flow path defined between the rotor and the housing;
   a secondary flow path defined between the rotor and the stator, the secondary flow path being large enough to provide adequate flushing of the secondary flow path and small enough so that the rotor magnet and the stator magnet can interface to suspend the rotor radially.

20. The pump of claim 19, wherein the flow through the secondary flow path is in a direction that is opposite the flow through the primary flow path.

21. The pump of claim 19, wherein the secondary flow path comprises an entrance disposed between the second end of the stator and the rotor, a substantially inward radial flow path defined between the second end of the stator and the rotor, a substantially axial flow path defined between the stator and the rotor and an exit, defined between the stator and the rotor.

22. The pump of claim 19, further comprising a magnetic thrust bearing for axially aligning the rotor within the housing.

23. The pump of claim 22, wherein the magnetic thrust bearing comprises an active magnetic bearing.

24. The pump of claim 23, wherein the active magnetic thrust bearing comprises a pair of thrust coils, disposed within the housing, that each interact with one of a pair of poles, disposed within the rotor, to place an axial force on the rotor.

25. The pump of claim 24, wherein the active thrust bearing further comprises a sensor, disposed within the stator, for sensing the axial position of the rotor, and an electromagnetic controller, disposed within the pump, that controls the electrical current flowing through the thrust coils to position the rotor axially within the housing.

* * * * *